(12) United States Patent
Gao et al.

(10) Patent No.: US 11,692,004 B2
(45) Date of Patent: Jul. 4, 2023

(54) SUBSTITUTED PYRAZOLE COMPOUND, PREPARATION METHOD THEREFOR, PHARMACEUTICAL COMPOSITION AND MEDICAL USE THEREOF

(71) Applicant: JIANGSU VANGUARD PHARMACEUTICAL CO., LTD., Jiangsu (CN)

(72) Inventors: Qingzhi Gao, Tianjin (CN); Junhua Yao, Tianjin (CN)

(73) Assignee: JIANGSU VANGUARD PHARMACEUTICAL CO., LTD., Jiangsu (CN)

( * ) Notice: Subject to any disclaimer, the term of this patent is extended or adjusted under 35 U.S.C. 154(b) by 0 days.

(21) Appl. No.: 17/267,399

(22) PCT Filed: Aug. 15, 2019

(86) PCT No.: PCT/CN2019/100835
§ 371 (c)(1),
(2) Date: Feb. 9, 2021

(87) PCT Pub. No.: WO2020/038279
PCT Pub. Date: Feb. 27, 2020

(65) Prior Publication Data
US 2022/0372058 A1    Nov. 24, 2022

(30) Foreign Application Priority Data

Aug. 22, 2018   (CN) .......................... 201810959516.7

(51) Int. Cl.
*C07H 17/02* (2006.01)
*C07D 231/26* (2006.01)
*C07D 401/04* (2006.01)
*C07H 1/00* (2006.01)

(52) U.S. Cl.
CPC ........... *C07H 17/02* (2013.01); *C07D 231/26* (2013.01); *C07D 401/04* (2013.01); *C07H 1/00* (2013.01)

(58) Field of Classification Search
CPC ........ C07H 17/02; C07H 1/00; C07D 231/26; C07D 401/04
See application file for complete search history.

(56) References Cited

FOREIGN PATENT DOCUMENTS

WO    WO-2019121734 A1 *   6/2019 ......... A61K 31/7042

OTHER PUBLICATIONS

Watanabe et al., Redox Report, 2003, vol. 8 No. 3, p. 157-161. (Year: 2003).*
Parikh et al., International Journal of Pharmaceutics, 2016, 515, p. 490-500. (Year: 2016).*
Priority document EP17209734.7, WIPO WO2019121734, published Jun. 27, 2019. (Year: 2019).*

* cited by examiner

*Primary Examiner* — Jonathan S Lau
(74) *Attorney, Agent, or Firm* — Booth Udall Fuller, PLC

(57) ABSTRACT

The invention discloses a substituted pyrazole compound of formula (I), preparation method therefor, a pharmaceutical composition and a medical use thereof. The said compound features excellent stability, solubility, and low cytotoxicity, which is significantly beneficial for neurological protection, effectively preventing and treating nerve cell injuries. It is an ideal pharmaceutical compound for preventing or treating stroke, cerebral embolism, stroke sequelae, stroke-related motor dysfunction, mitochondrial encephalomyopathy, and amyotrophic lateral sclerosis.

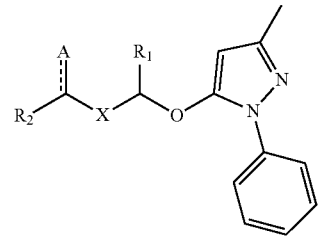

9 Claims, 1 Drawing Sheet

SUBSTITUTED PYRAZOLE COMPOUND, PREPARATION METHOD THEREFOR, PHARMACEUTICAL COMPOSITION AND MEDICAL USE THEREOF

TECHNICAL FIELD

The present invention relates to a substituted pyrazole compound, a preparation method therefor, a pharmaceutical composition and a medical use thereof.

BACKGROUND ART

Cerebrovascular disease is notorious for being high in incidence rate, disability rate, mortality rate and recurrence rate. China is a country of high prevalence of cerebrovascular diseases and stroke (also called cerebral ischemic infarction or cerebral apoplexy) is the main clinical form. According to *Report On Stroke Prevention And Treatment In China:* 2015, China has some 7 million cerebrovascular patients and more than 1.3 million deaths related to the disease every year. Therefore, it has become the first death cause. Nevertheless, the new cases per year in China are more than 2 million, rising by nearly 9% a year. By now the incidence rate in Chinese males is ranked the third among the globe, and the incidence rate in Chinese females has jumped to second place (Sourced from: *Prevalence of stroke in China:* 2015 issued by Stroke Prevention and Treatment Project of the National Health Commission of the People's Republic of China-Peking Union Medical College Press 2015; Prevalence, Incidence and Mortality of Stroke in China: Results from a Nationwide Population-Based Survey of 480,687 Adults. Circulation 2017; 135:759-771).

Stroke is a disease of brain injuries caused by the loss of the blood supply to the brain due to sudden cerebrovascular rupture or blocked vessels, including ischemic and hemorrhagic strokes. Stroke not only produces a high death rate, but it is also the main reason for adult disability in China. The pathological mechanism of the stroke sequelae and post-treatment disability is the surging ROS (reactive oxygen species) and free radicals around locations of cerebral injury duo to blood reperfusion after cerebral ischemia. The radicals will irreversibly damage and finally kill the nerve and brain cells through cell membrane damage, protein damage, nucleic acid/DNA damage, and inducing various inflammatory mediators (References: Oxygen free radicals and ischemic stroke, China Traditional Chinese Medicine Information, 2010; (10) 210-211; Dynamics of free radical processes in acute ischemic stroke: influence on neurological status and outcome. J. Clin. Neurosci. 2004, June, 11(5) 501-506). Therefore, it is difficult to completely solve and prevent the sequelae and disability problems and hidden dangers caused by free radical-induced nerve damage if the clinical treatment of stroke only emphasizes intravenous or arterial thrombolysis.

Similar to stroke, amyotrophic lateral sclerosis (ALS) is also characterized by the injuries and deaths of nerve cells. Although the pathological mechanism is unclear, ALS (also called increasingly frozen disease) proves biologically related to the superoxide dismutase (SOD). SOD is a ubiquitous metal enzyme in organisms, wherein, through disproportionation reaction, toxic substances such as free radicals in mitochondria are oxidized and decomposed into water by SOD1. It is well-recognized by scientists that the mutation of SOD1 is one of the reasons causing ALS (Reference: Supportive and symptomatic management of amyotrophic lateral sclerosis. Nature Reviews. Neurology. 2016, 12 (9): 526-38.).

Mitochondrial encephalomyopathy (ME) is a disease with cerebral and striated muscle dysfunction due to abnormal mitochondrial structures resulting from the losses or mutations of mitochondrial or nuclear genes, which is clinically similar to epilepsy, cerebral infarction, encephalitis, brain dysplasia. ME severely impacts a patient's health and life. Because the mitochondrion is one of the most sensitive cellular organelles susceptible to injuries, pathological studies demonstrate that the attack from oxygen radicals leads to the dysfunction of the mitochondrion and the impacted central nervous system then results in mitochondrial encephalomyopathy (Reference: Progression of imaging study of mitochondrial encephalomyopathy, *Medical Journal of National Defending Forces in Northwest China,* 2011 Vol. 32 No. 2).

The Notice on Publication of List of the First Batch of Rare Diseases in China (GUOWEIYIFU [2018] No. 10) jointly issued by National Health Commission, Ministry of Science and Technology, Ministry of Industry and Information Technology, State Drug Administration and State Administration of Traditional Chinese Medicine explicitly stipulates ALS and ME are rare diseases and orphan diseases in China. As a rare disease, though in low incidence rate, so far China has 100,000-200,000 cases based on incomplete statistics because of a large population. Even now, there are no drugs available eradicating the disease. The ALS incidence rate in adults is about 1/4300 and 1/2000 in children. Therefore, the development of ALS drugs and improving patients' health is the common goal of the biological medicine scientists of China and the rest of the world and a key project of medicine and health industry in China. ((References: Progress in Clinical Diagnosis of Amyotrophic Lateral Sclerosis [Yang Qiong, Fan Dongsheng. *Chinese Journal of Contemporary Neurology and Neurosurgery,* 2012.6 Vol. 12 No. 3; Current Status of Epidemiological Research on Amyotrophic Lateral Sclerosis [J]. *Chinese Journal of Neurology,* 2015, 48(6): 542-544))

SUMMARY OF THE INVENTION

The inventors elaborate a novel substituted pyrazole compound effectively preventing and/or treating nerve cell injuries.

The subject matter herein discloses a substituted pyrazole compound of formula (I), or a pharmaceutically acceptable salt thereof, or a solvate thereof,

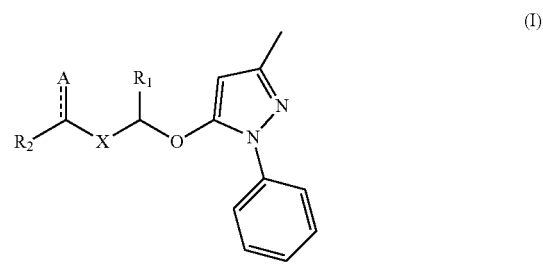

wherein:
$R_1$ is H or alkyl;
X is —O—, —S— or —NH—;
⚌ is a double bond and A is O;

R$_2$ is H, alkyl, cycloalkyl, non-aromatic heterocyclic group, aryl, heteroaryl, aryl alkyl, or heteroaryl alkyl that are optionally substituted, the said "optionally substituted" means R$_2$ may be substituted by none, one or more than one group selected from hydroxy, alkoxy, aryloxy, arylalkoxy, halogen, alkanoyloxy, alkoxyacyloxy, unsubstituted or alkyl-substituted amino;

alternatively, $\equiv$ is a single bond, and the following formula (i) part in formula (I)

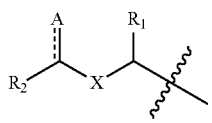

(i)

forms the group of the following formula (ii),

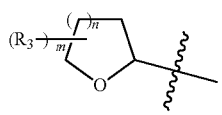

(ii)

wherein n is 1 or 2, and m is 1, 2, 3, or 4,

R$_3$ is independently hydroxy, hydroxymethyl, alkanoyloxy (preferably acetoxy), benzoyloxy (preferably benzoyloxy, p-chlorobenzoyloxy) optionally substituted by halogen, alkanoyloxymethyl (preferably acetoxymethyl), benzoyloxymethyl (preferably benzoyloxymethyl, p-chlorobenzoyloxymethyl) optionally substituted by halogen, alkoxy, alkoxymethyl, or unsubstituted or mono- or di-substituted amino by the group selected from alkyl, alkanoyl (preferably acetyl), benzoyl (preferably benzoyl, p-chlorobenzoyl) that is optionally substituted by halogen;

optionally, the alkyl moiety of the "alkyl", "aralkyl", "heteroaralkyl", "alkoxy", "arylalkoxy", "alkanoyloxy", "alkoxyacyloxy" and "alkanoyloxymethyl" is each independently a C$_{1-20}$ linear or branched alkyl; optionally, a C$_{1-17}$ linear or branched alkyl; optionally, a C$_{1-8}$ linear or branched alkyl; optionally, a C$_{1-6}$ linear or branched alkyl; optionally, a C$_{1-4}$ linear or branched alkyl; optionally, methyl, ethyl, n-propyl, isopropyl, n-butyl, isobutyl, tert-butyl, sec-butyl, n-pentyl, isopentyl, neopentyl, tert-pentyl, n-hexyl, isohexyl, heptyl, n-octyl, n-nonyl, n-decyl, dodecyl, pentadecyl or hexadecyl;

optionally, the "cycloalkyl" is a C$_{3-8}$ cycloalkyl, optionally, a cyclopropyl, cyclobutyl, cyclopentyl, or cyclohexyl;

optionally, the "non-aromatic heterocyclic group" is a non-aromatic C$_{3-8}$ heterocyclic group containing 1-2 heteroatoms selected from O, N and S, optionally, oxiranyl, oxetanyl, tetrahydrofuranyl, tetrahydropyrrolyl, tetrahydropyranyl, piperidinyl, piperazinyl, or morpholinyl;

optionally, the aryl moiety in the "aryl" and the "aralkyl" is phenyl or naphthyl;

optionally, the heteroaryl moiety in the "heteroaryl" and the "heteroaralkyl" is each independently a 5-10 membered monocyclic group or fused bicyclic aromatic heterocyclic group containing 1-2 heteroatoms selected from O, N and S; optionally, pyrrolyl, furyl, pyridyl, pyrazinyl, or pyrimidinyl.

Optionally, the disclosure herein provides the substituted pyrazole compound of formula (I), or the pharmaceutically acceptable salt thereof, or the solvate thereof, wherein R$_1$ is hydrogen or methyl;

X is —O— or —NH—

$\equiv$ is a double bond and A is O;

R$_2$ is C$_1$-C$_{17}$ branched or linear alkyl, C$_{3-6}$ cycloalkyl, phenyl-C$_1$-C$_6$ alkyl, pyridyl, phenyl optionally substituted by one or more groups selected from hydroxyl, C$_{1-6}$ alkanoyloxy, C$_{1-6}$ alkoxy acyloxy or —NR'R" substituted wherein R' and R" are each independently C$_1$-C$_6$ linear or branched alkyl.

Alternatively, $\equiv$ is a single bond and the following formula (i) in formula (I) forms the group of formula (ii), wherein n is 1 or 2, and m is 2, 3 or 4, R$_3$ is each independently hydroxy, hydroxymethyl, or unsubstituted or mono-substituted amino with C$_{1-6}$ alkanoyl.

Optionally, the substituted pyrazole compound of the formula (I), or the pharmaceutically acceptable salt thereof, or the solvate thereof, wherein the substituted pyrazole compound of formula (I) is the compound of the following formula II, III or IV,

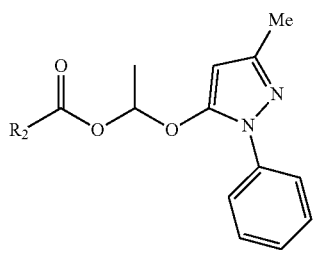

II

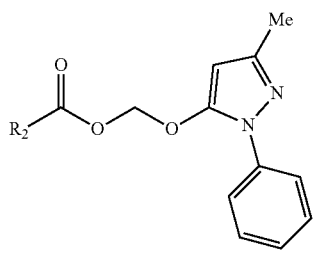

III

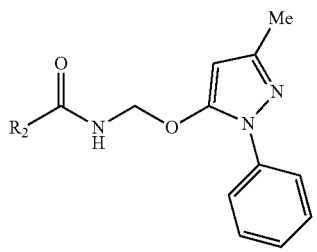

IV wherein, R$_2$ is defined in aforesaid description.

Optionally, the substituted pyrazole compound of the formula (I) or the pharmaceutically acceptable salt thereof, or the solvate thereof, wherein, the formula (i) in formula (I) forms the group of the following formula (iii) or (iv),

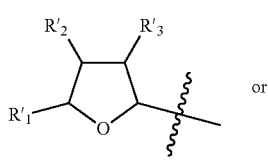 (iii) or

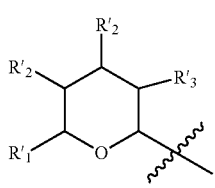 (iv)

wherein, R'₁ is hydrogen, hydroxymethyl, or $C_{1-4}$ alkanoyloxymethyl; R'₂ is hydroxy or $C_{1-4}$ alkanoyloxy; R'₃ is hydrogen, hydroxy, $C_{1-4}$ alkanoyloxy, amino, or $C_{1-4}$ alkanoylamino.

Optionally, the substituted pyrazole compound of the formula (I), or the pharmaceutically acceptable salt thereof, or the solvate thereof, wherein the formula (i) of the formula (I) forms the groups shown in the following formulas,

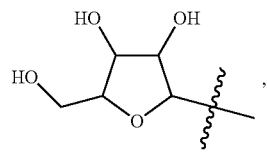,

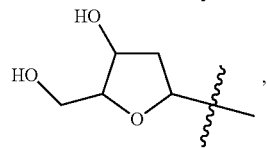,

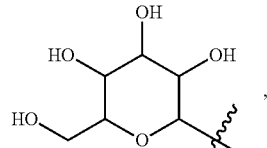,

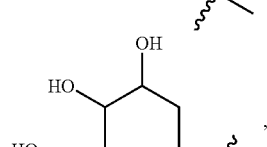,

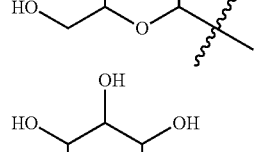 or

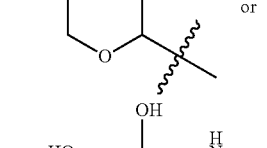

Optionally, the substituted pyrazole compound of the formula (I), or the pharmaceutically acceptable salt thereof, or the solvate thereof, wherein the compound of formula (I) is selected from the following compounds:

| No. | Structure |
|---|---|
| 1 | 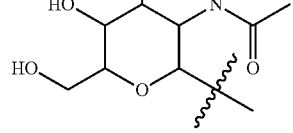 |
| 2 | 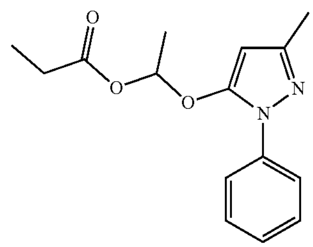 [SMILES: CCC(=O)OC(C)Oc1cc(C)nn1-c1ccccc1] |
| 3 | 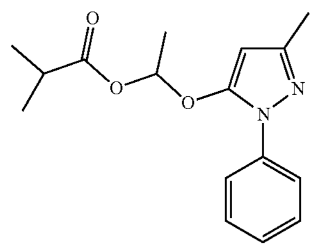 [SMILES: Cc1cc(OC(C)OC(=O)C(C)C)n(-c2ccccc2)n1] |
| 4 | 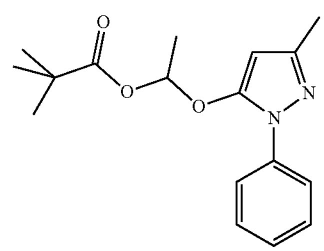 [SMILES: Cc1cc(OC(C)OC(=O)C(C)(C)C)n(-c2ccccc2)n1] |
| 5 | 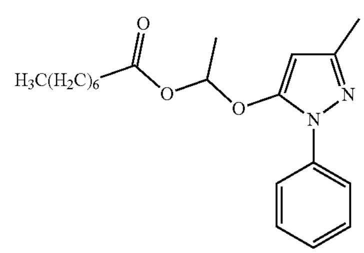 |
| 6 | 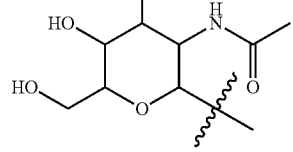 |

| No. | Structure |
|---|---|
| 7 | 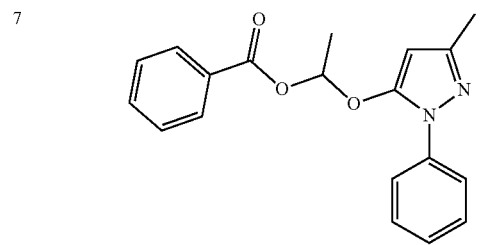 |
| 8 | 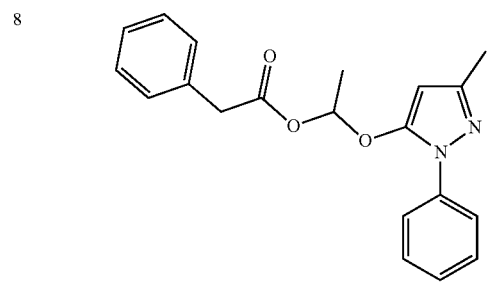 |
| 9 | 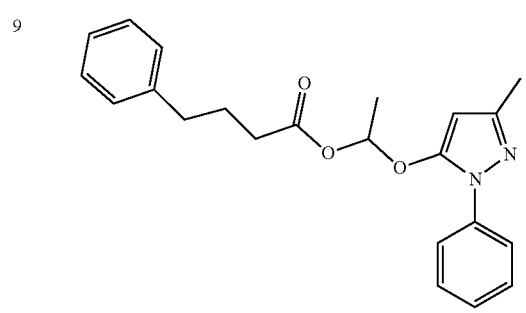 |
| 10 | 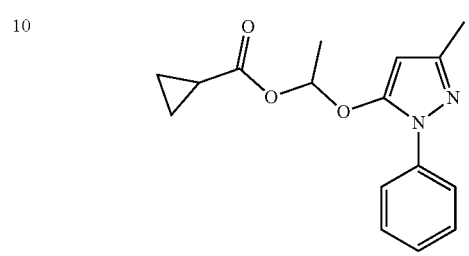 |
| 11 | 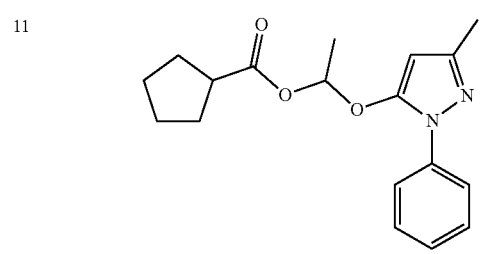 |
| 12 | 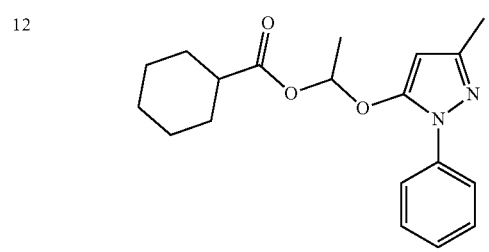 |
| No. | Structure |
|---|---|
| 13 | 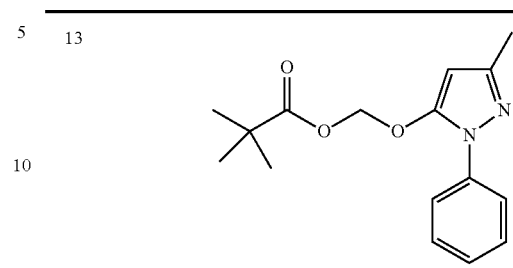 |
| 14 | 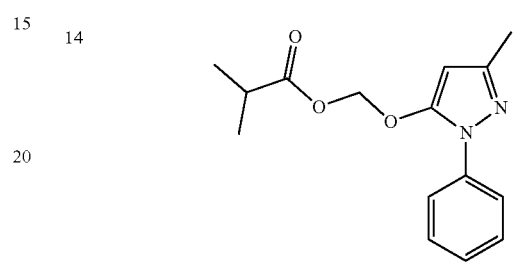 |
| 15 | 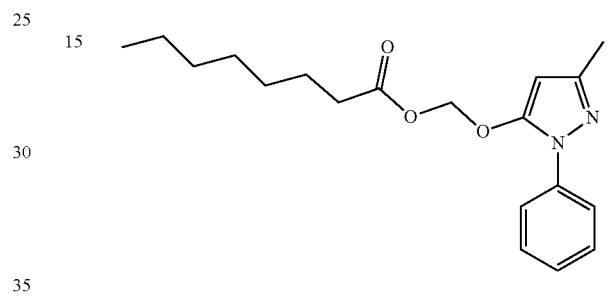 |
| 16 | 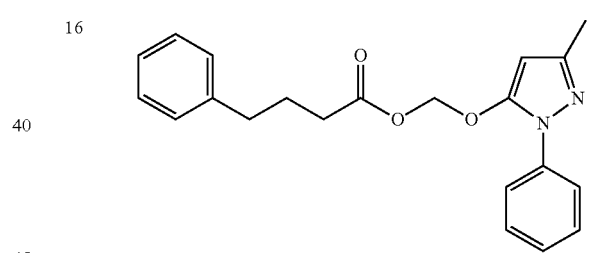 |
| 17 | 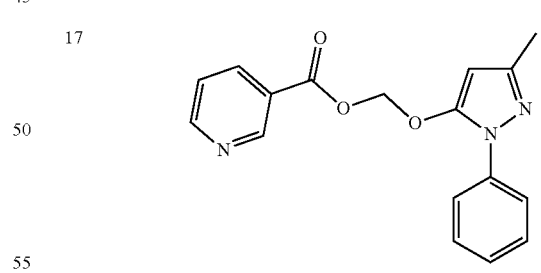 |
| 18 | 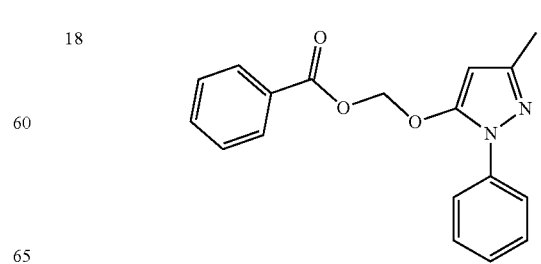 |

| No. | Structure |
|---|---|
| 19 | 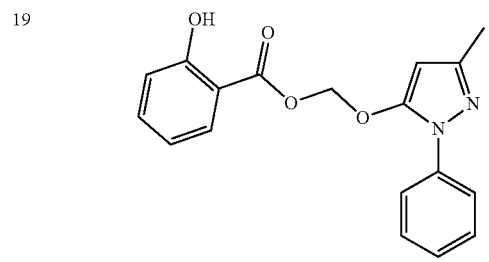 |
| 20 | 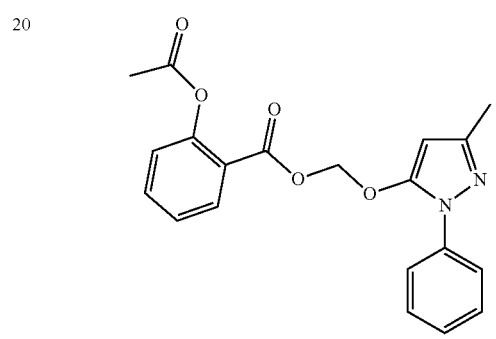 |
| 21 | 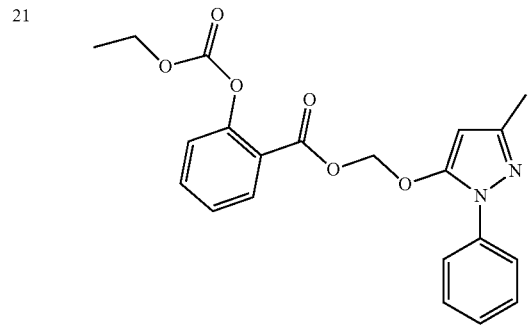 |
| 22 | 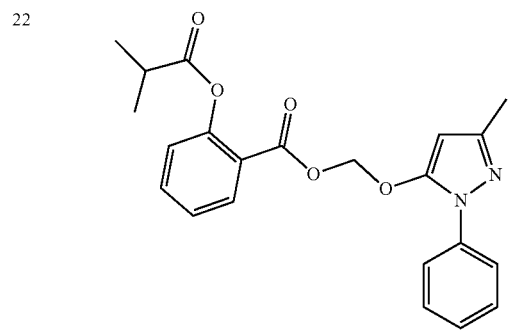 |
| 23 | 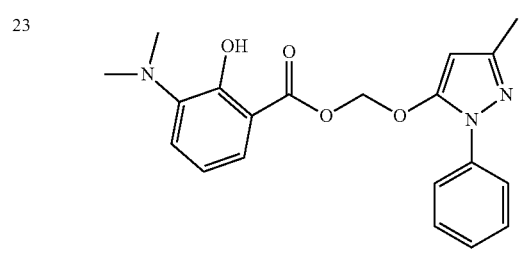 |
| 24 | 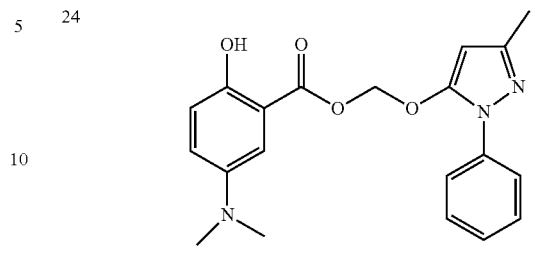 |
| 25 | 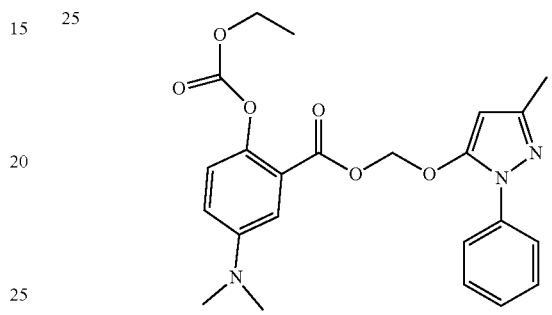 |
| 26 | 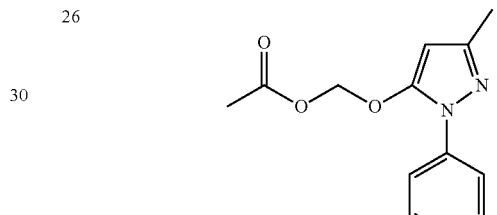 |
| 27 | 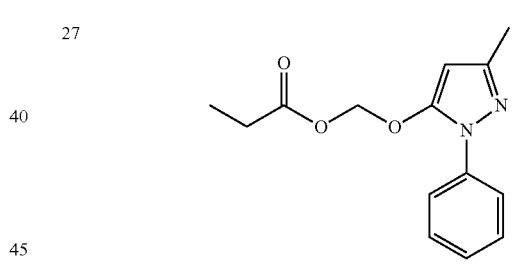 |
| 28 | 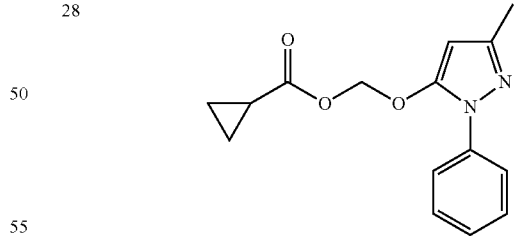 |
| 29 | 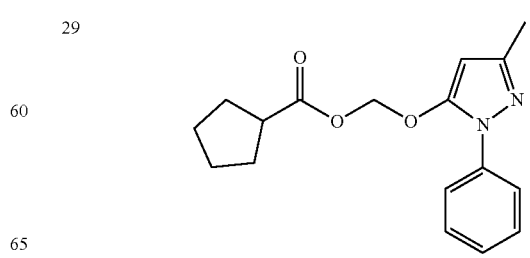 |

| No. | Structure |
|---|---|
| 30 | (chemical structure) |
| 31 | (chemical structure) |
| 32 | (chemical structure) |
| 33 | (chemical structure) |
| 34 | (chemical structure) |
| 35 | (chemical structure) |
| 36 | (chemical structure) |
| 37 | (chemical structure) |
| 38 | (chemical structure) |
| 39 | (chemical structure) |

| No. | Structure |
|---|---|
| 40 | 1-phenyl-3-methyl-pyrazol-5-yl 2-deoxyribofuranoside |
| 41 | N-((3-methyl-1-phenyl-1H-pyrazol-5-yloxy)methyl)acetamide |
| 42 | N-((3-methyl-1-phenyl-1H-pyrazol-5-yloxy)methyl)propanamide |
| 43 | N-((3-methyl-1-phenyl-1H-pyrazol-5-yloxy)methyl)isobutyramide |
| 44 | N-((3-methyl-1-phenyl-1H-pyrazol-5-yloxy)methyl)pivalamide |
| 45 | N-((3-methyl-1-phenyl-1H-pyrazol-5-yloxy)methyl)cyclopropanecarboxamide |

| No. | Structure |
|---|---|
| 46 | N-((3-methyl-1-phenyl-1H-pyrazol-5-yloxy)methyl)cyclopentanecarboxamide |
| 47 | N-((3-methyl-1-phenyl-1H-pyrazol-5-yloxy)methyl)cyclohexanecarboxamide |
| 48 | N-((3-methyl-1-phenyl-1H-pyrazol-5-yloxy)methyl)benzamide |
| 49 | N-((3-methyl-1-phenyl-1H-pyrazol-5-yloxy)methyl)-2-phenylacetamide |
| 50 | N-((3-methyl-1-phenyl-1H-pyrazol-5-yloxy)methyl)-4-phenylbutanamide |
| 51 | $H_3C(H_2C)_6$-C(O)-NH-CH$_2$-O-(3-methyl-1-phenyl-1H-pyrazol-5-yl) |

-continued

| No. | Structure |
|---|---|
| 52 | 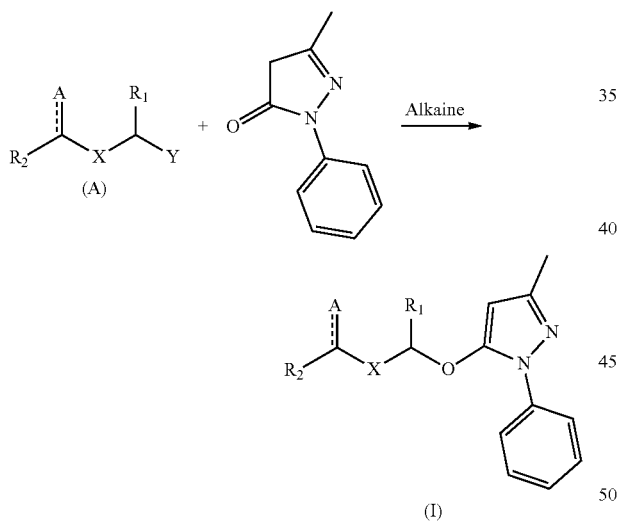 |

Optionally, the substituted pyrazole compound of the formula (I), or the pharmaceutically acceptable salt thereof, or the solvate thereof, which comprises various optical isomers. The glycoside compound involved may be α-form or β-form. For example, the compounds 33-40 may be α-form or β-form.

In a further aspect, the disclosure provides a preparation method for the substituted pyrazole compound of the formula (I), or the pharmaceutically acceptable salt thereof, or the solvate thereof, comprising the step of reacting the compound of formula (A) and edaravone under alkaline conditions,

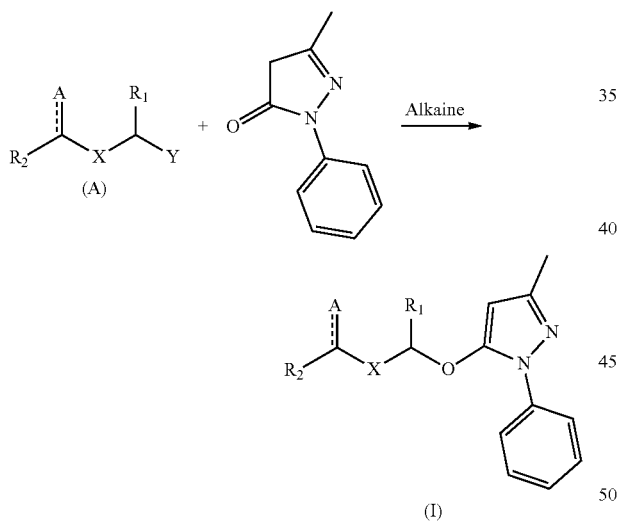

wherein, $R_1$, X, A, $R_2$ and ⹀ are as defined in the aforesaid description, and Y is halogen, preferably Cl or Br.

Optionally, wherein, the compound of formula (I) is the compound of formula (II), and the synthetic route of the preparation method is as follows:

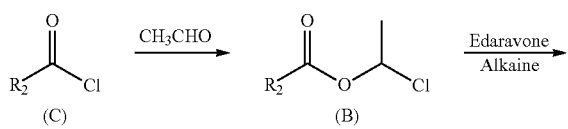

-continued

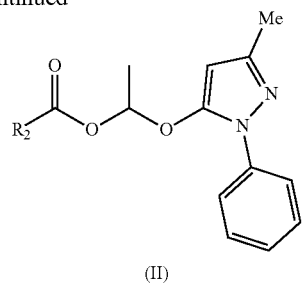

(II)

The preparation method comprises:

reacting the compound of formula (C) with acetaldehyde under a catalyst to obtain the compound of formula (B); and reacting the compound of formula (B) reacts with edaravone under alkaline conditions to prepare the compound of formula (II);

optionally, the preparation method of the formula (C) comprises the step of the reaction between the compound of the formula (D) and thionyl chloride;

alternatively,

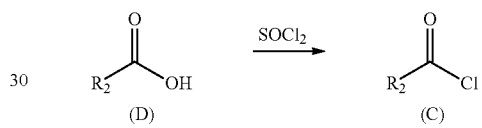

the compound of formula (I) is the compound of formula (III), and the synthetic route of the preparation method is as follows:

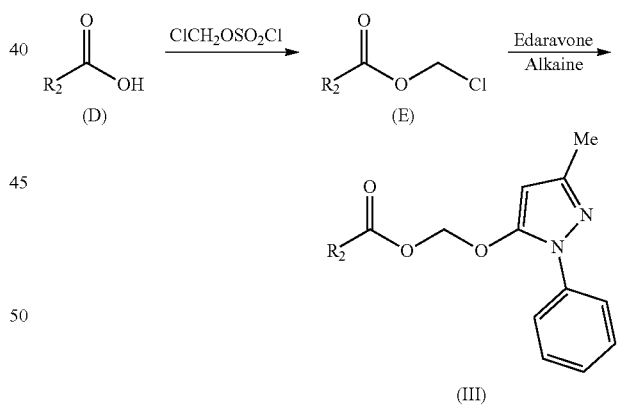

the preparation method comprises:
reacting the compound of formula (D) with chloromethyl chlorosulfonate to obtain the compound of formula (E); and reacting the compound of formula (E) with edaravone under alkaline conditions to prepare the compound of formula (III);

alternatively, the compound of formula (I) is the compound of formula (IV), and the synthetic route of the preparation method is as follows:

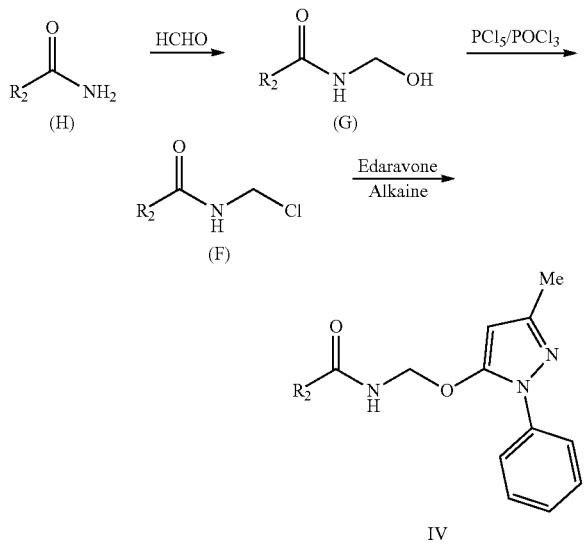

the preparation method comprises:

reacting the compound of formula (H) with formaldehyde to obtain the compound of formula (G);

reacting the compound of formula (G) with PCl$_5$/POCl$_3$ to prepare the compound of formula (F);

reacting the compound of formula (F) with edaravone under alkaline conditions to prepare the compound of formula (IV);

alternatively, the compound of formula (I) is the compound of the following formula (V), and the synthetic route of the preparation method is as follows:

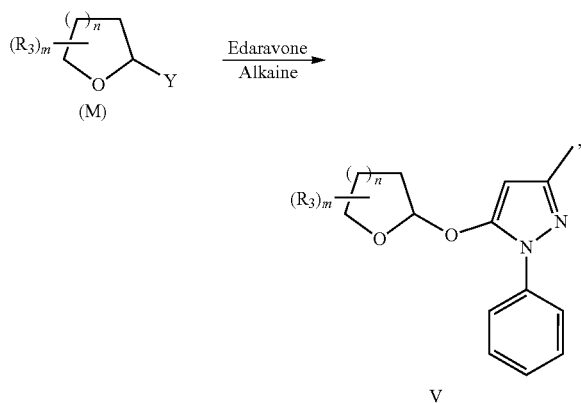

wherein Y is Cl or Br, the preparation method comprises the step of reacting the compound of the formula (M) and edaravone under alkaline conditions to prepare the compound of formula (V); in the above structural formula, R$_2$, R$_3$, m, and n are as defined in the aforesaid description.

Optionally, the optical isomers of the substituted pyrazole compound of the formula (I), or the pharmaceutically acceptable salt thereof, or the solvate thereof may be prepared through different synthetic or separation methods. As for the a or R form of the compound, the compounds of 33, 34, 35, 36, 37, 38, 39, and 40 may be prepared through different synthetic or separation methods.

In a further aspect, the disclosure provides a pharmaceutical composition comprising one or more than one of the substituted pyrazole compounds of formula (I) or the pharmaceutically acceptable salt thereof, or the solvate thereof and optional pharmaceutically acceptable carriers.

The substituted pyrazole compound of the formula (I) as disclosed above, the pharmaceutically acceptable salt thereof or the solvate thereof can be manufactured into pharmaceuticals with different performances such as parenteral administration, oral administration, spraying administration, etc. At least one of said compounds can be administered alone or combing with pharmaceutical carriers, adjuvants, vehicles, excipients, diluents, etc. The pharmaceutical composition includes, but not limited to, injections, capsules, powders, granules, tablets, pills, syrups, emulsions, suspensions, solutions, etc., which are made by conventional methods.

Parenteral administration includes subcutaneous injection, intravenous injection, intramuscular injection, intraperitoneal injection, or intravenous infusion. Injection formulation, such as sterile injection, can be made by suspending liquids including water and oil, with suitable dispersing or wetting agents, and other suspending agents. The sterile injection formulation can also be a sterile injection solution, a suspension, or a sterile freezing-dried powder for injection, wherein a non-toxic parenteral diluent or solvent, such as water, is used. Suitable carriers or solvents that can be used include water, Ringer's solution, and isotonic sodium chloride solution. In addition, sterile non-volatile oil can also be used as a solvent or suspension medium. The oil herein is different types of non-volatile oils or fatty acids, including natural, synthetic, or semi-synthetic fatty oils or acids, and natural, synthetic, or semi-synthetic mono-, di-, or triglycerides.

Oral solid formulation includes the above-mentioned powders, granules, tablets, pills, and capsules, among which the active compound can be mixed with at least one additive, such as sucrose, lactose, cellulose, mannitol, maltose, dextrin, starch, agar, alginate, chitin, chitosan, pectin, donkey-hide gelatin, gelatin, collagen, casein, albumin, and synthetic or semi-synthetic polymers or glycerides. Apart from inert carriers, the formulation herein may also include other ingredients such as lubricants like magnesium stearate, preservatives like parabens and sorbitol, and antioxidants such as ascorbic acid, tocopherol and cysteine, disintegrating agents, binders, thickeners, buffers, sweeteners, fragrances and flavoring agents. Tablets and pills can be made by adding an external coating.

Oral liquid formulation includes medicinal emulsions, syrups, suspensions, and solutions, containing diluents, such as water commonly used in the prior art.

In a further aspect, the disclosure herein provides a medical use of the substituted pyrazole compound of formula (I) or the pharmaceutically acceptable salt thereof, or the solvate thereof, or the pharmaceutical composition thereof in the preparation of the drugs in preventing or treating the diseases including stroke, cerebral embolism, stroke sequelae, stroke motor dysfunction, mitochondrial encephalomyopathy, amyotrophic lateral sclerosis.

In still a further aspect, the disclosure herein provides a medical use of the substituted pyrazole compound of formula (I) or the pharmaceutically acceptable salt thereof, or the solvate thereof, or the pharmaceutical composition thereof in the preparation of the drugs in preventing or treating the diseases including stroke, cerebral embolism, stroke sequelae, stroke motor dysfunction, mitochondrial encephalomyopathy and/or amyotrophic lateral sclerosis.

The specific dosage for any particular patient depends on various factors, including the activity of the compound used, age, weight, general health conditions, gender, diet, time of administration, mode of administration, secretion rate, drug combination, and specific conditions. The dosage varies with the diseases, symptoms, objects, and routes of administration. For adult treatment, the daily dosage is 1-300 mg for oral administration or 1-100 mg for intravenous administration, subdivided into two or three doses. For example, for ischemic stroke, the active ingredient is used in an appropriate amount, such as about 10-200 mg per dose orally or about 5-100 mg per dose intravenously and given in equal doses 2 or 3 times per day.

The disclosure herein provides a substituted pyrazole compound of formula (I) or a pharmaceutically acceptable salt thereof, or a solvate thereof, effectively preventing and treating nerve cell damages.

In a further aspect, the disclosure herein provides a substituted pyrazole compound of formula (I) or a pharmaceutically acceptable salt thereof, or a solvate thereof, having excellent stability.

In a further aspect, the disclosure herein provides a substituted pyrazole compound of formula (I) or a pharmaceutically acceptable salt thereof, or a solvate thereof, having excellent water solubility.

In a further aspect, the disclosure herein provides a substituted pyrazole compound of formula (I) or a pharmaceutically acceptable salt thereof, or a solvate thereof, posing low cytotoxic.

In a further aspect, the disclosure herein provides a substituted pyrazole compound of formula (I) or a pharmaceutically acceptable salt thereof, or a solvate thereof, posing remarkable neurologically protective, effectively preventing or treating stroke, cerebral embolism, stroke sequelae, stroke motor dysfunction, mitochondrial encephalomyopathy and/or amyotrophic lateral sclerosis.

DETAILED DESCRIPTION

Figure 1:
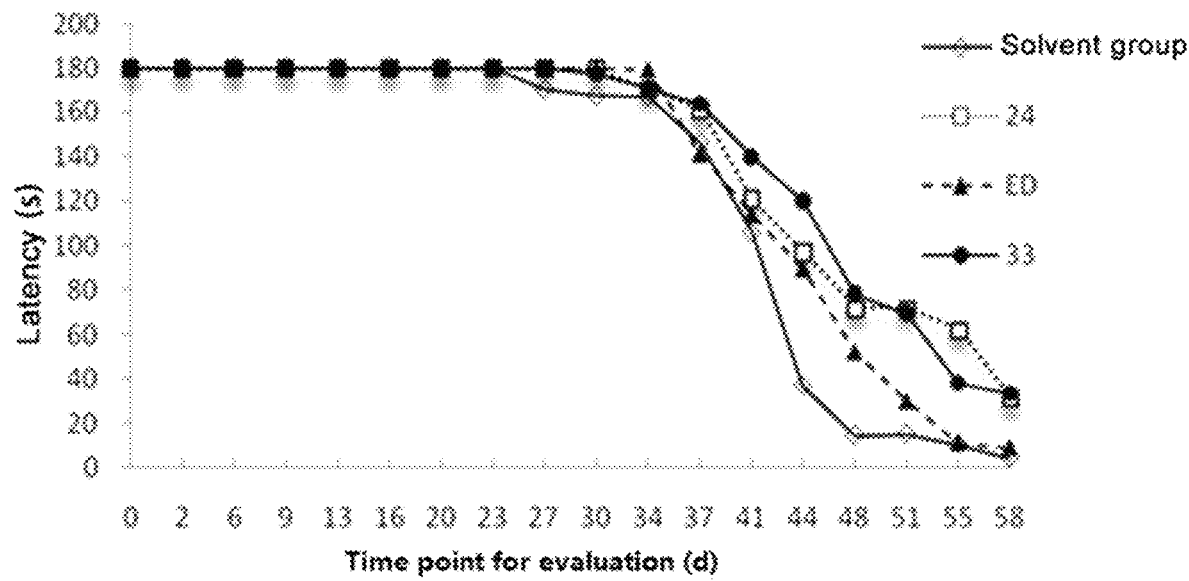
FIG. 1 depicts the curve of the time-fall latency of the ALS mice in Rota-rod Test.
Figure 2:
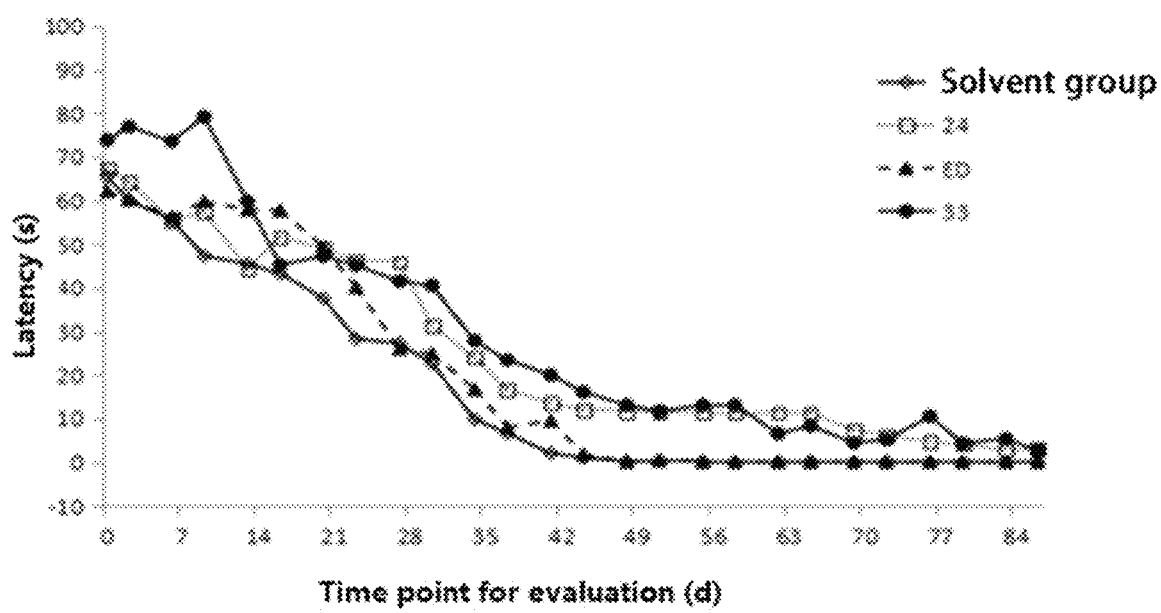
FIG. 2 depicts the curve of the time-fall latency of the ALS mice in PaGE Test.

The invention will be explained below in more detail by reference to examples. However, the invention should not be construed as being limited to scope of the Invention by the following examples.

The representative compounds of the invention are listed in Table 1.

TABLE 1

| No. | Structure | ESI-MS(m/z): [M]$^+$ | Element analysis |
| --- | --- | --- | --- |
| 1 | 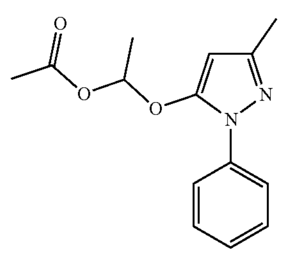 [SMILES: CC(=O)OC(C)Oc1cc(C)nn1-c1ccccc1] | 261.14 | C, 64.61; H, 6.25; N, 10.73 |
| 2 | 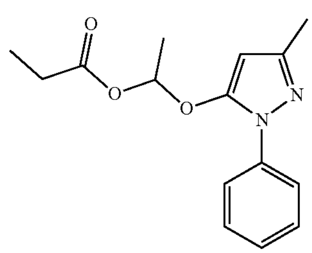 [SMILES: CCC(=O)OC(C)Oc1cc(C)nn1-c1ccccc1] | 275.17 | C, 65.61; H, 6.65; N, 10.19 |
| 3 | 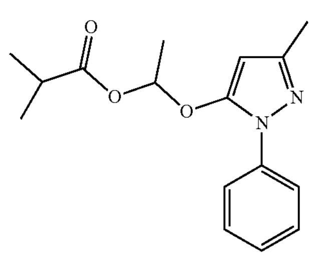 [SMILES: Cc1cc(OC(C)OC(=O)C(C)C)n(-c2ccccc2)n1] | 289.20 | C, 66.66; H, 7.02; N, 9.69 |

TABLE 1-continued

| No. | Structure | ESI-MS(m/z): [M]+ | Element analysis |
|---|---|---|---|
| 4 | 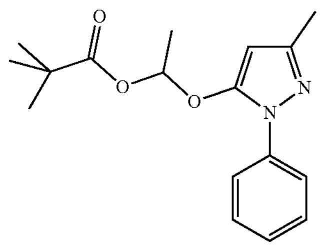 [SMILES: Cc1cc(OC(C)OC(=O)C(C)(C)C)n(-c2ccccc2)n1] | 303.30 | C, 67.52; H, 7.36; N, 9.24 |
| 5 | 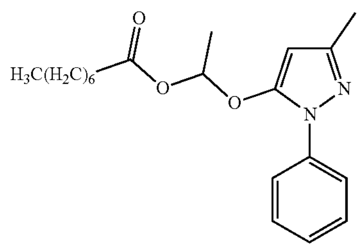 | 345.19 | C, 69.73; H, 8.22; N, 8.12 |
| 6 | 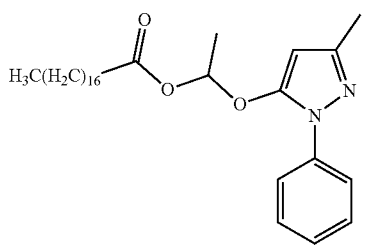 | 485.41 | C, 74.35; H, 10.02; N, 5.75 |
| 7 | 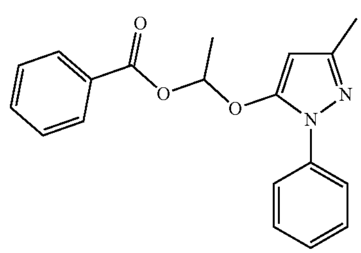 [SMILES: Cc1cc(OC(C)OC(=O)c2ccccc2)n(-c2ccccc2)n1] | 323.19 | C, 70.76; H, 5.70; N, 8.65 |
| 8 | 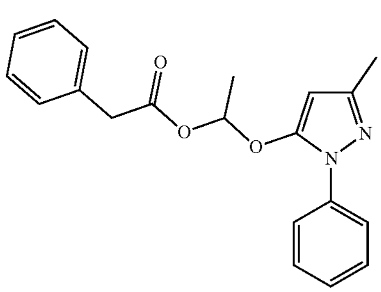 [SMILES: Cc1cc(OC(C)OC(=O)Cc2ccccc2)n(-c2ccccc2)n1] | 337.18 | C, 71.40; H, 6.03; N, 8.30 |

TABLE 1-continued

| No. | Structure | ESI-MS(m/z): [M]+ | Element analysis |
|---|---|---|---|
| 9 | 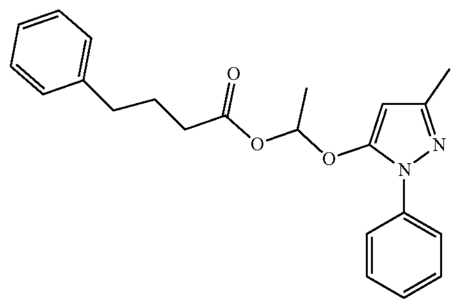 [SMILES: Cc1cc(OC(C)OC(=O)CCCc2ccccc2)n(-c2ccccc2)n1] | 365.25 | C, 72.51; H, 6.70; N, 7.69 |
| 10 | 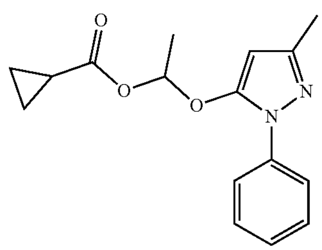 [SMILES: Cc1cc(OC(C)OC(=O)C2CC2)n(-c2ccccc2)n1] | 287.11 | C, 67.11; H, 6.34; N, 9.77 |
| 11 | 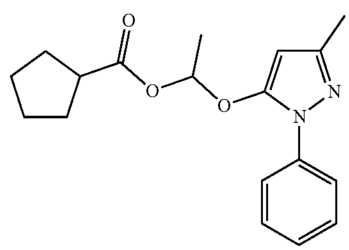 [SMILES: Cc1cc(OC(C)OC(=O)C2CCCC2)n(-c2ccccc2)n1] | 315.14 | C, 68.75; H, 7.08; N, 8.90 |
| 12 | 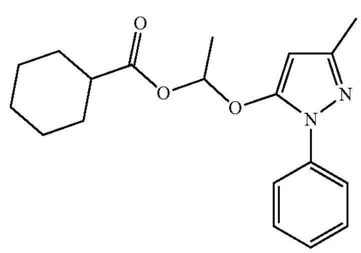 [SMILES: Cc1cc(OC(C)OC(=O)C2CCCCC2)n(-c2ccccc2)n1] | 329.25 | C, 69.46; H, 7.41; N, 8.51 |
| 13 | 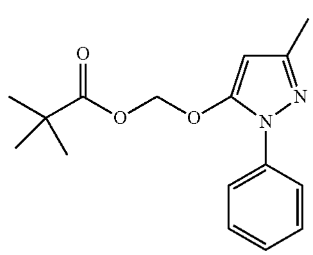 [SMILES: Cc1cc(OCOC(=O)C(C)(C)C)n(-c2ccccc2)n1] | 289.22 | C, 66.64; H, 7.05; N, 9.70 |
| 14 | 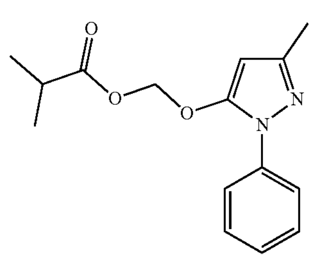 [SMILES: Cc1cc(OCOC(=O)C(C)C)n(-c2ccccc2)n1] | 275.18 | C, 65.66; H, 6.61; N, 10.23 |

TABLE 1-continued
| No. | Structure | ESI-MS(m/z): [M]+ | Element analysis |
|---|---|---|---|
| 15 | 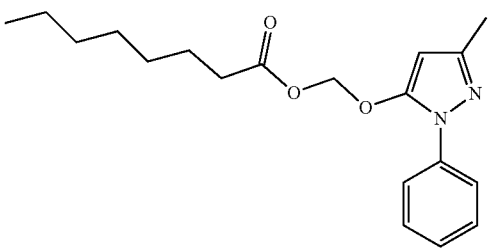 [SMILES: CCCCCCCC(=O)OCOc1cc(C)nn1-c1ccccc1] | 331.24 | C, 69.08; H, 7.91; N, 8.48 |
| 16 | 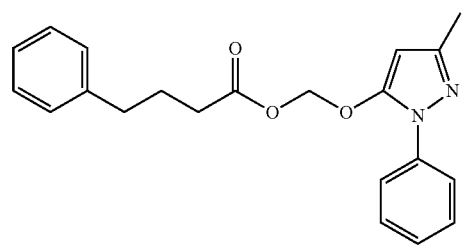 [SMILES: Cc1cc(OCOC(=O)CCCc2ccccc2)n(-c2ccccc2)n1] | 351.13 | C, 71.96; H, 6.35; N, 7.97 |
| 17 | 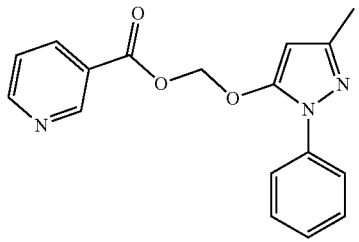 [SMILES: Cc1cc(OCOC(=O)c2cccnc2)n(-c2ccccc2)n1] | 310.15 | C, 66.03; H, 4.91; N, 13.56 |
| 18 | 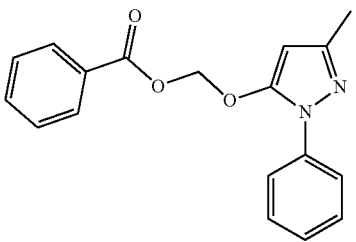 | 309.17 | C, 70.11; H, 5.25; N, 9.07 |
| 19 | 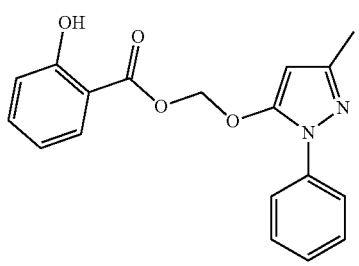 [SMILES: Cc1cc(OCOC(=O)c2ccccc2O)n(-c2ccccc2)n1] | 325.01 | C, 66.60; H, 4.98; N, 8.66 |

TABLE 1-continued

| No. | Structure | ESI-MS(m/z): [M]+ | Element analysis |
|---|---|---|---|
| 20 | 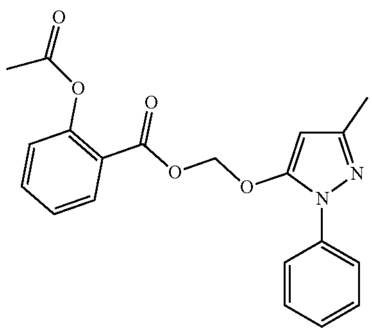 [SMILES: CC(=O)Oc1ccccc1C(=O)OCOc1cc(C)nn1-c1ccccc1] | 367.18 | C, 65.55; H, 4.99; N, 7.63 |
| 21 | 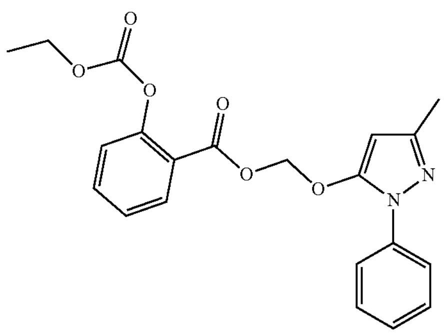 [SMILES: CCOC(=O)Oc1ccccc1C(=O)OCOc1cc(C)nn1-c1ccccc1] | 397.18 | C, 63.62; H, 5.11; N, 7.06 |
| 22 | 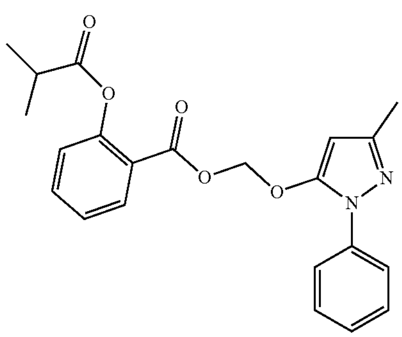 [SMILES: Cc1cc(OCOC(=O)c2ccccc2OC(=O)C(C)C)n(-c2ccccc2)n1] | 395.21 | C, 66.94; H, 5.68; N, 7.08 |
| 23 | 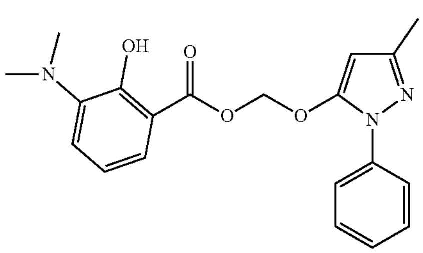 | 368.19 | C, 65.35; H, 5.78; N, 11.42 |
| 24 | 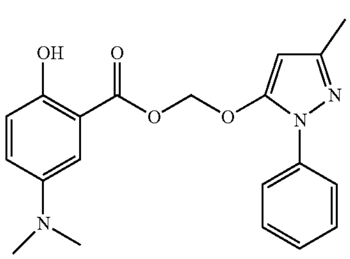 [SMILES: Cc1cc(OCOC(=O)c2cc(N(C)C)ccc2O)n(-c2ccccc2)n1] | 368.22 | C, 65.39; H, 5.74; N, 11.43 |

TABLE 1-continued

| No. | Structure | ESI-MS(m/z): [M]+ | Element analysis |
|---|---|---|---|
| 25 | 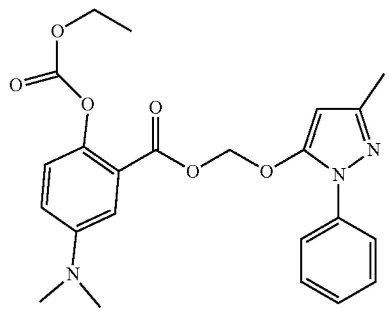 [SMILES: CCOC(=O)Oc1ccc(N(C)C)cc1C(=O)OCOc1cc(C)nn1-c1ccccc1] | 440.21 | C, 62.85; H, 5.75; N, 9.54 |
| 26 | 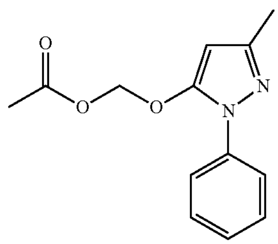 [SMILES: CC(=O)OCOc1cc(C)nn1-c1ccccc1] | 247.13 | C, 63.38; H, 5.75; N, 11.35 |
| 27 | 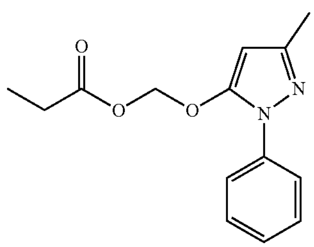 [SMILES: CCC(=O)OCOc1cc(C)nn1-c1ccccc1] | 261.02 | C, 64.61; H, 6.21; N, 10.74 |
| 28 | 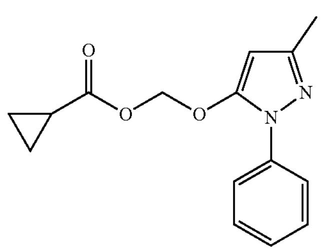 [SMILES: Cc1cc(OCOC(=O)C2CC2)n(-c2ccccc2)n1] | 273.18 | C, 66.15; H, 5.98; N, 10.27 |
| 29 | 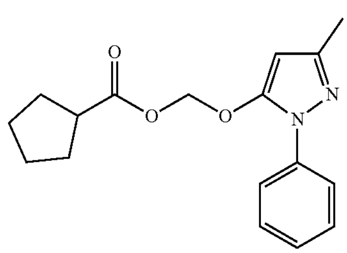 [SMILES: Cc1cc(OCOC(=O)C2CCCC2)n(-c2ccccc2)n1] | 301.23 | C, 67.94; H, 6.76; N, 9.38 |
| 30 | 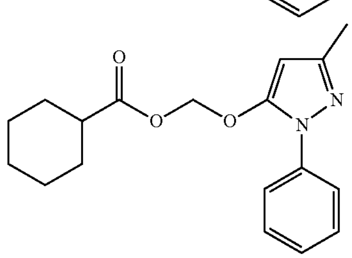 | 315.19 | C, 68.76; H, 7.10; N, 8.88 |

TABLE 1-continued

| No. | Structure | ESI-MS(m/z): [M]+ | Element analysis |
|---|---|---|---|
| 31 | 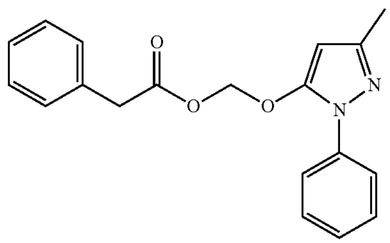 [SMILES: Cc1cc(OCOC(=O)Cc2ccccc2)n(-c2ccccc2)n1] | 323.20 | C, 70.77; H, 5.68; N, 8.65 |
| 32 | 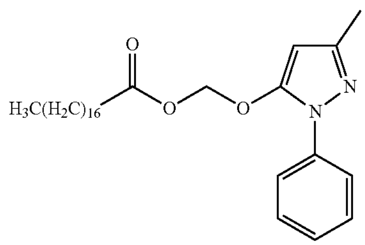 | 471.26 | C, 73.98; H, 9.87; N, 5.91 |
| 33 | 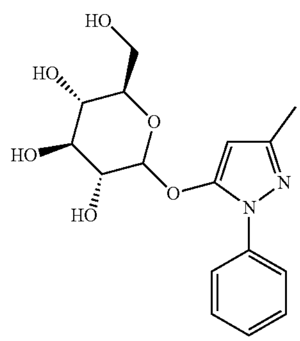 [SMILES: Cc1cc(OC2O[C@H](CO)[C@@H](O)[C@H](O)[C@H]2O)n(-c2ccccc2)n1] | 337.15 | C, 57.13; H, 5.98; N, 8.34 |
| 34 | 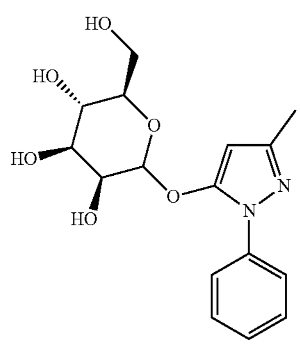 [SMILES: Cc1cc(OC2O[C@H](CO)[C@@H](O)[C@H](O)[C@@H]2O)n(-c2ccccc2)n1] | 337.14 | C, 57.12; H, 6.02; N, 8.31 |
| 35 | 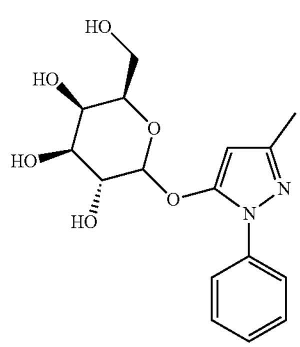 [SMILES: Cc1cc(OC2O[C@H](CO)[C@H](O)[C@H](O)[C@H]2O)n(-c2ccccc2)n1] | 337.17 | C, 57.12; H, 5.99; N, 8.35 |

TABLE 1-continued

| No. | Structure | ESI-MS(m/z): [M]+ | Element analysis |
|---|---|---|---|
| 36 | 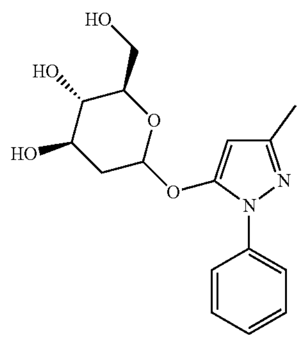 [SMILES: Cc1cc(OC2C[C@@H](O)[C@H](O)[C@@H](CO)O2)n(-c2ccccc2)n1] | 321.20 | C, 59.94; H, 6.32; N, 8.73 |
| 37 | 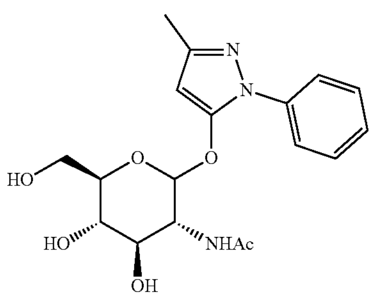 [SMILES: CC(=O)N[C@H]1C(Oc2cc(C)nn2-c2ccccc2)O[C@H](CO)[C@@H](O)[C@@H]1O] | 378.19 | C, 57.27; H, 6.16; N, 11.11 |
| 38 | 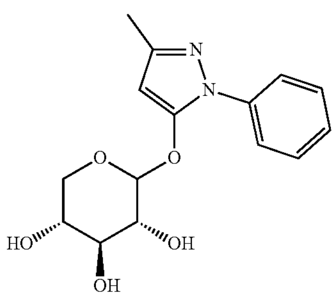 [SMILES: Cc1cc(OC2OC[C@@H](O)[C@H](O)[C@H]2O)n(-c2ccccc2)n1] | 307.18 | C, 58.81; H, 5.96; N, 9.13 |
| 39 | 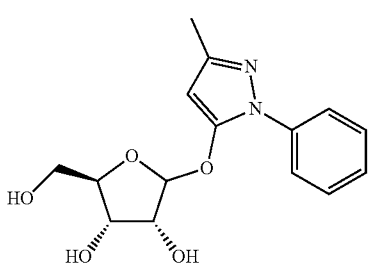 [SMILES: Cc1cc(OC2O[C@H](CO)[C@@H](O)[C@H]2O)n(-c2ccccc2)n1] | 307.04 | C, 58.80; H, 5.90; N, 9.17 |
| 40 | 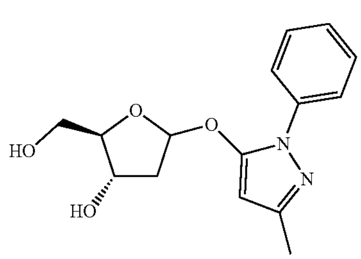 [SMILES: Cc1cc(OC2C[C@H](O)[C@@H](CO)O2)n(-c2ccccc2)n1] | 291.17 | C, 62.04; H, 6.23; N, 9.67 |

TABLE 1-continued

| No. | Structure | ESI-MS(m/z): [M]+ | Element analysis |
|---|---|---|---|
| 41 | 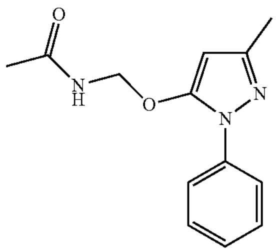 [SMILES: CC(=O)NCOc1cc(C)nn1-c1ccccc1] | 246.10 | C, 63.63; H, 6.20; N, 17.12 |
| 42 | 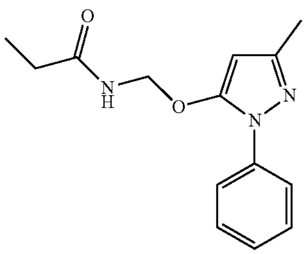 [SMILES: CCC(=O)NCOc1cc(C)nn1-c1ccccc1] | 260.17 | C, 64.81; H, 6.68; N, 16.19 |
| 43 | 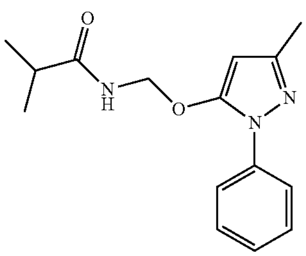 [SMILES: Cc1cc(OCNC(=O)C(C)C)n(-c2ccccc2)n1] | 274.16 | C, 65.90; H, 7.10; N, 15.34 |
| 44 | 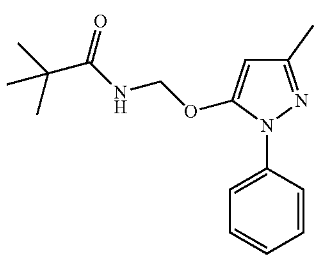 [SMILES: Cc1cc(OCNC(=O)C(C)(C)C)n(-c2ccccc2)n1] | 288.12 | C, 66.81; H, 7.42; N, 14.59 |
| 45 | 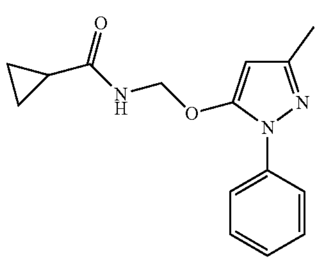 [SMILES: Cc1cc(OCNC(=O)C2CC2)n(-c2ccccc2)n1] | 272.15 | C, 66.42; H, 6.35; N, 15.43 |
| 46 | 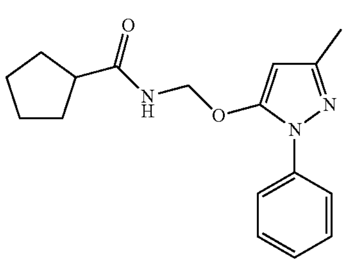 [SMILES: Cc1cc(OCNC(=O)C2CCCC2)n(-c2ccccc2)n1] | 300.23 | C, 68.22; H, 7.12; N, 14.01 |

TABLE 1-continued
| No. | Structure | ESI-MS(m/z): [M]⁺ | Element analysis |
|---|---|---|---|
| 47 | 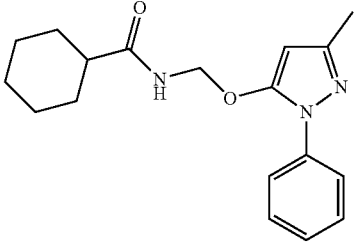 [SMILES: Cc1cc(OCNC(=O)C2CCCCC2)n(-c2ccccc2)n1] | 314.24 | C, 68.95; H, 7.48; N, 13.37 |
| 48 | 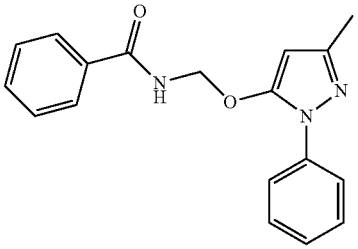 [SMILES: Cc1cc(OCNC(=O)c2ccccc2)n(-c2ccccc2)n1] | 308.16 | C, 70.31; H, 5.60; N, 13.63 |
| 49 | 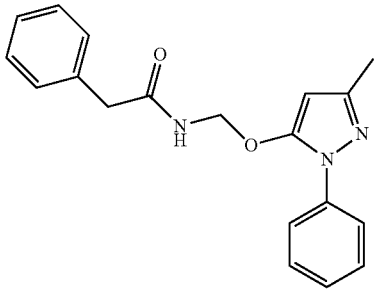 [SMILES: Cc1cc(OCNC(=O)Cc2ccccc2)n(-c2ccccc2)n1] | 322.20 | C, 71.05; H, 5.99; N, 13.04 |
| 50 | 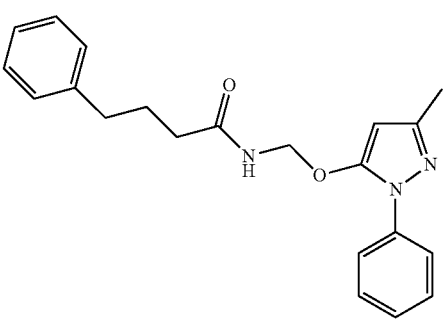 [SMILES: Cc1cc(OCNC(=O)CCCc2ccccc2)n(-c2ccccc2)n1] | 350.11 | C, 72.20; H, 6.68; N, 12.01 |
| 51 | 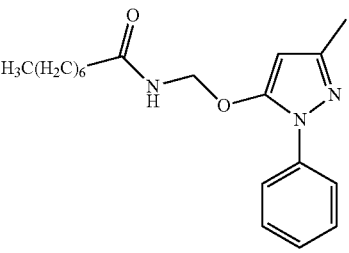 | 330.18 | C, 69.24; H, 8.33; N, 12.74 |

TABLE 1-continued

| No. | Structure | ESI-MS(m/z): [M]+ | Element analysis |
|---|---|---|---|
| 52 | H₃C(H₂C)₁₆—C(=O)—NH—CH₂—O—(3-methyl-1-phenylpyrazol-5-yl) | 470.30 | C, 74.11; H, 10.14; N, 8.90 |

Acronyms

TBTU: O-(Benzotriazol-1-yl)-N,N,N',N'-tetramethyluronium tetrafluoroborate
DMF: N,N-Dimethylformamide
ED: Edaravone
DBU: 1,8-Diazabicyclo [5.4.0] undec-7-ene
TMSOTf: Trimethylsilyl trifluoromethanesulfonate;
SOD: Superoxide Dismutase
MCAO: Middle Cerebral Artery Occlusion
ALS: Amyotrophic Lateral Sclerosis

EXAMPLES

Examples 1-12

Synthetic Route 1:

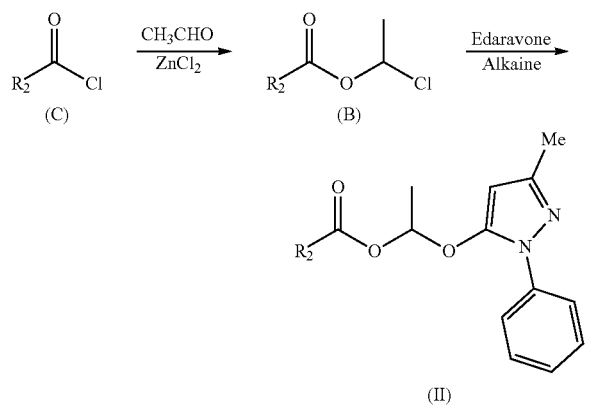

The starting material acyl chloride compounds can be obtained from its related carboxylic compounds shown as follows:

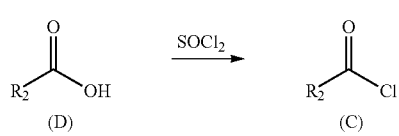

The general synthetic route 1 is:

Step 1: anhydrous acetaldehyde with a catalytic amount of anhydrous zinc chloride were dissolved in dry dichloromethane (10 mL) at 0° C., then followed by slow dropping of compound (C). After the dropping, the mix was heated to 50° C. and reacted for 2.5 h. When the reaction completed, the mix was added with 100 mL dichloromethane and then washed with saturated solution of sodium bicarbonate (1×50 mL), and the aqueous phase was extracted with dichloromethane (2×25 mL), and the organic phases were combined and sequentially washed with distilled water and saturated solution of sodium chloride, then dried with anhydrous sodium sulfate and concentrated under reduced pressure, and the crude product was purified by silica gel column chromatography to obtain compound (B).

Step 2: Edaravone (3.6 mmol), potassium iodide (0.4 mmol), and potassium carbonate (10 mmol) were dissolved in dry DMF (10 mL) and stirred for 10 min at 45° C. Then compound (B) (3.3 mmol) dissolved in dry DMF was added and stirred for 1 h at 45° C. When the reaction completed, most of the solvent was removed with an oil pump, and the remaining mix was added with 100 mL ethyl acetate and then washed with saturated solution of ammonium chloride. The aqueous phase was extracted twice with ethyl acetate, and the organic phases were combined and sequentially washed with distilled water, saturated solution of sodium chloride, then dried with anhydrous sodium sulfate and concentrated under reduced pressure, and the crude product obtained was separated by semi-preparative high-pressure liquid chromatography and lyophilized using a freeze dryer to obtain the target product compound (II).

Acryl chloride compound preparation: Dichlorosulfoxide was slowly added dropwise to compound (D) at 0° C. and refluxed at 80° C. for 2 h. When the reaction completed, the remaining thionyl chloride in the mix was pumped out and the residue was dissolved in an appropriate amount of dry dichloromethane and used directly in the next step.

Example 3: Preparation of 1-(3-methyl-1-phenylpyrazole) oxyethyl isobutyrate

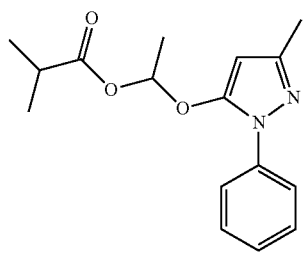 [SMILES: Cc1cc(OC(C)OC(=O)C(C)C)n(-c2ccccc2)n1]

The compound was prepared by the general synthetic route 1 as yellow oily liquid and the yield was 31.17%.

¹H NMR (400 MHz, CDCl₃) δ 7.68-7.62 (m, 2H), 7.41 (t, J=7.9 Hz, 2H), 7.29-7.23 (m, 1H), 6.46 (q, J=5.3 Hz, 1H), 5.58 (s, 1H), 2.53 (dt, J=14.0, 7.0 Hz, 1H), 2.26 (s, 3H), 1.59 (d, J=5.3 Hz, 3H), 1.14 (dd, J=9.4, 7.0 Hz, 6H).

ESI-MS (m/z): [M]⁺ 289.20

Example 4: Preparation of 1-(3-methyl-1-phenylpyrazole) oxyethyl pivalate

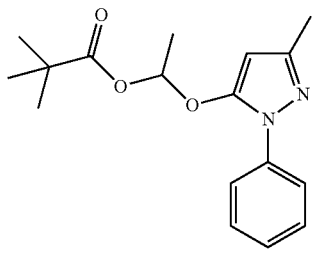 [SMILES: Cc1cc(OC(C)OC(=O)C(C)(C)C)n(-c2ccccc2)n1]

The compound was prepared by the general synthetic route 1 as white solid and the yield was 34.28%.

¹H NMR (400 MHz, CDCl₃) δ 7.65 (d, J=7.6 Hz, 2H), 7.41 (t, J=7.9 Hz, 2H), 7.33-7.19 (m, 1H), 6.45 (q, J=5.3 Hz, 1H), 5.57 (s, 1H), 2.26 (s, 3H), 1.58 (d, J=5.3 Hz, 3H), 1.16 (s, 9H).

ESI-MS (m/z): [M]⁺ 303.30

Example 5: Preparation of 1-(3-methyl-1-phenylpyrazole)oxyethyl octanoate

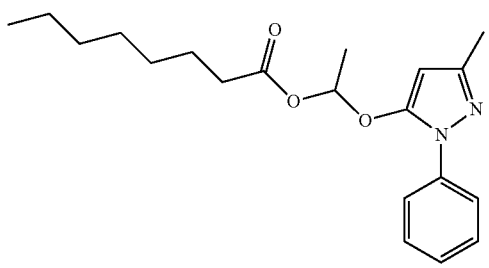 [SMILES: CCCCCCCC(=O)OC(C)Oc1cc(C)nn1-c1ccccc1]

The compound was prepared by the general synthetic route 1 as yellow oily liquid and the yield was 28.94%.

¹H NMR (400 MHz, CDCl₃) δ 7.64 (d, J=7.7 Hz, 2H), 7.30-7.22 (m, 2H), 7.25 (d, J=8.8 Hz, 1H), 6.47 (q, J=5.3 Hz, 1H), 5.59 (s, 1H), 2.33-2.24 (m, 5H), 1.64-1.54 (m, 5H), 1.33-1.21 (m, 8H), 0.92-0.84 (m, 3H).

ESI-MS (m/z): [M]⁺ 345.19

Example 7: Preparation of 1-(3-methyl-1-phenylpyrazole) oxyethyl benzoate

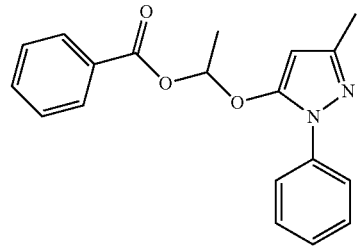 [SMILES: Cc1cc(OC(C)OC(=O)c2ccccc2)n(-c2ccccc2)n1]

The compound was prepared by the general synthetic route 1 as yellow oily liquid and the yield was 33.26%.

¹H NMR (400 MHz, CDCl₃) δ 8.02-7.98 (m, 2H), 7.69-7.65 (m, 2H), 7.62-7.56 (m, 1H), 7.47-7.36 (m, 4H), 7.29-7.24 (m, 1H), 6.69 (q, J=5.3 Hz, 1H), 5.65 (s, 1H), 2.23 (s, 3H), 1.72 (d, J=5.3 Hz, 3H).

ESI-MS (m/z): [M]⁺ 323.19

Example 9: Preparation of 1-(3-methyl-1-phenylpyrazole)oxyethyl phenylbutyrate

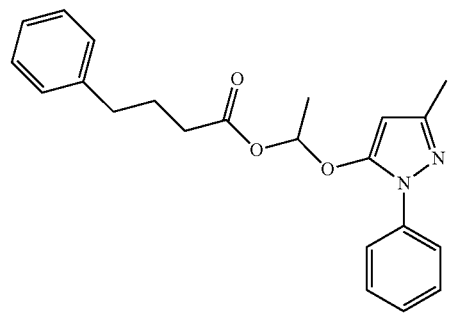 [SMILES: Cc1cc(OC(C)OC(=O)CCCc2ccccc2)n(-c2ccccc2)n1]

The compound was prepared by the general synthetic route 1 as yellow oily liquid and the yield was 29.87%.

¹H NMR (400 MHz, CDCl₃) δ 7.67-7.61 (m, 1H), 7.40 (t, J=7.9 Hz, 2H), 7.30-7.11 (m, 7H), 6.48 (q, J=5.3 Hz, 1H), 5.60 (s, 1H), 2.61 (t, J=7.5 Hz, 2H), 2.31 (t, J=7.4 Hz, 2H), 2.25 (s, 3H), 1.95-1.88 (m, 2H), 1.58 (d, J=5.3 Hz, 3H).

ESI-MS (m/z): [M]⁺ 365.25

Examples 1, 2, 6, 8, 10, 11 and 12

Compounds 1, 2, 6, 8, 10, 11 and 12 were synthesized by general synthetic route 1.

Examples 13-32

Synthetic Route 2:

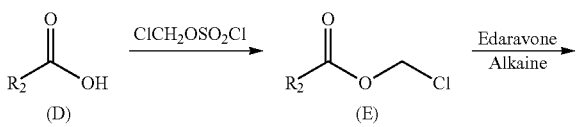

43
-continued

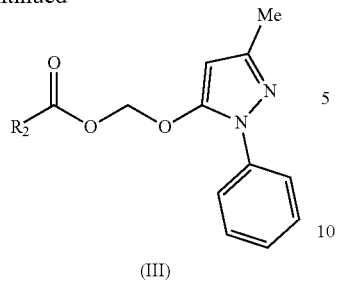

(III)

General Synthetic Route 2:

Step 1.

Compound (D) (5.68 mmol) was dissolved in a mixture of dichloromethane (15 mL) and water (17 mL) at room temperature, followed by slow addition of sodium bicarbonate (28.45 mmol) and tetrabutylammonium bisulfate (0.56 mmol) under vigorous stirring, followed by the dropwise addition of chloromethyl chlorosulfate (8.5 mmol) at 0° C. and stirred at room temperature for 24 h. When the reaction completed, the mix was added with 100 mL ethyl acetate and then washed with saturated solution of ammonium chloride. The aqueous phase was extracted with ethyl acetate, and the organic phases were combined and sequentially washed with distilled water and saturated solution of sodium chloride, then dried with anhydrous sodium sulfate, concentrated under reduced pressure and purified by silica gel column chromatography to obtain compound (E).

Step 2.

Edaravone (2.93 mmol), potassium carbonate (8.84 mmol), and potassium iodide (3.55 mmol) were dissolved in dry DMF (6.00 mL) and stirred for 20 min at 50° C. Compound (E) (2.94 mmol) obtained in the step 1 was dissolved in dry DMF (2.50 mL) and added to the above mix. When the reaction completed, the mix was added with 100 mL ethyl acetate (or dichloromethane), then washed with saturated solution of ammonium chloride, and the aqueous phase was extracted with ethyl acetate (or dichloromethane) and the organic phases were combined and sequentially washed with distilled water, saturated solution of sodium chloride so, then dried with anhydrous sodium sulfate, concentrated under reduced pressure, and purified by silica gel column chromatography to obtain the target compound (III).

Example 13: Preparation of (3-methyl-1-phenylpyrazol-5-) oxymethyl pivalate

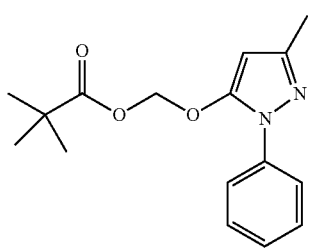 [SMILES: Cc1cc(OCOC(=O)C(C)(C)C)n(-c2ccccc2)n1]

The compound was prepared by the general synthetic route 2 as yellow oily liquid and the yield was 54.64%.

$^1$H NMR (600 MHz, CDCl$_3$) δ 7.63 (d, J=7.7 Hz, 2H), 7.40 (t, J=7.9 Hz, 2H), 7.29-7.22 (m, 1H), 5.74-5.68 (m, 3H), 2.29 (s, 3H), 1.20 (s, 9H).

ESI-MS (m/z): [M]$^+$ 289.22

44
Example 14: Preparation of (3-methyl-1-phenylpyrazol-5-) oxymethyl isobutyrate

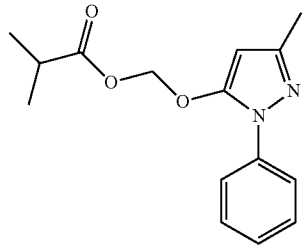 [SMILES: Cc1cc(OCOC(=O)C(C)C)n(-c2ccccc2)n1]

The compound was prepared by the general synthetic route 2 as yellow oily liquid and the yield was 53.37%.

$^1$H NMR (400 MHz, CDCl$_3$) δ 7.63 (d, J=7.7 Hz, 2H), 7.40 (t, J=7.9 Hz, 2H), 7.29-7.22 (m, 1H), 5.71 (d, J=1.9 Hz, 3H), 2.58 (dt, J=14.0, 7.0 Hz, 1H), 2.29 (s, 3H), 1.17 (d, J=7.0 Hz, 6H).

ESI-MS (m/z): [M]$^+$ 275.18

Example 15: Preparation of (3-methyl-1-phenylpyrazol-5-) oxymethyl octanoate

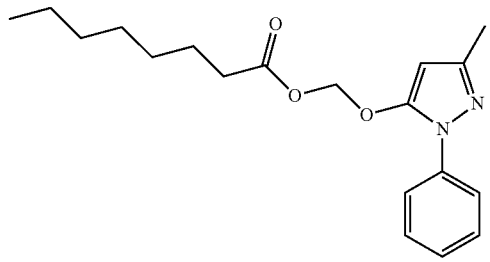 [SMILES: CCCCCCCC(=O)OCOc1cc(C)nn1-c1ccccc1]

The compound was prepared by the general synthetic route 2 as yellow oily liquid and the yield was 60.28%.

$^1$H NMR (400 MHz, CDCl$_3$) δ 7.63 (d, J=7.9 Hz, 2H), 7.40 (t, J=7.9 Hz, 2H), 7.28-7.21 (m, 1H), 5.70 (s, 3H), 2.36-2.26 (m, 5H), 1.66-1.55 (m, 2H), 1.27 (s, 8H), 0.87 (t, J=6.7 Hz, 3H).

ESI-MS (m/z): [M]$^+$ 331.24

Example 16: Preparation of (3-methyl-1-phenylpyrazol-5-) oxymethyl phenylbutyrate

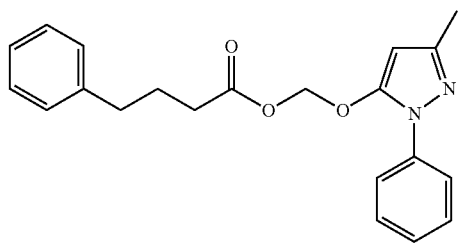 [SMILES: Cc1cc(OCOC(=O)CCCc2ccccc2)n(-c2ccccc2)n1]

The compound was prepared by the general synthetic route 2 as yellow oily liquid (1.20 g) and the yield was 59.74%.

$^1$H NMR (400 MHz, CDCl$_3$) δ 7.62 (d, J=7.9 Hz, 2H), 7.39 (t, J=7.9 Hz, 2H), 7.30-7.11 (m, 6H), 5.69 (s, 3H), 2.62 (t, J=7.6 Hz, 2H), 2.34 (t, J=7.4 Hz, 2H), 2.28 (s, 3H), 1.99-1.89 (m, 2H).

ESI-MS (m/z): [M]$^+$ 351.13

Example 17: Preparation of (3-methyl-1-phenylpyrazol-5-) oxymethyl nicotinate

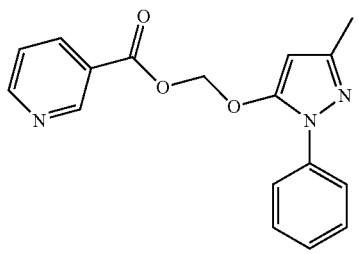 [SMILES: Cc1cc(OCOC(=O)c2cccnc2)n(-c2ccccc2)n1]

The compound was prepared by the general synthetic route 2 as yellow solid (0.62 g) and the yield was 43.28%.

$^1$H NMR (400 MHz, CDCl$_3$) δ 9.22 (s, 1H), 8.84 (d, J=4.3 Hz, 1H), 8.34 (d, J=8.0 Hz, 1H), 7.64-7.59 (m, 2H), 7.51-7.45 (m, 1H), 7.38 (t, J=7.9 Hz, 2H), 7.25-7.20 (m, 1H), 5.98 (s, 2H), 5.82 (s, 1H), 2.31 (s, 3H).

ESI-MS (m/z): [M]$^+$ 310.15

Example 18: Preparation of (3-methyl-1-phenylpyrazol-5-) oxymethyl benzoate

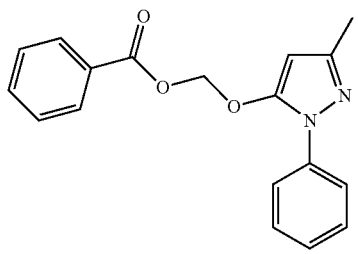 [SMILES: Cc1cc(OCOC(=O)c2ccccc2)n(-c2ccccc2)n1]

The compound was prepared by the general synthetic route 2 as yellow oily liquid (0.99 g) and the yield was 56.21%.

$^1$H NMR (400 MHz, CDCl$_3$) δ 8.08-8.02 (m, 2H), 7.68-7.57 (m, 3H), 7.50-7.34 (m, 4H), 7.25-7.20 (m, 1H), 5.96 (s, 2H), 5.81 (s, 1H), 2.30 (s, 3H).

ESI-MS (m/z): [M]$^+$ 309.17

Example 19: Preparation of (3-methyl-1-phenylpyrazol-5-) oxymethyl-(2-hydroxy) benzoate

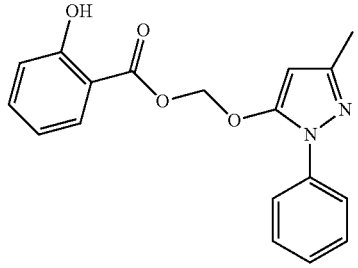 [SMILES: Cc1cc(OCOC(=O)c2ccccc2O)n(-c2ccccc2)n1]

(1) Preparation of (3-methyl-1-phenylpyrazole-5-) oxymethyl-(2-benzyloxy) benzoate

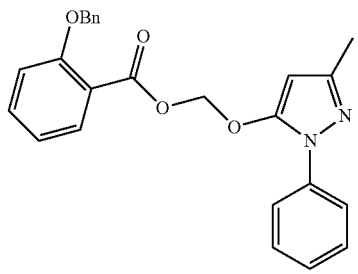 [SMILES: Cc1cc(OCOC(=O)c2ccccc2OCc2ccccc2)n(-c2ccccc2)n1]

The compound was prepared by the general synthetic route 2 as yellow solid (0.37 g) and the yield was 48.93%.

(2) Preparation of (3-methyl-1-phenylpyrazole-5-) oxymethyl-(2-hydroxy) benzoate

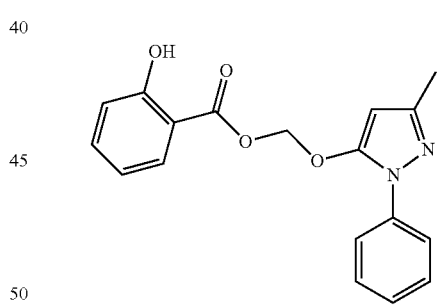

(3-Methyl-1-phenylpyrazole-5-) oxymethyl-(2-benzyloxy) benzoate (0.37 g) was dissolved in 5 mL methanol, followed by addition of 1% catalytic amount of 10% palladium/carbon, stirring at room temperature under hydrogen for 1.5 h. When the reaction completed, the mix was filtered with diatomaceous earth, and the solvent was removed with a rotary evaporator, and the resulting oily liquid was purified by silica gel column chromatography (petroleum ether/Ethyl acetate: 10/1) to obtain 0.24 g of yellow oily liquid with a yield of 82.70%.

$^1$H NMR (400 MHz, CDCl$_3$) δ 10.36 (s, 1H), 7.79 (dd, J=8.0, 1.5 Hz, 1H), 7.61 (d, J=7.6 Hz, 2H), 7.52-7.46 (m, 1H), 7.38 (t, J=7.9 Hz, 2H), 7.27-7.206 (m, 1H), 7.04-6.95 (m, 1H), 6.95-6.86 (m, 1H), 5.95 (s, 2H), 5.80 (s, 1H), 2.30 (s, 3H).

ESI-MS (m/z): [M]$^+$ 325.01

Example 20: Preparation of (3-methyl-1-phenylpyrazole-5-)oxymethyl acetylsalicylate

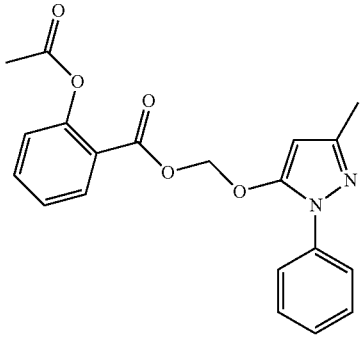 [SMILES: CC(=O)Oc1ccccc1C(=O)OCOc1cc(C)nn1-c1ccccc1]

The compound was prepared by the general synthetic route 2 as light yellow solid (0.48 g) and the yield was 59.78%.

$^1$H NMR (600 MHz, CDCl$_3$) δ 7.99 (d, J=7.8 Hz, 1H), 7.65-7.57 (m, 3H), 7.40 (t, J=7.9 Hz, 2H), 7.33 (t, J=7.6 Hz, 1H), 7.28-7.22 (m, 1H), 7.13 (d, J=8.1 Hz, 1H), 5.90 (s, 2H), 5.77 (s, 1H), 2.30 (s, 6H).

ESI-MS (m/z): [M]$^+$ 367.18

Example 21: Preparation of (3-methyl-1-phenylpyrazole-5-) oxymethyl-(2-ethoxycarbonyloxy) benzoate

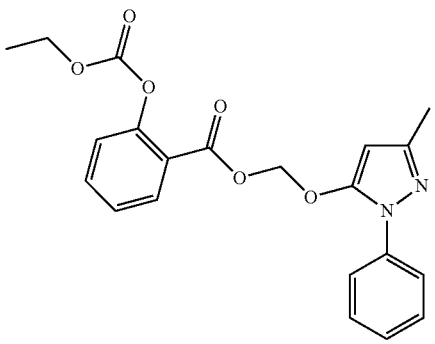 [SMILES: CCOC(=O)Oc1ccccc1C(=O)OCOc1cc(C)nn1-c1ccccc1]

The product of Example 19 (0.50 g) was dissolved in dry dichloromethane (5 mL) at room temperature, followed by addition of dry triethylamine (0.47 mL), and then slow addition of ethyl chloroformate (0.35 mL), stirring at room temperature for 2.5 h. When the reaction completed, the mix was added with 100 ml dichloromethane and washed with saturated solution of ammonium chloride (1*50 mL). The aqueous phase was extracted with dichloromethane (2*25 mL), and the organic phases were combined and sequentially washed with saturated solution of ammonium chloride, distilled water and saturated solution of sodium chloride, then dried with anhydrous sodium sulfate, and the solvent was removed by a rotary evaporator, the resulting oily liquid was purified by silica gel column chromatography (petroleum ether/ethyl acetate: 3/1) to obtain 0.54 g of light yellow oily liquid with a yield of 88.14%.

$^1$H NMR (400 MHz, CDCl$_3$) δ 8.00 (dd, J=7.9, J=1.6 Hz, 1H), 7.66-7.58 (m, 3H), 7.43-7.32 (m, 3H), 7.27-7.21 (m, 2H), 5.91 (s, 2H), 5.80 (s, 1H), 4.28 (q, J=7.1 Hz, 2H), 2.29 (s, 3H), 1.36 (t, J=7.1 Hz, 3H).

ESI-MS (m/z): [M]$^+$ 397.18

Example 22: Preparation of (3-methyl-1-phenylpyrazol-5-)oxymethyl-(2-isobutyryloxy)benzoic acid

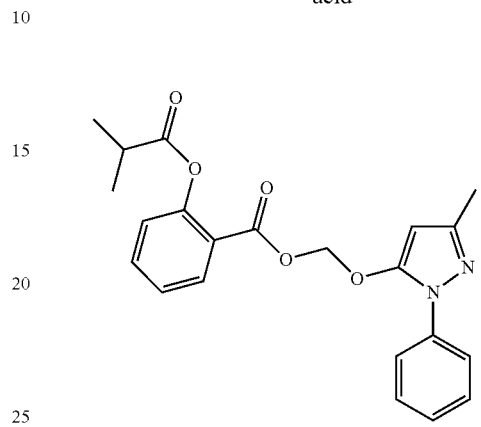

The product of Example 19 (0.50 g) was dissolved in dry dichloromethane (5 mL) at room temperature, followed by addition of dry triethylamine (0.39 mL), and then slow addition of isobutyryl chloride (0.32 mL), stirring at room temperature for 2.5 h. When the reaction completed, the mix was added with 100 ml dichloromethane and washed with saturated solution of ammonium chloride. The aqueous phase was extracted with dichloromethane, and the organic phases were combined and sequentially washed with saturated solution of ammonium chloride, distilled water and saturated solution of sodium chloride, dried with anhydrous sodium sulfate, concentrated under reduced pressure, and the resulting oily liquid was purified by silica gel column chromatography (petroleum ether/ethyl acetate: 3/1) to obtain 0.48 g of light-yellow oily liquid with a yield of 79.48%.

$^1$H NMR (400 MHz, CDCl$_3$) δ 8.00-7.93 (m, 1H), 7.65-7.56 (m, 3H), 7.39 (t, J=7.8 Hz, 2H), 7.31 (t, J=7.6 Hz, 1H), 7.29-7.20 (m, 1H), 7.10 (d, J=8.1 Hz, 1H), 5.89 (s, 2H), 5.77 (s, 1H), 2.84 (dt, J=14.0 Hz, J=7.0 Hz, 1H), 2.29 (s, 3H), 1.32 (d, J=7.0 Hz, 6H).

ESI-MS (m/z): [M]$^+$ 395.21

Example 23: Preparation of (3-methyl-1-phenylpyrazol-5-) oxymethyl-(2-hydroxy-3-N,N-dimethyl)benzoate

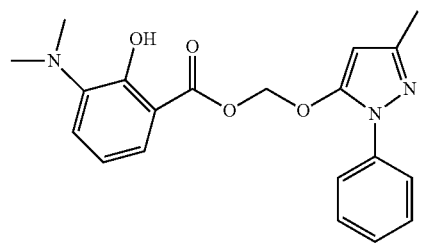

(1) Preparation of methyl 3-amino 2-hydroxybenzoate

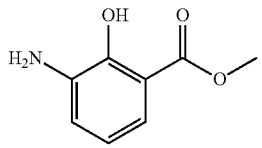

2-Hydroxy-3-aminobenzoic acid (8.0 g) was added to anhydrous methanol (80 mL), followed by slow addition of dichlorosulfoxide (15 mL) at 0° C., and the reaction was carried out at 60° C. for 24 h. When the reaction completed, the solvent was removed under reduced pressure, and the pH was adjusted to neutral with sodium bicarbonate solution, and then the mix was added with 100 mL dichloromethane for extraction, dried with anhydrous sodium sulfate, concentrated under reduced pressure, and purified by silica gel column chromatography, so as to obtain 7.4 g of solid product with a yield of 85.1%.

(2) Preparation of methyl 3-N,N-dimethyl 2-hydroxy benzoate

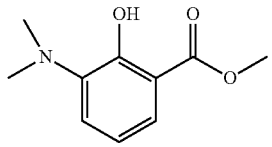

Methyl 2-hydroxy-3-amino benzoate (2.0 g) was dissolved in methanol (30 mL) at room temperature, followed by addition of formaldehyde solution (6 mL), and then acetic acid (0.5 mL), and then slow addition of sodium cyanoborohydride (3.72 g) at low temperature, which then reacted at room temperature for 2 h. When the reaction completed, the solvent was removed and the mix was concentrated with a rotary evaporator, and the remaining product dissolved in ethyl acetate (150 mL) and was washed with water, dried with anhydrous sodium sulfate, and concentrated under reduced pressure to obtain 2.1 g of product with a yield of 85.8%.

(3) Preparation of methyl 3-N,N-dimethyl-2-benzyloxy benzoate

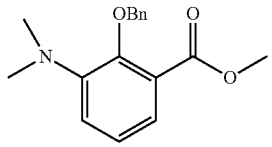

Methyl 2-hydroxy-3-N,N-dimethylbenzoate (2.0 g) was dissolved in dry DMF (7.5 mL). The mix was added with potassium carbonate (4.25 g), then benzyl bromide (1.83 mL) at room temperature, and reacted at 90° C. for 3 h. When the reaction completed, a large amount of solvent was removed with an oil pump, and then the remaining product was added with 100 ml ethyl acetate and washed with saturated solution of ammonium chloride (50 ml). The aqueous phase was extracted with ethyl acetate (2*25 mL), and the organic phases were combined and sequentially washed with saturated solution of ammonium chloride, distilled water and saturated solution of sodium chloride, then dried with anhydrous sodium sulfate and the solvent was removed with a rotary evaporator, and the resulting oily liquid was purified by silica gel column chromatography (petroleum ether/ethyl acetate: 15/1) to obtain 2.84 g of product with a yield of 45.55%.

(4) Preparation of 3-N,N-dimethyl-2-benzyloxy benzoic acid

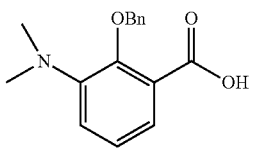 [SMILES: CN(C)c1cccc(C(=O)O)c1OCc1ccccc1]

Methyl 2-benzyloxy-3-N,N-dimethylbenzoate (2.0 g) was dissolved in methanol (12 mL), followed by addition of 1N sodium hydroxide (1 mol/L) solution (24 mL), and the reaction was carried out at 80° C. for 2 h. When the reaction completed, the remaining methanol solvent was removed by a rotary evaporator and the pH was adjusted with hydrochloric acid until precipitation appeared. Appropriate amount of distilled water was added to the mix which was then extracted with dichloromethane until no target product existed in the aqueous phase. The organic phase was dried under reduced pressure as a yellow solid of 1.67 g, and the yield was 87.72%.

(5) Preparation of chloromethyl 3-N,N-dimethyl-2-benzyloxy benzoate

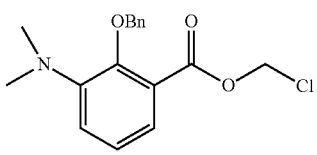 [SMILES: CN(C)c1cccc(C(=O)OCCl)c1OCc1ccccc1]

2-Benzyloxy-3-N,N-dimethylbenzoic acid (1.0 g) was dissolved in a mixture of dichloromethane (5 mL) and water (10 mL) at room temperature, and sodium bicarbonate (1.24 g) and tetrabutylammonium bromide (0.11 g) were added slowly with vigorous stirring, and then chloromethyl chlorosulfate (0.73 mL) dissolved in 5 mL of dry dichloromethane was added dropwise at 0° C. and stirred for 24 h at room temperature. When the reaction completed, the mix was added with 100 ml dichloromethane and then washed with saturated solution of sodium bicarbonate (50 mL). The aqueous phase was extracted with dichloromethane (2*25 mL), and the organic phases were combined and sequentially washed with saturated solution of sodium bicarbonate, distilled water and saturated solution of sodium chloride, then dried with anhydrous sodium sulfate and the solvent was removed with a rotary evaporator, and the resulting oily liquid was purified by silica gel column chromatography (petroleum ether/ethyl acetate: 15/1) to obtain 0.55 g of product with a yield of 46.31%.

(6) Preparation of (3-methyl-1-phenylpyrazole-5-)oxymethyl-(3-N,N-dimethyl-2-benzyloxy) benzoate

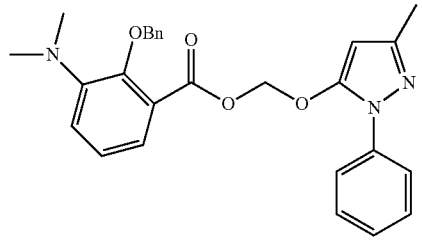

Edaravone (0.24 g), potassium carbonate (0.71 g), and potassium iodide (0.34 g) were dissolved in dry DMF (6.00 mL) and stirred for 20 min at 50° C. Chloromethyl-(2-benzyloxy-3-N,N-dimethyl)benzoate (0.55 g) was dissolved in dry DMF (2.50 mL) and added to the above solution and stirred for 3 h at 45° C. When the reaction completed, the mix was added with 100 ml ethyl acetate and then washed with saturated solution of ammonium chloride (1*50 ml). The aqueous phase was extracted with ethyl acetate (2*25 ml), and the organic phases were combined and sequentially washed with saturated solution of ammonium chloride, distilled water and saturated solution of sodium chloride, then dried with anhydrous sodium sulfate and the solvent was removed with a rotary evaporator, and the resulting oily liquid was purified by silica gel column chromatography (petroleum ether/ethyl acetate: 15/1) to obtain 0.22 g of product with a yield of 27.87%.

(7) Preparation of (3-methyl-1-phenylpyrazole-5-)oxymethyl-(3-N,N-dimethyl-2-hydroxy) benzoate

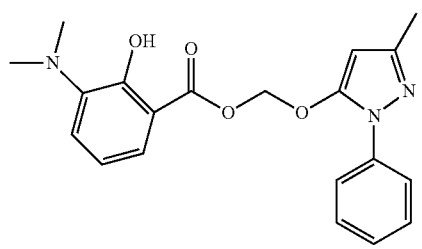

The (3-methyl-1-phenylpyrazole)oxymethyl-(2-benzyloxy-3-N,N-dimethyl) benzoate (0.22 g) was dissolved in 5 mL ethyl acetate, and a catalytic amount (1%) of palladium/carbon (10%) was added and stirred at room temperature under hydrogen for 1.5 h. When the reaction completed, the reaction solution was filtered through diatomaceous earth and concentrated under reduced pressure. The crude product was purified by silica gel column chromatography (petroleum ether/ethyl acetate: 5/1) to obtain a yellow solid of 0.17 g with a yield of 79.26%.

$^1$H NMR (400 MHz, CDCl$_3$) δ 9.83 (s, 1H), 7.62 (d, J=7.7 Hz, 2H), 7.38 (t, J=7.9 Hz, 2H), 7.28-7.19 (m, 1H), 7.16-7.04 (m, 2H), 6.92 (d, J=9.0 Hz, 1H), 5.96 (s, 2H), 5.81 (s, 1H), 2.88 (s, 6H), 2.29 (s, 3H).

ESI-MS (m/z): [M]$^+$ 368.19

Example 24: Preparation of (3-methyl-1-phenylpyrazole-5-)oxymethyl-(2-hydroxy-5-N,N-dimethyl)benzoate

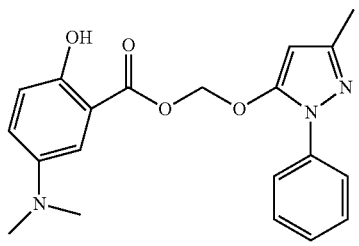 [SMILES: Cc1cc(OCOC(=O)c2cc(N(C)C)ccc2O)n(-c2ccccc2)n1]

(1) Preparation of methyl 2-hydroxy-5-aminobenzoate

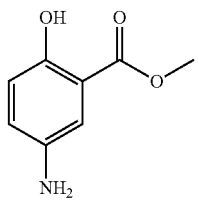

P-aminosalicylic acid (8.0 g) was added to anhydrous methanol (80 mL), and dichlorosulfoxide (15 mL) was slowly added at 0° C. for 24 h. When the reaction completed, the remaining methanol was removed with a rotary evaporator, and the pH was adjusted to neutral with sodium bicarbonate solution, and then 100 mL of dichloromethane was added for extraction, dried with anhydrous sodium sulfate, and concentrated under reduced pressure. 7.50 g of solid product was obtained with a yield of 85.91%.

(2) Preparation of methyl 2-hydroxy-5-N,N-dimethylbenzoate

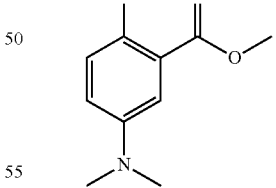

Methyl 2-hydroxy-5-aminobenzoate (2.0 g) was dissolved in methanol (30 mL) at room temperature, to which 40% aqueous formaldehyde solution (6 mL) was added, then acetic acid (0.5 mL) was added, and sodium cyanoborohydride (3.72 g) was slowly added at low temperature, and the reaction was carried out at room temperature for 2 h. When the reaction completed, the remaining methanol solvent was removed with a rotary evaporator, and the remaining mix was dissolved into 150 mL ethyl acetate, washed with distilled water, dried with anhydrous sodium sulfate, and concentrated under reduced pressure to obtain 2.0 g of the product with a yield of 85.47%.

(3) Preparation of methyl 2-(benzyloxy)-5-N,N-dimethylbenzoate

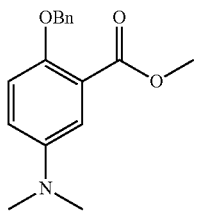 [SMILES: COC(=O)c1cc(N(C)C)ccc1OCc1ccccc1]

Methyl 2-hydroxy-5-N,N-dimethylbenzoate (2.0 g) was dissolved in dry DMF (7.5 mL), potassium carbonate (4.25 g) was added, benzyl bromide (1.83 mL) was added at room temperature, and the reaction was carried out at 90° C. for 3 h. When the reaction completed, a large amount of solvent was removed with an oil pump, and 100 mL of ethyl acetate was added to the reaction solution, which was then washed with saturated ammonium chloride solution. The aqueous phase was extracted with ethyl acetate (2*25 mL), and the organic phases were combined. The organic phases were washed with saturated aqueous ammonium chloride solution, distilled water, saturated sodium chloride solution, dried with anhydrous sodium sulfate, and the solvent was removed by a rotary evaporator, and the crude product was purified by silica gel column chromatography (petroleum ether/ethyl acetate: 15/1) to obtain 2.84 g of product with a yield of 45.55%.

(4) Preparation of 2-(benzyloxy)-5-N,N-dimethylbenzoic acid

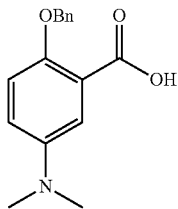 [SMILES: CN(C)c1ccc(OCc2ccccc2)c(C(=O)O)c1]

Methyl 2-benzyloxy-5-N,N-dimethylbenzoate (2.0 g) was dissolved in methanol (12 mL), followed by addition of sodium hydroxide solution (24 mL) to react at 80° C. for 2 h. When the reaction completed, the remaining methanol was removed by a rotary evaporator. The pH was adjusted with hydrochloric acid until the mix began to precipitate, followed by addition of an appropriate amount of distilled water, and then extracted with dichloromethane until the aqueous phase did not contain the target product. The organic phase was concentrated under reduced pressure to obtain 1.67 g of yellow solid with a yield of 87.72%.

(5) Preparation of chloromethyl-(2-benzyloxy-5-N,N-dimethyl)benzoate

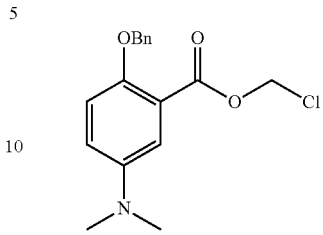

2-Benzyloxy-5-N,N-dimethylbenzoic acid (1.0 g) was dissolved in a mixture of dichloromethane (5 mL) and water (10 mL) at room temperature. Then sodium bicarbonate (1.24 g) and tetrabutylammonium bromide (0.11 g) were added slowly with vigorous stirring. And then chloromethyl chlorosulfate (0.73 mL) dissolved in 5 mL of dry dichloromethane was added dropwise at 0° C. When the reaction completed, 100 mL of dichloromethane was added to the reaction solution and then washed with saturated aqueous sodium bicarbonate (1*50 mL), the aqueous phase was extracted with dichloromethane (2*25 mL), and the organic phases were combined. The organic phases were sequentially washed with saturated aqueous sodium bicarbonate solution, distilled water, saturated sodium chloride solution, dried with anhydrous sodium sulfate, and the solvent was removed with a rotary evaporator, and the resulting oily liquid was purified by silica gel column chromatography (petroleum ether/ethyl acetate: 15/1) to obtain 0.55 g of a light-yellow solid with a yield of 46.31%.

(6) Preparation of (3-methyl-1-phenylpyrazole-5-) oxymethyl-(2-benzyloxy-5-N,N-dimethyl) benzoate

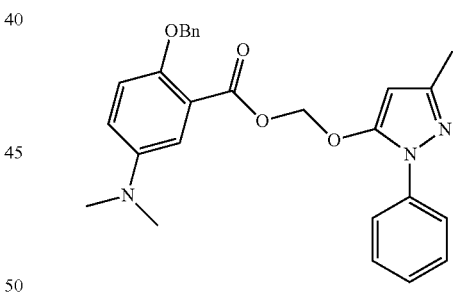

Edaravone (0.24 g), potassium carbonate (0.71 g), and potassium iodide (0.34 g) were dissolved in dry DMF (6 mL) and stirred for 20 min at 50° C. Chloromethyl-(2-benzyloxy-5-N,N-dimethyl)benzoate (0.55 g) was dissolved in dry DMF (2.5 mL) and added to the above solution and stirred at 45° C. for 3 h. When the reaction completed, 100 mL of ethyl acetate (1*50 mL) was added to the reaction solution and the aqueous phase was extracted with ethyl acetate (2*25 mL). When the reaction completed, 100 mL of ethyl acetate was added to the reaction solution, and then washed with saturated aqueous ammonium chloride (1*50 mL), and the aqueous phase was extracted with ethyl acetate (2*25 mL), and the organic phases were combined. The organic phases were sequentially washed with saturated aqueous ammonium chloride solution, distilled water, saturated sodium chloride solution, dried with anhydrous sodium sulfate, and the solvent was removed by a rotary evaporator, and the resulting oily liquid was purified by silica gel column chromatography (petroleum ether/ethyl acetate: 15/1) to obtain 0.22 g of product in 27.87% yield.

(7) Preparation of (3-methyl-1-phenylpyrazole-5-) oxymethyl-(2-hydroxy-5-N,N-dimethyl) benzoate

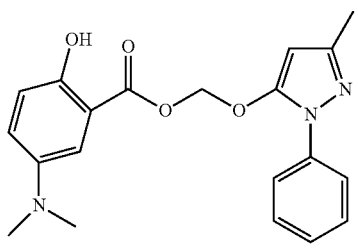 [SMILES: Cc1cc(OCOC(=O)c2cc(N(C)C)ccc2O)n(-c2ccccc2)n1]

(3-methyl-1-phenylpyrazole)oxymethyl-(2-benzyloxy-5-N,N-dimethyl)benzoate (0.22 g) was dissolved in 5 mL of ethyl acetate, and a catalytic amount of 10% palladium/carbon was added and stirred at room temperature under hydrogen for 1.5 h. When the reaction completed, the reaction solution was filtered through diatomaceous earth and the solvent was removed by a rotary evaporator, and the crude product obtained was purified by silica gel column chromatography (Petroleum ether/ethyl acetate: 5/1), so as to obtain 0.17 g of yellow solid in 79.26% yield.

$^1$H NMR (400 MHz, CDCl$_3$) δ 9.83 (s, 1H), 7.62 (d, J=7.7 Hz, 2H), 7.38 (t, J=7.9 Hz, 2H), 7.28-7.19 (m, 1H), 7.16-7.04 (m, 2H), 6.92 (d, J=9.0 Hz, 1H), 5.96 (s, 2H), 5.81 (s, 1H), 2.88 (s, 6H), 2.29 (s, 3H).

ESI-MS (m/z): [M]$^+$ 368.22

Example 25: Preparation of (3-methyl-1-phenylpyrazole-5-) oxymethyl-(2-ethoxycarbonyloxy-5-N,N-dimethyl)benzoic Acid

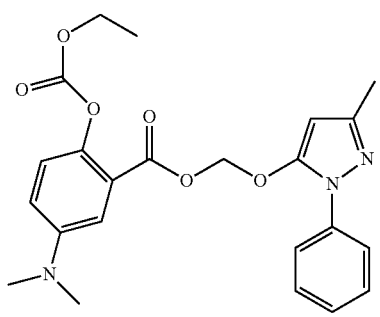

The product of Example 24 (0.1 g) was dissolved in dry dichloromethane (5 mL) at room temperature, dry triethylamine (0.1 mL) was added, and then ethyl chloroformate (0.08 mL) was slowly added and stirred at room temperature for 2.5 h. When the reaction completed, 100 mL of dichloromethane was added to the reaction solution and then washed with saturated aqueous ammonium chloride solution (1*50 mL). The aqueous phase was extracted with dichloromethane (2*25 mL) and the organic phases were combined. The organic phases were sequentially washed with saturated ammonium chloride solution, distilled water, saturated sodium chloride solution, dried with anhydrous sodium sulfate, and the solvent was removed by a rotary evaporator. The obtained oily liquid was purified by silica gel column chromatography (petroleum ether/ethyl acetate: 3/1) to prepare 0.11 g of light-yellow oily liquid with a yield of 85%.

$^1$H NMR (400 MHz, CDCl$_3$) δ7.62 (d, J=7.7 Hz, 2H), 7.38 (t, J=7.9 Hz, 2H), 7.28-7.19 (m, 1H), 7.16-7.04 (m, 2H), 6.92 (d, J=9.0 Hz, 1H), 5.96 (s, 2H), 5.81 (s, 1H), 4.21 (m, 2H), 1.29 (t, J=7.8 Hz, 3H), 2.88 (s, 6H), 2.29 (s, 3H).

ESI-MS (m/z): [M]$^+$ 440.21

Examples 26-32

Compounds 26-32 were prepared through the general synthetic route 2.

Example 33: Preparation of 1-phenyl-3-methyl-5-O-D-glucoside-pyrazole

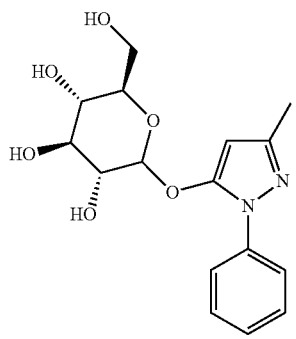 [SMILES: Cc1cc(OC2O[C@H](CO)[C@@H](O)[C@H](O)[C@H]2O)n(-c2ccccc2)n1]

Preparation Method 1:

(1) Preparation of 1,2,3,4,6-O-pentaacetyl-D-glucose

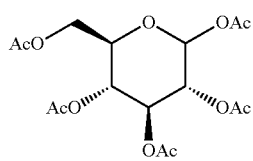 [SMILES: CC(=O)OC[C@H]1OC(OC(C)=O)[C@H](OC(C)=O)[C@@H](OC(C)=O)[C@@H]1OC(C)=O]

Glucose anhydrous (4.5 g) and potassium acetate (4.9 g) were dissolved in acetic anhydride (25 mL) at room temperature, and then stirred at 90° C. for 4 h. When the reaction completed, the temperature was lowered to room temperature, and the solvent was removed with an oil pump. The remaining mix was added with 100 mL ethyl acetate, then washed with saturated solution of sodium bicarbonate. The aqueous phase was extracted with ethyl acetate, and the organic phases were combined and sequentially washed with saturated solution of sodium bicarbonate, distilled water, and saturated solution of sodium chloride, then dried with anhydrous sodium sulfate and purified by silica gel column chromatography to obtain 6.3 g of product with a yield of 65%.

(2) Preparation of 2,3,4,6-tetra-O-acetyl-D-bromoglucose

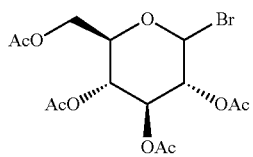 [SMILES: CC(=O)OC[C@H]1OC(Br)[C@H](OC(C)=O)[C@@H](OC(C)=O)[C@@H]1OC(C)=O]

1,2,3,4,6-O-pentaacetyl-D-glucose (2.5 g) was dissolved in dry dichloromethane (8 mL). 2.5 mL of 33% solution of hydrogen bromide dissolving in an appropriate amount of acetic acid was added to the above dichloromethane solution at 0° C., stirring at room temperature for 2 h until completed. The mix was added with 100 ml dichloromethane and then washed with saturated solution of sodium bicarbonate. The aqueous phase was extracted with dichloromethane, and the organic phases were combined and sequentially washed with sodium bicarbonate solution, distilled water and saturated solution of sodium chloride, then dried with anhydrous sodium sulfate and concentrated under reduced pressure, and the crude product was purified by silica gel column chromatography (petroleum ether/ethyl acetate: 3/1) to obtain 1.7 g of product with a yield of 64.6%.

(3) Preparation of 1-phenyl-3-methyl-5-O-(2,3,4,6-tetra-O-acetyl-D-glucoside) pyrazole

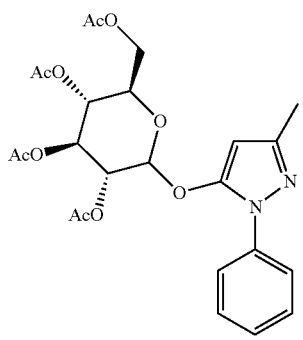 [SMILES: CC(=O)OC[C@H]1OC(Oc2cc(C)nn2-c2ccccc2)[C@H](OC(C)=O)[C@@H](OC(C)=O)[C@@H]1OC(C)=O]

Edaravone (0.35 g) and cesium carbonate (0.79 g) were dissolved in dry DMF (10 mL) and stirred for 20 min at room temperature. 2,3,4,6-Tetra-O-acetyl-D-bromoglucose (1.0 g) was then added and stirred at room temperature for 24 h. When the reaction completed, a large amount of solvent was removed with an oil pump, and then remaining mix was added with 100 mL ethyl acetate and washed with saturated solution of ammonium chloride. The aqueous phase was extracted with ethyl acetate, and the organic phases were combined and sequentially washed with saturated solution of ammonium chloride, distilled water and saturated solution of sodium chloride, then dried with anhydrous sodium sulfate and concentrated under reduced pressure, and the crude product was purified by silica gel column chromatography (petroleum ether/ethyl acetate: 4/1) to obtain 0.68 g of product with a yield of 55.4%.

(4) Preparation of 1-phenyl-3-methyl-5-O-D-glucoside-pyrazole

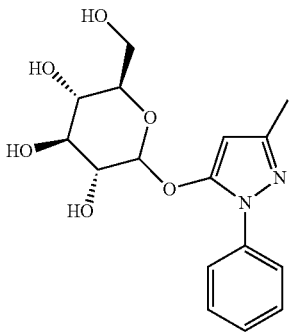 [SMILES: Cc1cc(OC2O[C@H](CO)[C@@H](O)[C@H](O)[C@H]2O)n(-c2ccccc2)n1]

(1-phenyl-3-methyl-5-O-(2,3,4,6-tetra-O-acetyl-D-glucoside) pyrazole (0.2 g) was dissolved in 3 mL of methanol, and then mixed with potassium carbonate (0.27 g), stirring at room temperature for 1 h. After completion of the reaction, the crude product obtained was prepared by semi-preparative high-pressure liquid chromatography and lyophilized using a freeze dryer to obtain 0.11 g of a white solid product. The yield was 79%. (Compound 33 obtained by this method will be applied in the following Examples).

$^1$H NMR (600 MHz, D$_2$O) δ 7.60-7.40 (m, 5H), 5.93 (s, 1H), 5.10 (m, 1H), 3.95-3.86 (m, 1H), 3.79-3.70 (m, 1H), 3.64-3.42 (m, 4H), 2.23 (s, 3H).

ESI-MS (m/z): [M]$^+$ 337.15

Preparation Method 2:

(1) Preparation of 2,3,4,6-tetra-O-benzyl-1-O-trichloroimino-D-glucose

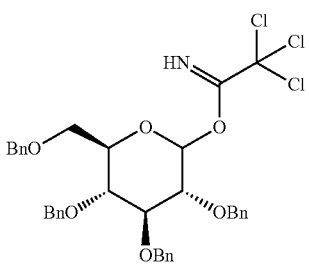 [SMILES: N=C(OC1O[C@H](COCc2ccccc2)[C@@H](OCc2ccccc2)[C@H](OCc2ccccc2)[C@H]1OCc1ccccc1)C(Cl)(Cl)Cl]

2,3,4,6-Tetrabenzyl-D-glucose (12 g, 22.2 mmol) and DBU (0.3 mL, 2.2 mmol) were dissolved in dichloromethane (150 mL), followed by dropwise addition of trichloroacetonitrile (11 mL, 52.9 mmol) while stirring. The reaction was carried out at room temperature for 2 h and completed by TLC confirmation (petroleum ether/ethyl acetate 5:1). The mix was concentrated under reduced pressure to remove the solvent and purified by silica gel column chromatography (petroleum ether/ethyl acetate 10:1) to obtain 11 g of colorless oily substance for the next step.

(2) Preparation of 1-phenyl-3-methyl-5-O-(2,3,4,6-tetrabenzyl-D-glucoside) pyrazole

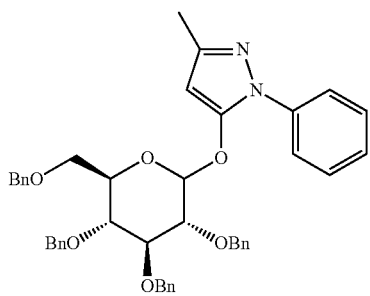 [SMILES: Cc1cc(OC2O[C@H](COCc3ccccc3)[C@@H](OCc3ccccc3)[C@H](OCc3ccccc3)[C@H]2OCc2ccccc2)n(-c2ccccc2)n1]

Edaravone (2.8 g, 16.1 mmol), 2,3,4,6-tetrabenzyl-1-O-trichloroimino-D-glucose (11 g, 16.1 mmol) and 4A molecular sieve were added to dichloromethane, followed by drops of TMSOTf (1.1 mmol), stirring for 1 h at room temperature until the completion by TLC (petroleum ether/ethyl acetate: 4/1). The solvent was removed under reduced pressure and the remaining product was purified by silica gel column chromatography (petroleum ether/ethyl acetate 5:1) to obtain 8.4 g of a light-yellow solid product.

(3) Preparation of 1-phenyl-3-methyl-5-O-D-glucoside-pyrazole

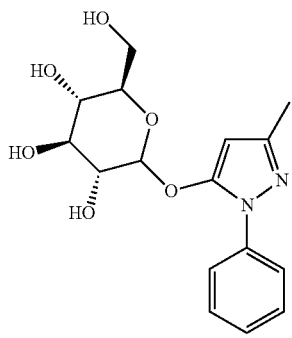 [SMILES: Cc1cc(OC2O[C@H](CO)[C@@H](O)[C@H](O)[C@H]2O)n(-c2ccccc2)n1]

1-Phenyl-3-methyl-5-O-(2,3,4,6-tetrabenzyl-D-glucoside) pyrazole (5 g, 7.2 mmol) was dissolved in methanol (100 mL), and added with Pd/C (10%), for hydrogenated reaction at 40° C. for 6 h. The mix was filtered, and the solvent was removed under reduced pressure. The remaining substance was purified by silica gel column chromatography (petroleum ether/ethyl acetate/methanol 1:1:0.1) to obtain 1.3 g of white solid.

$^1$H NMR (400 MHz, D$_2$O) δ 7.545-7.419 (m, 5H), 5.950 (s, 1H), 5.599 (m, 1H), 3.683-3.623 (m, 4H), 3.483-3.348 (m, 2H), 2.233 (s, 3H).

ESI-MS (m/z): [M]$^+$ 337.15

Example 34: Preparation of 1-phenyl-3-methyl-5-O-D-mannoside-pyrazole

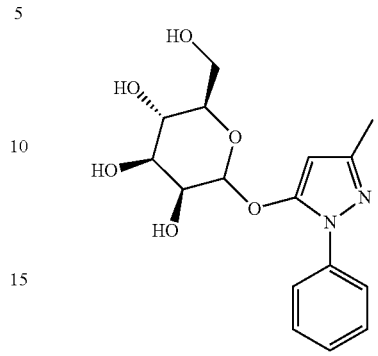

(1) Preparation of 1,2,3,4,6-O-pentaacetyl-D-mannose

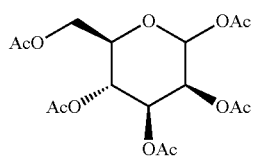 [SMILES: CC(=O)OC[C@H]1OC(OC(C)=O)[C@@H](OC(C)=O)[C@@H](OC(C)=O)[C@@H]1OC(C)=O]

Mannose (4.5 g) and potassium acetate (4.9 g) were dissolved in acetic anhydride (25 mL) at room temperature, and then stirred at 90° C. for 4 h. When the reaction completed, the mix restored to room temperature, and the solvent was removed with an oil pump. The remaining mix was added with 100 mL ethyl acetate and washed with saturated solution of sodium bicarbonate. The aqueous phase was extracted with ethyl acetate and the organic phases were combined and sequentially washed with saturated solution of sodium bicarbonate, distilled water and saturated solution of sodium chloride, then dried with anhydrous sodium sulfate and recrystallized with ethanol to obtain 6.3 g of product with a yield of 63%.

(2) Preparation of 2,3,4,6-O-tetraacetyl-D-bromomannose

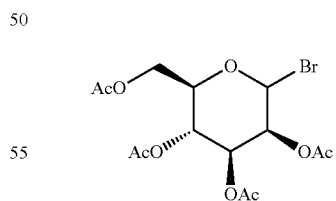

1,2,3,4,6-O-pentaacetyl-D-mannose (1.84 g) was dissolved in dry dichloromethane (4.5 mL). 1.5 mL of 33% hydrogen bromide dissolved in an appropriate amount of acetic acid was added to the above dichloromethane mix at 0° C. The reaction mix was stirred at room temperature for 3.5 h. When the reaction completed, the mix was added with 100 mL dichloromethane and washed with saturated solution of sodium bicarbonate. The aqueous phase was extracted with dichloromethane, and the organic phases were combined and sequentially washed with solution of sodium bicarbonate, distilled water and saturated solution of sodium chloride, then dried with anhydrous sodium sulfate and concentrated under reduced pressure, and the crude product was purified by silica gel column chromatography (petroleum ether/ethyl acetate: 5/1) to obtain 1.19 g of product with a yield of 61.31%.

(3) Preparation of 1-phenyl-3-methyl-5-O-(2,3,4,6-tetra-O-acetyl-D-mannoside) pyrazole

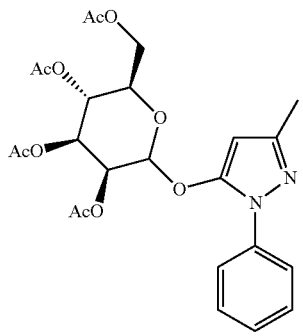 [SMILES: CC(=O)OC[C@H]1OC(Oc2cc(C)nn2-c2ccccc2)[C@@H](OC(C)=O)[C@@H](OC(C)=O)[C@@H]1OC(C)=O]

Edaravone (0.35 g) and cesium carbonate (0.79 g) were dissolved in dry DMF (3.50 mL) and stirred for 20 min at room temperature. 2,3,4,6-tetra-O-acetyl-D-bromomannose (1.0 g) was then added and stirred at room temperature for 24 h. When the reaction completed, a large amount of solvent was removed with an oil pump, and then 100 mL of ethyl acetate was added to the remaining solution. Then the aqueous phase was extracted with ethyl acetate and the organic phases were combined and sequentially washed with saturated solution of ammonium chloride, distilled water and saturated solution of sodium chloride, then dried with anhydrous sodium sulfate and concentrated under reduced pressure, and the crude product was purified by silica gel column chromatography (petroleum ether/ethyl acetate: 4/1), so as to obtain 0.64 g product with a yield of 52.14%.

(4) Preparation of 1-phenyl-3-methyl-5-O-D-mannoside-pyrazole

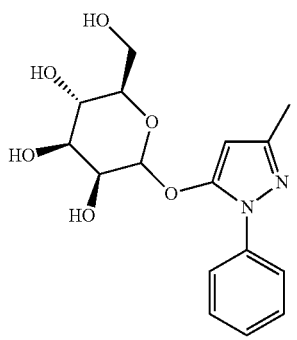 [SMILES: Cc1cc(OC2O[C@H](CO)[C@@H](O)[C@H](O)[C@@H]2O)n(-c2ccccc2)n1]

1-Phenyl-3-methyl-5-O-(2,3,4,6-tetra-O-acetyl-D-mannoside)pyrazole (0.2 g) was dissolved in 3 mL of methanol and then mixed with potassium carbonate (0.28 g), stirring at room temperature for 1 h. After completion of the reaction, the crude product obtained was prepared by semi-preparative high-pressure liquid chromatography and lyophilized using a freeze dryer to obtain 0.13 g of a white solid product. The yield was 77.28%.

$^1$H NMR (400 MHz, D$_2$O) δ 7.58-7.50 (m, 4H), 7.46-7.38 (m, 1H), 5.88 (s, 1H), 5.24 (s, 1H), 4.13-4.06 (m, 1H), 3.97-3.89 (m, 1H), 3.78-3.72 (m, 1H), 3.66-3.59 (m, 2H), 3.53-3.44 (m, 1H), 2.23 (s, 3H).

ESI-MS (m/z): [M]$^+$ 337.14

Example 35: Preparation of 1-phenyl-3-methyl-5-O-D-galactoside-pyrazole

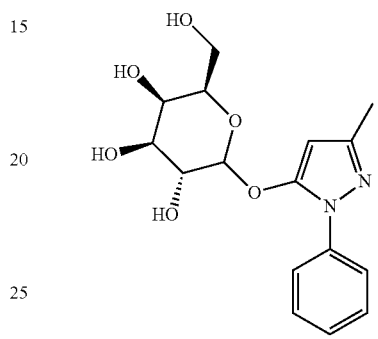

(1) Preparation of 1,2,3,4,6-O-pentaacetyl-D-galactose

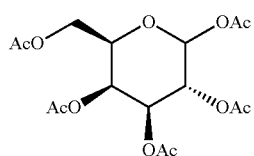 [SMILES: CC(=O)OC[C@H]1OC(OC(C)=O)[C@H](OC(C)=O)[C@@H](OC(C)=O)[C@H]1OC(C)=O]

Galactose (9.0 g) and potassium acetate (9.8 g) were dissolved in acetic anhydride (50 mL) at room temperature, and then stirred at 90° C. for 4 h. When the reaction completed, the mix restored to room temperature. The solvent was removed with an oil pump. The remaining mix was added with 100 ml ethyl acetate and washed with saturated solution of sodium bicarbonate. The aqueous phase was extracted with ethyl acetate and the organic phases were combined and sequentially washed with saturated solution of sodium bicarbonate, distilled water and saturated solution of sodium chloride, dried with anhydrous sodium sulfate and recrystallized with ethanol to obtain 11.0 g of product with a yield of 62%.

(2) Preparation of 2,3,4,6-O-acetyl-D-bromogalactose

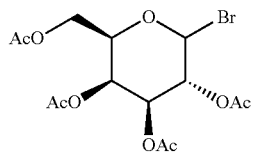 [SMILES: CC(=O)OC[C@H]1OC(Br)[C@H](OC(C)=O)[C@@H](OC(C)=O)[C@H]1OC(C)=O]

1,2,3,4,6-O-pentaacetyl-D-galactose (2.72 g) was dissolved in dry dichloromethane (9 mL). 3 mL of 33% aqueous solution of hydrogen bromide was added to the appropriate amount of acetic acid solution and added to the above dichloromethane solution at 0° C. The mix was stirred at room temperature for 3.5 h. When the reaction completed, the mix was added with 100 mL dichloromethane, then washed with saturated solution of sodium bicarbonate. The aqueous phase was extracted with dichloromethane, and the organic phases were combined and sequentially washed with solution of sodium bicarbonate, distilled water and saturated solution of sodium chloride, then dried with anhydrous sodium sulfate and concentrated under reduced pressure, and the crude product was purified by silica gel column chromatography (petroleum ether/ethyl acetate: 5/1), so as to obtain 1.54 g of product in 54.47% yield.

(3) Preparation of 1-phenyl-3-methyl-5-O-(2,3,4,6-tetra-O-acetyl-D-galactoside) pyrazole

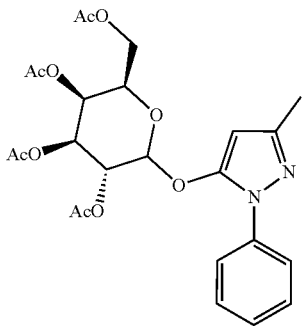 [SMILES: CC(=O)OC[C@H]1OC(Oc2cc(C)nn2-c2ccccc2)[C@H](OC(C)=O)[C@@H](OC(C)=O)[C@H]1OC(C)=O]

Edaravone (0.35 g) and cesium carbonate (0.79 g) were dissolved in dry DMF, stirring at room temperature for 20 min, then followed by addition of. 2,3,4,6-tetra-O-acetyl-D-bromogalactose (1.0 g). The mix was stirred at room temperature for 24 h. When the reaction completed, 100 mL of ethyl acetate was added to the reaction mix, which was then washed with saturated solution of ammonium chloride, and the aqueous phase was extracted with ethyl acetate and the organic phases were combined and sequentially washed with saturated solution of ammonium chloride, distilled water and saturated solution of sodium chloride, then dried with anhydrous sodium sulfate, and the solvent was removed by a rotary evaporator. The crude product obtained was purified by silica gel column chromatography (petroleum ether/ethyl acetate: 4/1) to obtain 0.99 g of product in a yield of 75.20%.

(4) Preparation of 1-phenyl-3-methyl-5-O-D-galactoside-pyrazole

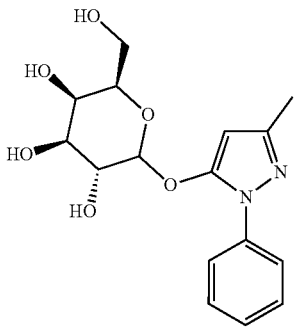 [SMILES: Cc1cc(OC2O[C@H](CO)[C@H](O)[C@H](O)[C@H]2O)n(-c2ccccc2)n1]

1-Phenyl-3-methyl-5-O-(2,3,4,6-tetra-O-acetyl-D-galactoside)pyrazole (0.2 g) was dissolved in 3 mL of methanol and mixed with potassium carbonate (0.28 g), stirring at room temperature for 1 h. After completion of the reaction, the crude product was prepared by semi-preparative high-pressure liquid chromatography and lyophilized using a freeze-dryer to obtain 0.11 g of white solid. The yield was 79.36%.

$^1$H NMR (400 MHz, D$_2$O) δ 7.51-7.41 (m, 4H), 7.38-7.31 (m, 1H), 5.84 (s, 1H), 4.97 (m, 1H), 3.89 (s, 1H), 3.79-3.73 (m, 1H), 3.70-3.60 (m, 4H), 2.15 (s, 3H).

ESI-MS (m/z): [M]$^+$ 337.17

Example 36: Preparation of 1-phenyl-3-methyl-5-O-D-(2-deoxy)glucoside-pyrazole

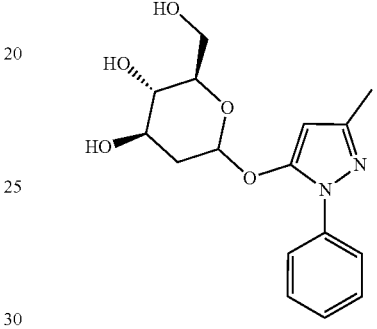

(1) Preparation of 1,3,4,6-tetra-O-acetyl-D-(2-deoxy)glucose

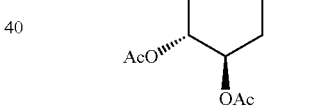

2-Deoxyglucose (1.0 g, 6.1 mmol) was dispersed in acetic anhydride (5 mL), followed by slow addition of potassium acetate (0.99 g, 9.1 mmol) at 65° C., and the mix was stirred at 70° C. for 3.5 h until completed by TLC detection. The mix was cooled to 50° C., the solvent was removed under reduced pressure, and purified by silica gel column chromatography to obtain 1.2 g of white solid with a yield of 59%.

(2) Preparation of 3,4,6-tri-O-acetyl-D-bromo-(2-deoxy)glucose

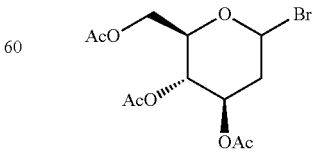

1,3,4,6-tetra-O-acetyl-D-(2-deoxy)glucose (2.5 g) was dissolved in dry dichloromethane (8 mL), followed by addition of 2.9 mL of 33% aqueous hydrogen bromide with an appropriate amount of acetic acid solution at 0° C. The mix was stirred and reacted at room temperature for 2 h. When the reaction completed, the mix was added with 100 mL dichloromethane, then washed with saturated solution of sodium bicarbonate. The aqueous phase was extracted with dichloromethane, and the organic phases were combined, sequentially washed with solution of sodium bicarbonate, distilled water and saturated solution of sodium chloride, then dried with anhydrous sodium sulfate and the solvent was removed by a rotary evaporator, and the crude product was purified by silica gel column chromatography (petroleum ether/ethyl acetate=3/1) to obtain 1.79 g of product in a yield of 67.43%.

(3) Preparation of 1-phenyl-3-methyl-5-O-(3,4,6-tri-O-acetyl-D-(2-deoxy)glucoside) pyrazole

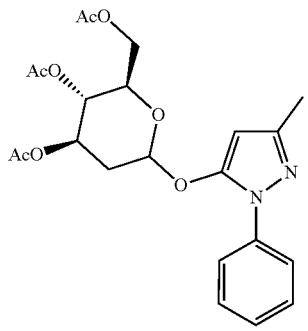 [SMILES: CC(=O)OC[C@H]1OC(Oc2cc(C)nn2-c2ccccc2)C[C@@H](OC(C)=O)[C@@H]1OC(C)=O]

Edaravone (4.93 g) and cesium carbonate (1.34 g) were dissolved in dry DMF and stirred at room temperature for 20 min then followed by addition of 3,4,6-Tri-O-acetyl-D-bromo-(2-deoxy) glucose (1.0 g) and stirred at room temperature for 24 h. When the reaction completed, a large amount of solvent was removed with an oil pump. Then 100 mL of ethyl acetate was added to the mix and washed. The aqueous phase was extracted with ethyl acetate and the organic phases were combined and sequentially washed with saturated ammonium chloride, distilled water and saturated sodium chloride solution, then dried with anhydrous sodium sulfate and concentrated under reduced pressure, and the crude product was purified by silica gel column chromatography (petroleum ether/ethyl acetate: 4/1), so as to obtain 1.07 g of product with a yield of 84.27%.

(4) Preparation of 1-phenyl-3-methyl-5-O-D-(2-deoxy) glucoside-pyrazole

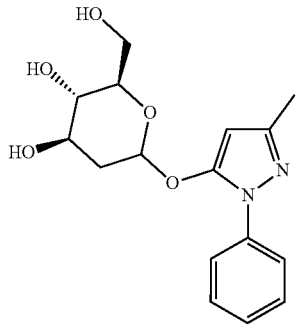 [SMILES: Cc1cc(OC2C[C@@H](O)[C@H](O)[C@@H](CO)O2)n(-c2ccccc2)n1]

1-Phenyl-3-methyl-5-O-(3,4,6-tri-O-acetyl-D-(2-deoxy) glucoside) pyrazole (1.0 g) was dissolved in 15 mL of methanol, followed by addition of potassium carbonate (1.55 g). The mix was stirred at room temperature for 1.5 h. After completion of the reaction, the crude product obtained was separated by semi-preparative high-pressure liquid chromatography and lyophilized using a freeze dryer to obtain a white solid product 0.68 g with a yield of 94.12%.

$^1$H NMR (600 MHz, DMSO) δ 7.63 (d, J=7.9 Hz, 2H), 7.45 (t, J=7.6 Hz, 2H), 7.27 (t, J=7.2 Hz, 1H), 5.83 (s, 1H), 5.23 (m, 1H), 3.69 (d, J=11.6 Hz, 1H), 3.56-3.47 (m, 2H), 3.26-3.19 (m, 1H), 3.17 (s, 1H), 3.08 (t, J=8.9 Hz, 1H), 2.24-2.17 (d, J=8.0 Hz, 1H), 2.16 (s, 3H).

ESI-MS (m/z): [M]$^+$ 321.20

Example 37: Preparation of 1-phenyl-3-methyl-5-O-D-(2-amino-2-deoxy)glucoside-pyrazole

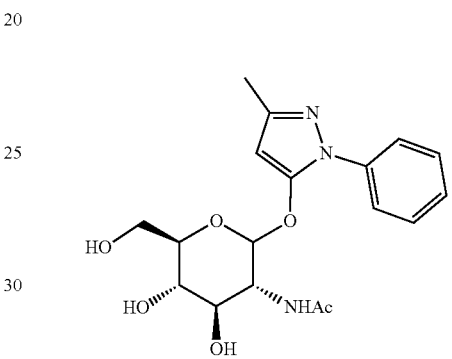

(1) Preparation of 2-acetamido-1,3,4,6-tetraacetoxy-2-deoxyglucose

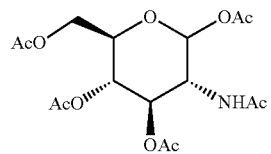 [SMILES: CC(=O)N[C@H]1C(OC(C)=O)O[C@H](COC(C)=O)[C@@H](OC(C)=O)[C@@H]1OC(C)=O]

2-Amino-2-deoxyglucose hydrochloride (2.2 g, 10.2 mmol) was suspended in pyridine (10 mL), cooled to 0° C., followed by addition of acetic anhydride (9.4 mL, 99.6 mmol). The mix was stirred overnight at room temperature and added with ethyl acetate (100 mL), sequentially washed with 5% diluted hydrochloric acid, saturated sodium bicarbonate and saturated NaCl solution. The organic phases were dried with anhydrous sodium sulfate and concentrated by rotary evaporation under reduced pressure, and the remaining product was recrystallized with dichloromethane/ethyl ether to obtain 3.3 g of white solid product.

(2) Preparation of 2-acetamido-3,4,6-triacetoxy-2-deoxyglucose bromide

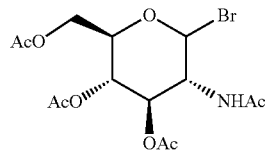 [SMILES: CC(=O)N[C@H]1C(Br)O[C@H](COC(C)=O)[C@@H](OC(C)=O)[C@@H]1OC(C)=O]

2-Acetamido-1,3,4,6-tetraacetoxy-2-deoxyglucose (1.0 g, 2.6 mmol) was dissolved in dichloromethane (1 mL), cooled to 0° C., followed by slowly addition of acetic acid solution of hydrogen bromide (1.6 mL, 33% in acetic acid). The mix reacted at room temperature for 3 h, and was added with dichloromethane (50 mL). The organic phases were washed with saturated sodium bicarbonate, saturated NaCl solution, and dried with anhydrous sodium sulfate. The solvent was removed under reduced pressure, and the remaining product was used directly in the next step.

(3) Preparation of 5-(2-acetamido-3,4,6-triacetoxy-2-deoxyglucoside)-3-methyl-1-phenyl-1H-pyrazole

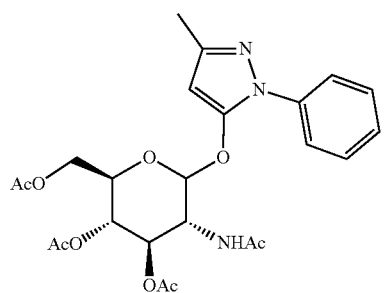 [SMILES: CC(=O)N[C@H]1C(Oc2cc(C)nn2-c2ccccc2)O[C@H](COC(C)=O)[C@@H](OC(C)=O)[C@@H]1OC(C)=O]

Edaravone (452 mg, 2.6 mmol) was dissolved in dichloromethane (5 mL). The mix was added with triethylamine (0.9 mL, 6.5 mmol) and stirred at room temperature for 20 min, and cooled to 0° C. 2-acetamido-3,4,6-triacetoxy-2-deoxyglucose bromide dissolved in small amount of dichloromethane was slowly added to the mix in drops, stirring at room temperature and reacting for 3 h, diluted with dichloromethane (50 mL). The organic phases were washed with saturated ammonium chloride and saturated NaCl solution, dried with anhydrous sodium sulfate. The solvent was removed under reduced pressure and the remaining product was purified by silica gel column chromatography (petroleum ether/ethyl acetate: 1/1 to obtain a crude product of white solid for the next step.

Preparation of 1-phenyl-3-methyl-5-O-D-(2-amino-2-deoxy) glucoside-pyrazole

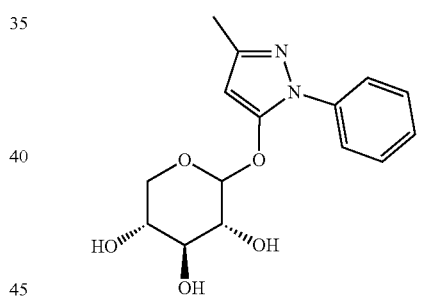

The crude product of the previous step was dissolved in methanol (15 mL), and the mix was added with potassium carbonate (538 mg, 3.9 mmol) was added and stirred at room temperature for 2 h. The pH was adjusted to neutral with acetic acid and separated by semi-preparation column (MeOH/H$_2$O=2/3) to obtain 300 mg of white solid.

$^1$H NMR (400 MHz, D$_2$O), δ 7.34-7.43 (m, 5H); 5.87 (s, 1H); 4.97 (m, 1H); 3.70-3.88 (m, 3H); 3.42-3.52 (m, 3H); 2.15 (s, 3H); 1.65 (s, 3H)

ESI-MS (m/z): [M]$^+$ 378.19

Example 38: Preparation of 1-phenyl-3-methyl-5-O-D-xylopyranoside-pyrazole

(1) Preparation of 1,2,3,4-tetra-O-acetyl-D-xylopyranose

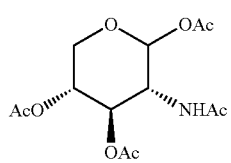 [SMILES: CC(=O)N[C@H]1C(OC(C)=O)OC[C@@H](OC(C)=O)[C@@H]1OC(C)=O]

Xylose (2 g, 13.3 mmol) was suspended in pyridine (10 mL), following by slow addition dropwise of acetic anhydride (10 mL, 106 mmol) at 0° C., and the mix was stirred overnight, extracted by ethyl acetate (100 mL), washed with 5% dilute hydrochloric acid, saturated sodium bicarbonate solution, saturated saline solution, dried with anhydrous sodium sulfate, and concentrated by rotary evaporation under reduced pressure to obtain 4 g of product, which was directly used in the next step.

(2) Preparation of 2,3,4-triacetoxy-D-xylopyranose bromide

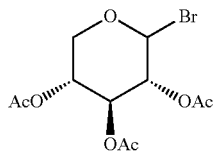

1,2,3,4-tetra-O-acetyl-D-xylopyranose (2.5 g, 7.86 mmol) was dissolved in dichloromethane (2 mL), cooled to 0° C. The mix was slowly added with acetic acid solution of hydrogen bromide (33 wt %, 8.5 mL) dropwise and reacted for 30 min at room temperature, then extracted by dichloromethane (50 mL). The organic phases were washed with saturated sodium bicarbonate, saturated NaCl solution, and dried with anhydrous sodium sulfate. The solvent was removed under reduced pressure, the remaining product was recrystallized with ether and n-hexane to obtain 2.43 g of product.

(3) 5-(2,3,4-Triacetoxy-D-xylopyranoside)-3-methyl-1-phenyl-1H-pyrazole

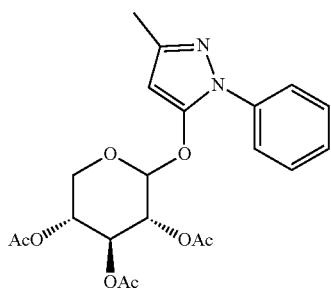 [SMILES: CC(=O)O[C@H]1[C@H](OC(C)=O)COC(Oc2cc(C)nn2-c2ccccc2)[C@@H]1OC(C)=O]

Edaravone (1.2 g, 7.1 mmol) was suspended in acetonitrile (15 mL) and cooled to 0° C. Sodium hydride (284 mg, 7.1 mmol, 60% in oil) was slowly added and the mix was stirred for 20 min at room temperature. Then 2,3,4-triacetoxy-D-xylopyranose bromide (2.4 g, 7.1 mmol) was added, stirring continued for 1 h at room temperature. The mix was extracted by ethyl acetate and water. The organic phases were dried with anhydrous sodium sulfate, and concentrated by rotary evaporation under reduced pressure, so as to obtain the crude product for the next step.

(4) Preparation of 1-phenyl-3-methyl-5-O-D-xylopyranoside-pyrazole

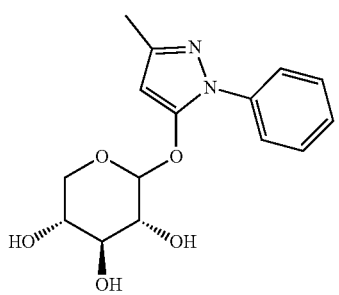 [SMILES: Cc1cc(OC2OC[C@@H](O)[C@H](O)[C@H]2O)n(-c2ccccc2)n1]

The crude product of the previous step was dissolved in methanol, potassium carbonate (1.5 g, 10.7 mmol) was added, and the mix was stirred at room temperature for 1 h. Then the pH was adjusted to about 7 by acetic acid, the solvent was removed by rotary evaporation, and the remaining product was subject to silica gel column chromatography (petroleum ether/ethyl acetate: 8/1) to obtain 800 mg of product.

$^1$H MNR (400 MHz, CD$_3$OD), δ7.62-7.64 (m, 2H); 7.42-7.45 (m, 2H); 7.29-7.31 (m, 1H); 5.81 (s, 1H); 4.96-4.97 (m, 1H); 3.94 (dd, J=7.7 Hz, J=3.4 Hz, 1H); 3.53-3.57 (m, 1H); 3.35-3.42 (m, 3H); 2.23 (s, 3H)

ESI-MS (m/z): [M]$^+$ 307.18

Example 39: Preparation of 1-phenyl-3-methyl-5-O-D-riboside-pyrazole

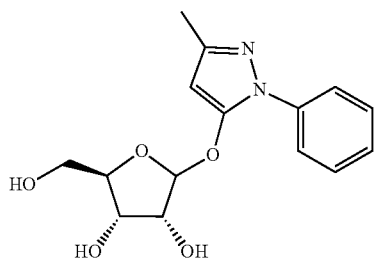 [SMILES: Cc1cc(OC2O[C@H](CO)[C@@H](O)[C@H]2O)n(-c2ccccc2)n1]

(1) Preparation of 1-methoxy-D-ribose

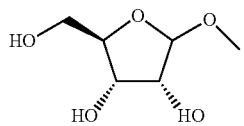

D-ribose (5 g, 33.3 mmol) was suspended in methanol (80 mL) and ice bathed. Concentrated sulfuric acid (0.5 mL, 9.4 mmol) was added slowly dropwise until the temperature raised to 60° C. for reaction overnight. The pH was adjusted to 9 with ammonia. The mix was filtered, and subject to reduced pressure for solvent removal, so as to obtain 5 g of crude product for the next step.

(2) Preparation of 1-methoxy-2, 3, 4-tribenzoyl-D-ribose

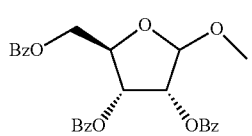

1-Methoxy-D-ribose (2 g, 12.2 mmol) was dissolved in pyridine (30 mL), cooled to 0° C. Benzoyl chloride (8 mL, 69 mmol) was added slowly dropwise. The mix was stirred at room temperature overnight and extracted by ethyl acetate (100 mL), and then washed with 5% dilute hydrochloric acid, saturated sodium bicarbonate, saturated saline solution, dried with anhydrous sodium sulfate, then concentrated under reduced pressure, and the remaining product was subjected to silica gel column chromatography (petroleum ether/ethyl acetate: 10/1) to obtain 4 g of oily product.

(3) Preparation of 2, 3, 4-tribenzoyl-D-ribose bromide

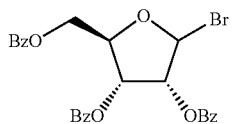

1-Methoxy-2, 3, 4-tribenzoyl-D-ribose (2.4 g, 5 mmol) was dissolved in acetic acid (8 mL), followed by slow addition of acetic acid solution of hydrogen bromide (33 wt %, 8 mL), reacting for 2 h at room temperature, which is then separated by iichloromethane (50 mL). The organic phases were washed with saturated sodium bicarbonate, saturated saline solution, and dried with anhydrous sodium sulfate. The solvent was removed under reduced pressure, and the remaining substance was directly used in the next step.

(4) Preparation of 5-(2,3,4-tribenzoyloxy-D-riboside)-3-methyl-1-phenyl-1H-pyrazole

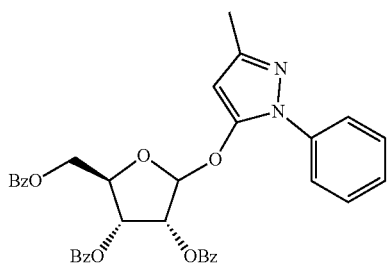

Edaravone (870 mg, 5 mmol) was suspended in acetonitrile (10 mL), followed by addition of cesium carbonate (1.7 g, 5.25 mmol), stirred for 20 min at room temperature. 2, 3, 4-tribenzoyl-D-ribose bromide was dissolved with a small amount of acetonitrile and was dropwise added to the reaction solution, continuing to stir for 1 h. The solution was extracted by ethyl acetate and water. The organic phases were dried with anhydrous sodium sulfate, concentrated by rotary evaporation under reduced pressure, and the remaining product was subjected to silica gel column chromatography (petroleum ether/ethyl acetate: 5/1) to obtain 1 g of white solid product.

(5) Preparation of 1-phenyl-3-methyl-5-O-D-riboside-pyrazole

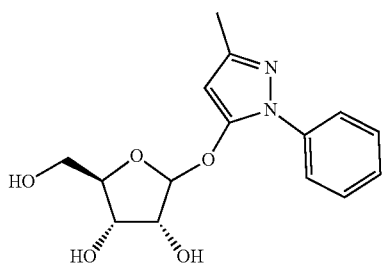 [SMILES: Cc1cc(OC2O[C@H](CO)[C@@H](O)[C@H]2O)n(-c2ccccc2)n1]

5-(2,3,4-Tribenzoyloxy-D-riboside)-3-methyl-1-phenyl-1H-pyrazole (309 mg, 0.5 mmol) was dissolved in methanol (3 mL), then the methanol solution of sodium methanol (30%, 0.25 mL) was added, and reacted at room temperature for 2 h. The pH was adjusted to about 7 with acetic acid, the solvent was removed under reduced pressure, and the residue was subjected to silica gel column chromatography (petroleum ether/Ethyl acetate: 1/2) to obtain 50 mg of white solid product.

$^1$H MNR (400 MHz, CD$_3$OD), δ 7.53-7.57 (m, 2H); 7.41-7.47 (m, 2H); 7.28-7.33 (m, 1H); 5.80 (s, 1H); 5.49 (s, 1H); 4.03-4.16 (m, 3H); 3.68 (dd, J=12.0 Hz, J=3.3 Hz, 1H); 3.68 (dd, J=12.0 Hz, J=5.8 Hz, 1H); 2.23 (s, 3H)

ESI-MS (m/z): [M]$^+$ 307.04

Example 40: Preparation of 1-phenyl-3-methyl-5-O-D-(2-deoxy)riboside-pyrazole

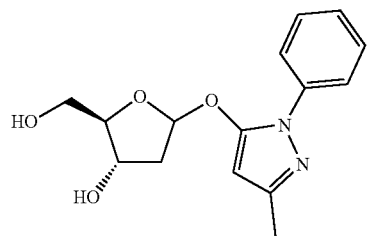 [SMILES: Cc1cc(OC2C[C@H](O)[C@@H](CO)O2)n(-c2ccccc2)n1]

(1) Preparation of 5-(3,5-bis-p-chlorobenzoyloxy-2-D-deoxyriboside)-3-methyl-1-phenyl-1H-pyrazole

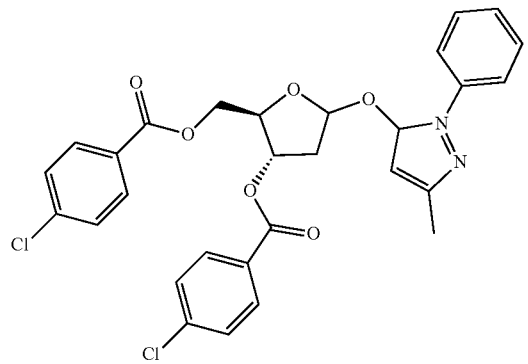

Edaravone (500 mg, 2.9 mmol) was suspended in acetonitrile (15 mL) and cooled to 0° C. Sodium hydride (115 mg, 2.9 mmol, 60% in oil) was slowly added and stirred for 20 min at room temperature, followed by the addition of 3,5-di-p-chlorobenzoyloxy-2-D-deoxyribose chloride (1.25 g, 2.9 mmol), stirred for another 3 h at room temperature, separated by ethyl acetate and water. The organic phases were dried with anhydrous sodium sulfate, concentrated by rotary evaporation under reduced pressure, and the remaining product was purified by silica gel column chromatography (petroleum ether/ethyl acetate: 5/1) to obtain 450 mg of crude product.

Preparation of 1-phenyl-3-methyl-5-O-D-(2-deoxy) riboside-pyrazole

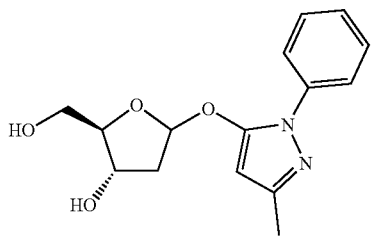 [SMILES: Cc1cc(OC2C[C@H](O)[C@@H](CO)O2)n(-c2ccccc2)n1]

5-(3,5-Di-p-chlorobenzoyloxy-2-D-deoxyriboside)-3-methyl-1-phenyl-1H-pyrazole (450 mg, 0.8 mmol) was dissolved in a mix solution of methanol and dichloromethane (1:1, 10 mL), which was added with methanol solution of sodium methanol (30%, 0.2 mL) for 2 h reaction at RT. The pH was adjusted to about 7 with acetic acid, then the solvent was removed under reduced pressure, and the remaining product was purified by silica gel column chromatography (petroleum ether/ethyl acetate: 1/1.5) to obtain 100 mg of white solid product.

$^1$H MNR (400 MHz, CD$_3$OD), δ 7.55 (dd, J=8.7 Hz, J=1.2 Hz, 2H); 7.44 (t, J=7.9 Hz, 2H); 7.31 (t, J=7.4 Hz, 1H); 5.82 (m, 1H); 5.80 (s, 1H); 4.35 (dd, J=11.4 Hz, J=6.6 Hz, 1H); 3.96 (dd, J=10.9 Hz, J=5.3 Hz, 1H); 3.55 (dd, J=11.7 Hz, J=5.2 Hz, 1H); 3.45 (dd, J=11.7 Hz, J=6.3 Hz, 1H); 2.43 (dd, J=13.8 Hz, J=6.7 Hz, 1H); 2.22-2.26 (m, 4H)

ESI-MS (m/z): [M]$^+$ 291.17

Examples 41-52

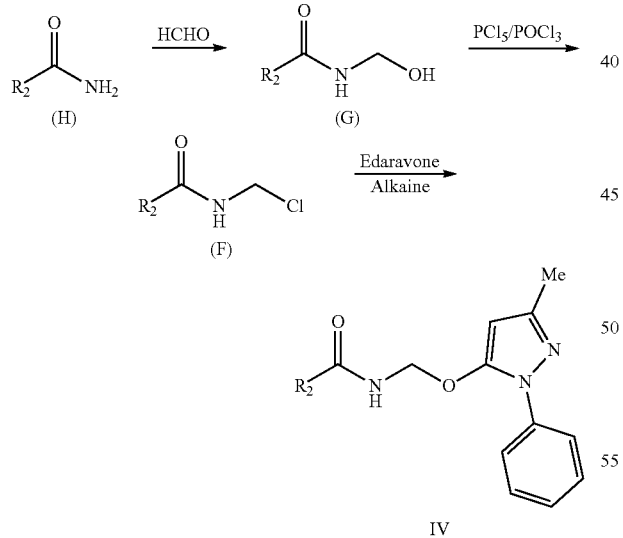

General Synthetic Route 4:

Step 1.

The compound of formula (H) (5.62 mmol) and KOH (0.66 mmol) were dissolved in 20 mL H$_2$O/dioxane (1:3 v/v) solution. Formaldehyde (35% aqueous solution, 8.43 mmol) was added to the above mixed solution, the reaction solution reacted at 70° C. for 5 min, then cooled down to 25° C. and was stirred overnight. The pH was adjusted to 7 with 1N HCl and concentrated under reduced pressure. The remaining substance was dissolved with acetone, dried with anhydrous sodium sulfate, filtered and concentrated to obtain the compound of formula (G) for next step.

Step 2.

The compound of formula (G) (3.0 mmol) was dissolved in 10 mL POCl$_3$, and heated to reflux. PCl$_5$ (6.0 mmol) was added carefully in portions. The reaction was refluxed for 2.5 h until completion by TLC detection. Cooled to room temperature, the reaction solution was added with 200 mL of ice water and was adjusted to pH neutral with 1N NaOH solution, then extracted with CH$_2$Cl$_2$, dry with anhydrous sodium sulfate, undergoing filtering, concentration and purification by column chromatography to obtain the compound of formula (F).

Step 3.

Edaravone (3.6 mmol), potassium iodide (0.4 mmol), and potassium carbonate (10 mmol) were dissolved in dry DMF (10 mL) and stirred for 10 min at 45° C. Then the DMF solution and the compound of formula (F) (3.3 mmol) were mixed and stirred for 1 h at 45° C. When the reaction completed, the solvent was removed with an oil pump, and then 100 mL ethyl acetate was added and washed by saturated ammonium chloride solution, which was repeated two times. The organic phases were combined and washed by distilled water and saturated ammonium chloride solution sequentially, then dried with anhydrous sodium sulfate, and concentrated under reduced pressure. The crude product was purified by silica gel column chromatography to obtain the target product.

Example 41: Preparation of N-((1-phenyl-3-methyl-1H-pyrazol-5-yl)oxy) methylacetamide

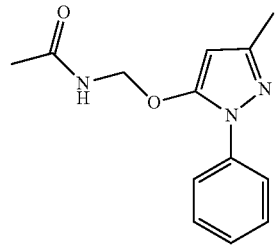 [SMILES: CC(=O)NCOc1cc(C)nn1-c1ccccc1]

The compound was prepared by the general synthetic route 4 as yellow oily substance, and the yield was 43.9%.

$^1$H NMR (400 MHz, CDCl$_3$) δ 8.03 (s, 1H), 7.60-7.50 (m, 2H), 7.45-7.40 (m, 2H), 7.31-7.26 (m, 1H), 6.08 (s, 1H), 5.84 (s, 2H), 2.32 (s, 3H), 1.83 (s, 3H).

ESI-MS (m/z): [M]$^+$ 246.10

Example 42: Preparation of N-((1-phenyl-3-methyl-1H-pyrazol-5-yl)oxy) methyl propionamide

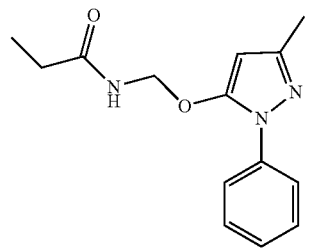 [SMILES: CCC(=O)NCOc1cc(C)nn1-c1ccccc1]

The compound was prepared by the general synthetic route 4 as yellow oily substance, and the yield was 41.2%.

¹H NMR (400 MHz, CDCl₃) δ 8.01 (s, 1H), 7.62-7.51 (m, 2H), 7.43-7.41 (m, 2H), 7.32-7.29 (m, 1H), 6.07 (s, 1H), 5.83 (s, 2H), 2.32 (s, 3H), 2.27 (m, 2H), 1.02 (t, 3H).

ESI-MS (m/z): [M]⁺ 260.17

Example 43: Preparation of N-((1-phenyl-3-methyl-1H-pyrazol-5-yl)oxy) methylisobutyramide

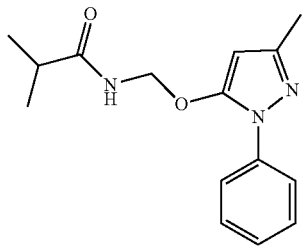 [SMILES: Cc1cc(OCNC(=O)C(C)C)n(-c2ccccc2)n1]

The compound was prepared by the general synthetic route 4 as yellow oily substance, and the yield was 40.8%.

¹H NMR (400 MHz, CDCl₃) δ 8.03 (s, 1H), 7.61-7.54 (m, 2H), 7.45-7.40 (m, 2H), 7.34-7.28 (m, 1H), 6.05 (s, 1H), 5.86 (s, 2H), 2.53 (dt, J=14.0, 7.0 Hz, 1H), 2.33 (s, 3H), 1.22 (d, J=7.0 Hz, 6H).

ESI-MS (m/z): [M]⁺ 274.16

Example 44: Preparation of N-((1-phenyl-3-methyl-1H-pyrazol-5-yl)oxy) methyltrimethylacetamide

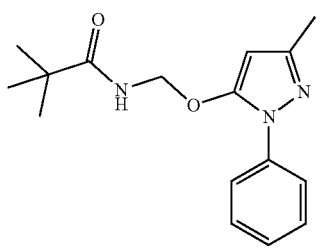 [SMILES: Cc1cc(OCNC(=O)C(C)(C)C)n(-c2ccccc2)n1]

The compound was prepared by the general synthetic route 4 as yellow oily substance, and the yield was 43.2%.

¹H NMR (400 MHz, CDCl₃) δ 8.02 (s, 1H), 7.62-7.53 (m, 2H), 7.47-7.41 (m, 2H), 7.35-7.27 (m, 1H), 6.03 (s, 1H), 5.82 (s, 2H), 2.33 (s, 3H), 1.20 (s, 9H).

ESI-MS (m/z): [M]⁺ 288.12

Example 45: Preparation of N-((1-phenyl-3-methyl-1H-pyrazol-5-yl)oxy) methylcyclopropylformamide

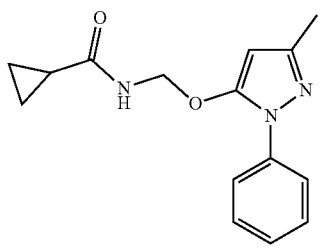 [SMILES: Cc1cc(OCNC(=O)C2CC2)n(-c2ccccc2)n1]

The compound was prepared by the general synthetic route 4 as yellow oily substance, and the yield was 38.1%.

¹H NMR (400 MHz, CDCl₃) δ 8.03 (s, 1H), 7.64-7.53 (m, 2H), 7.45-7.41 (m, 2H), 7.34-7.26 (m, 1H), 6.01 (s, 1H), 5.83 (s, 2H), 2.33 (s, 3H), 1.43 (m, 1H), 0.98 (dd, J=4.42, 2.98 Hz, 2H), 0.79 (dd, J=7.91, 2.95 Hz, 2H).

ESI-MS (m/z): [M]⁺ 272.15

Example 46: Preparation of N-((1-phenyl-3-methyl-1H-pyrazol-5-yl)oxy) methylcyclopentylformamide

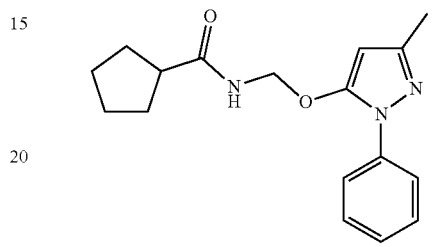

The compound was prepared by the general synthetic route 4 as yellow oily substance, and the yield was 39.8%.

¹H NMR (400 MHz, CDCl₃) δ 8.02 (s, 1H), 7.61-7.53 (m, 2H), 7.44-7.40 (m, 2H), 7.32-7.25 (m, 1H), 6.02 (s, 1H), 5.81 (s, 2H), 2.34 (s, 3H), 2.61 (q, J=8.0 Hz, 1H), 1.93-1.84 (m, 2H), 1.82-1.68 (m, 4H), 1.64-1.52 (m, 2H).

ESI-MS (m/z): [M]⁺ 300.23

Example 47: Preparation of N-((1-phenyl-3-methyl-1H-pyrazol-5-yl)oxy) methylcyclohexanecarboxamide

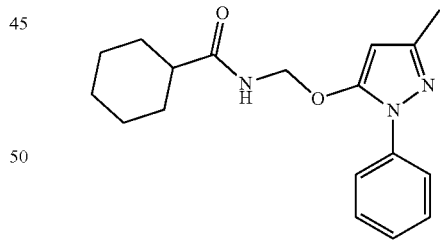

The compound was prepared by the general synthetic route 4 as yellow oily substance, and the yield was 40.1%.

¹H NMR (400 MHz, CDCl₃) δ 8.03 (s, 1H), 7.62-7.53 (m, 2H), 7.45-7.41 (m, 2H), 7.33-7.24 (m, 1H), 6.03 (s, 1H), 5.82 (s, 2H), 2.32 (s, 3H), 2.13 (m, 1H), 1.89 (m, 2H), 1.78 (m, 2H), 1.66 (m, 1H), 1.42 (m, 2H), 1.24 (m, 3H).

ESI-MS (m/z): [M]⁺ 314.24

Example 48: Preparation of N-((1-phenyl-3-methyl-1H-pyrazol-5-yl)oxy) methylbenzamide

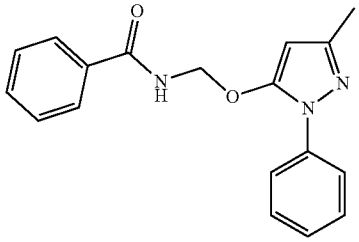 [SMILES: Cc1cc(OCNC(=O)c2ccccc2)n(-c2ccccc2)n1]

The compound was prepared by the general synthetic route 4 as yellow oily substance, and the yield was 45.8%.

$^1$H NMR (400 MHz, CDCl$_3$) δ 8.02 (s, 1H), 7.84-7.81 (m, 2H), 7.65-7.59 (m, 2H), 7.57-7.52 (m, 1H), 7.49-7.43 (m, 4H), 7.35-7.26 (m, 1H), 6.05 (s, 1H), 5.87 (s, 2H), 2.30 (s, 3H).

ESI-MS (m/z): [M]$^+$ 308.16

Example 49: Preparation of N-((1-phenyl-3-methyl-1H-pyrazol-5-yl)oxy) methylphenylacetamide

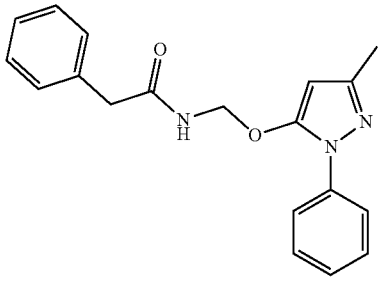 [SMILES: Cc1cc(OCNC(=O)Cc2ccccc2)n(-c2ccccc2)n1]

The compound was prepared by the general synthetic route 4 as yellow oily substance, and the yield was 43.4%.

$^1$H NMR (400 MHz, CDCl$_3$) δ 8.02 (s, 1H), 7.65-7.59 (m, 2H), 7.45-7.41 (m, 2H), 7.35-7.20 (m, 6H), 6.05 (s, 1H), 5.87 (s, 2H), 3.38 (s, 2H), 2.30 (s, 3H).

ESI-MS (m/z): [M]$^+$ 322.20

Example 50: Preparation of N-((1-phenyl-3-methyl-1H-pyrazol-5-yl)oxy) methylphenylbutyramide

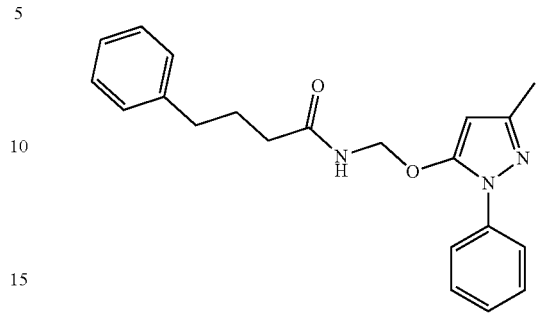

The compound was prepared by the general synthetic route 4 as yellow oily substance, and the yield was 40.5%.

$^1$H NMR (400 MHz, CDCl$_3$) δ 8.03 (s, 1H), 7.62-7.53 (m, 2H), 7.45-7.41 (m, 2H), 7.33-7.24 (m, 3H), 7.18 (t, J=7.6 Hz, 3H), 6.03 (s, 1H), 5.82 (s, 2H), 2.68 (t, J=7.5 Hz, 2H), 2.32 (s, 3H), 2.22 (t, J=7.5 Hz, 2H), 2.04-1.93 (m, 2H).

ESI-MS (m/z): [M]$^+$ 350.11

Example 51: Preparation of N-((1-phenyl-3-methyl-1H-pyrazol-5-yl)oxy) methyloctylamide

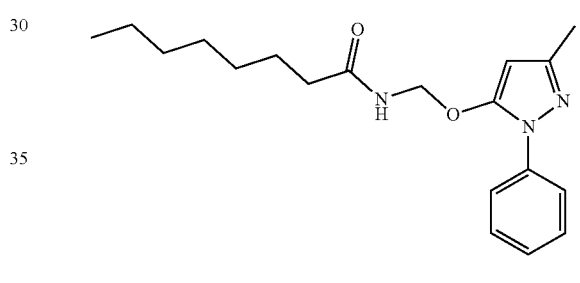

The compound was prepared by the general synthetic route 4 as yellow solid, and the yield was 38.3%.

$^1$H NMR (400 MHz, CDCl$_3$) δ 8.02 (s, 1H), 7.61-7.54 (m, 2H), 7.46-7.41 (m, 2H), 7.31-7.25 (m, 1H), 6.02 (s, 1H), 5.81 (s, 2H), 2.38 (t, J=4.0 Hz, 2H), 2.31 (s, 3H), 1.51-1.46 (m, 2H), 1.34-1.25 (m, 8H), 0.90 (t, J=4.0 Hz, 3H).

ESI-MS (m/z): [M]$^+$ 330.18

Example 52: Preparation of N-((1-phenyl-3-methyl-1H-pyrazol-5-yl)oxy)methyl stearamide

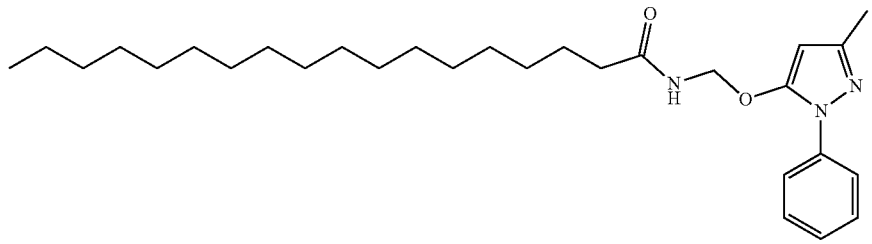 [SMILES: CCCCCCCCCCCCCCCCCC(=O)NCOc1cc(C)nn1-c1ccccc1]

The compound was prepared by the general synthetic route 4 as yellow solid, and the yield was 32.7%.

$^1$H NMR (400 MHz, CDCl$_3$) δ 8.02 (s, 1H), 7.61-7.54 (m, 2H), 7.46-7.41 (m, 2H), 7.31-7.25 (m, 1H), 6.02 (s, 1H), 5.81 (s, 2H), 2.31 (s, 3H), 2.22 (t, J=7.6 Hz, 2H), 1.65-1.63 (m, 2H), 1.34-1.25 (m, 28H), 0.87 (t, J=6.8 Hz, 3H).

ESI-MS (m/z): [M]$^+$ 470.30

EXPERIMENTAL EXAMPLES

Test Example 1: Stability Studies

The stability of samples from some embodiments were examined under high humidity (25° C.±2° C., 90%±5RH), illumination (25° C.±2° C., 60%±5RH, 4500±500LX), high temperature (60° C.±2° C., 60%±5RH), which were stored in the stability incubator for seven days, for the changes of related substances and contents, as shown in Table 2.

TABLE 2

| Compound | High humidity (25° C. ± 2° C., 90% ± 5 RH) | Illumination (25° C. ± 2° C., 60% ± 5 RH, 4500 ± 500 LX) | High Temperature (60° C. ± 2° C., 60% ± 5 RH) |
|---|---|---|---|
| ED | No significant changes in related substances | Content Drop by 4% | No significant changes in related substances |
| Compound of Formula (I) disclosed by CN107400089 | Content Drop by 7% | Content Drop by 10% | Content Drop by 13% |
| 1 | No significant changes in related substances | No significant changes in related substances | No significant changes in related substances |
| 7 | No significant changes in related substances | No significant changes in related substances | No significant changes in related substances |
| 15 | No significant changes in related substances | No significant changes in related substances | No significant changes in related substances |
| 18 | No significant changes in related substances | No significant changes in related substances | No significant changes in related substances |
| 20 | No significant changes in related substances | No significant changes in related substances | No significant changes in related substances |
| 26 | No significant changes in related substances | No significant changes in related substances | No significant changes in related substances |
| 33 | No significant changes in related substances | No significant changes in related substances | No significant changes in related substances |
| 36 | No significant changes in related substances | No significant changes in related substances | No significant changes in related substances |
| 41 | No significant changes in related substances | No significant changes in related substances | No significant changes in related substances |
| 48 | No significant changes in related substances | No significant changes in related substances | No significant changes in related substances |

Note:
"No significant changes in related substances" refers to the difference of properties, contents from the initial values falls into the deviation range of the test equipment.

Conclusion: Edaravone content dropped significantly under the light illumination, and compound linking to edaravone by a ester bond decomposed respectively under high humidity (25° C.±2° C., 90%±5RH), illumination (25° C.±2° C., 60%±5RH, 4500±500LX), and high temperature (60° C.±2° C., 60%±5RH). The compounds of this invention were better than edaravone and the compounds disclosed in CN107400089 under the above-mentioned pharmaceutical stability test conditions.

Test Example 2: Solubility Test

Test method: the dry compound was slowly dissolved into about 0.5 ml distilled water in a 5 ml EP tube until saturation (turbid after ultra-sonic vibration at 25° C.). The solution was filtered and moved to another clean 5 ml EP tube (pre-weighed) and the tube was weighed again to calculate the solution weight. The solution was freeze dried. The remaining solute was weighed to calculate the solvent weight, and then the compound solubility in water was determined.

TABLE 3

| Compound | Solubility(mg/mL) |
|---|---|
| 33 | 10.1 |
| 34 | 12.3 |
| 35 | 18.0 |
| 36 | 4.2 |
| 37 | 6.5 |
| 38 | 3.8 |
| 39 | 5.1 |
| 40 | 3.0 |
| Edaravone | <1.0 |

Conclusion: the compounds of this invention were far more soluble in water than that of the marketed Edaravone, for example, several folds to dozens of folds.

Test Example 3: Cytotoxic Test

1. Test Method

After resuscitating, the PC12 cells were cultured in RPMI-1640 containing 10% horse serum and 5% Fetus Bovine Serum (FBS) under 5% CO$_2$ at 37° C. for two weeks. The medium was changed every other day. The compounds were diluted into solutions of 12.5, 25, 50, 100, 200, 300 μM with culture medium (except examples 33-45 with additional solutions of 400 μM and 500 μM). The PC12 cells were seeded into a 96-well plate at a density of 1.2×10$^4$ cells/well and cultured in a 37° C., 5% CO$_2$ incubator for 24 hours. Remove the medium, the cells were added with the compound solutions of different concentrations as test solutions for another 48 h incubation in a 37° C., 5% CO$_2$ incubator.

After the incubation, the wells were added with 20 μL 5 mg/mL MTT and incubated for 4 hours at 37° C. Carefully removed the medium and added 150 μL DMSO. The plates were placed on an enzyme-labeled instrument and vibrated for 5 min. The absorbance $A_{test\ solution}$ were obtained at 490 nm with the $A_{blank}$ of the well without cells and the $A_{control}$ of the well with untreated cells. The survival rates of the cells in every well were calculated by the formula as Survival rate (%)=($A_{test\ solution}$-$A_{blank}$)/($A_{control}$-$A_{blank}$)*100%

2. Test Results

TABLE 4

| Cytotoxic Test Results | |
|---|---|
| Compound | IC$_{50}$ (μM) |
| 3 | >300 |
| 4 | >300 |
| 5 | >300 |
| 7 | >300 |
| 9 | >300 |
| 13 | 251.5 |

TABLE 4-continued

Cytotoxic Test Results

| Compound | IC$_{50}$ (μM) |
|---|---|
| 16 | 233.9 |
| 17 | >300 |
| 18 | >300 |
| 19 | >300 |
| 24 | 272.3 |
| 25 | >300 |
| 26 | >300 |
| 32 | >300 |
| 33 | >300 |
| 34 | >300 |
| 35 | >300 |
| 36 | >300 |
| 37 | >500 |
| 38 | >500 |
| 39 | >500 |
| 40 | >500 |
| 42 | >300 |
| 47 | 268.9 |
| 49 | >300 |

Conclusion: No obvious toxicity was found in the tested compounds at 100 μM.

Test Example 4: In-Vitro Neuroprotection-I

1. Test Method

Sample Preparation:

All samples were made into 60 mM stock solution by DMSO, which were 200 times diluted to 300 μM by medium. And the final concentration was further diluted into different concentrations by media.

Test Grouping:

Control: Normal cell-plating and same cell medium as other group. 24 hours later, the medium was discarded. Incubate the cell in new media for 24 hours. No compound and hydrogen peroxide treatment. Other steps were the same as the sample test as mentioned below did.

Blank: no cell plating, cell medium, and other steps were the same as the sample test as mentioned below did.

Sample Test:

After resuscitating, the PC12 cells were cultured in RPMI-1640 containing 10% horse serum and 5% Fetus Bovine Serum (FBS) under 5% $CO_2$ at 37° C. for two weeks. The medium was changed every other day. The compounds were diluted into solutions of 12.5, 25, 50, 100, 200, 300 μM with culture medium (except that examples 33-45 with additional solutions of 400 μM and 500 μM). The PC 12 cells were seeded into a 96-well plate at a density of $8 \times 10^3$ cells/well and cultured in a 37° C., 5% $CO_2$ incubator for 24 hours. Removed the medium, the cells were added with the compound solutions of different concentrations as test solutions for another 48 h incubation in a 37° C., 5% $CO_2$ incubator. After the incubation, apart from the blank and control groups, the wells (including 0 μM drug group) were added to the medium-prepared 200 μM $H_2O_2$, and continued for another 24 h incubation in a 37° C., 5% $CO_2$ incubator.

After the incubation, the wells were added with 20 μL 5 mg/mL MTT and incubated for 4 hours at 37° C. Carefully removed the medium and added 150 μL DMSO. The plates were placed on an enzyme-labeled instrument and vibrated for 5 min. The absorbance $A_{test}$ solution were obtained at 490 nm with the $A_{blank}$ of the well without cells and the $A_{control}$ of the well with untreated cells. The survival rate of the cells in every well by the formula survival rate (%)= $(A_{test\ solution} - A_{blank})/(A_{control} - A_{blank}) \ast 100\%$.

2. Test Results

TABLE 5

Results of in vitro neuroprotection test

| Compound | EC$_{50}$ (μM) |
|---|---|
| 1 | 66.4 |
| 3 | 98.0 |
| 4 | 69.5 |
| 6 | 56.8 |
| 7 | 88.9 |
| 8 | 100.4 |
| 9 | 120.5 |
| 10 | 55.7 |
| 12 | 89.0 |
| 13 | 110.0 |
| 14 | 45.2 |
| 15 | 67.2 |
| 16 | 48.0 |
| 17 | 94.9 |
| 18 | 75.0 |
| 21 | 82.1 |
| 22 | 103.2 |
| 23 | 123.7 |
| 24 | 44.7 |
| 25 | 59.3 |
| 26 | 54.8 |
| 28 | 85.9 |
| 30 | 77.2 |
| 31 | 91.2 |
| 32 | 80.7 |
| 33 | 111.9 |
| 34 | 120.3 |
| 35 | 87.9 |
| 36 | 79.6 |
| 37 | 90.0 |
| 39 | 55.0 |
| 40 | 54.7 |
| 41 | 55.1 |
| 42 | 75.4 |
| 43 | 58.1 |
| 44 | 77.9 |
| 45 | 75.3 |
| 46 | 90.1 |
| 47 | 53.6 |
| 48 | 122.7 |
| 50 | 100.9 |
| 52 | 78.6 |
| ED | 170.8 |

Conclusion: The results showed that the substituted pyrazole compounds of this invention effectively protected the nerve cells from injuries at the presence of the peroxides, or ROS free radicals. The injuries of free radicals to the cerebral nerve cell and mitochondria were the commonly recognized pathological mechanism of stroke, cerebral embolism, stroke sequelae, stroke motor dysfunction, mitochondrial encephalomyopathy, and amyotrophic lateral sclerosis. Selecting and using the effective radical injury-targeted drugs for the patients suffering from these diseases in clinic were one of the major ways to tackle the problem.

Test Example 5: In Vivo Drug Efficacy Test of MCAO Model

1. Test Method 1.1 Model Preparation

SD rats fasted and were allowed free access to water. The rats were anesthetized with isoflurane gas and maintained on the day of the experiment. They were immobilized in the supine position and the skin along the central line of neck was cut to expose the right common carotid artery. Then carefully separated the nerve and fascia around the vessels from the common carotid artery bifurcation (CCAB) down to the skull base. Next, the branch occipital artery of the external carotid artery, superior thyroid artery, lingual artery, and palate maxillary artery were separated and occluded. A 0.260 mm nylon suture was inserted into the free end of external carotid artery, running through the distal end of the external carotid artery to the internal carotid artery, entering cerebral arterial part (Willis cirle) to effectively block the cerebral artery. The inserting length of the nylon suture was 18-20 mm away from the CCAB. Then the free end of CCA and the nylon suture were ligated together. The fascia and the skin should be sutured sequentially. Penicillin was injected intramuscularly to prevent infection. In the sham group, only the internal carotid artery was separated.

Two hours after MCAO, carefully pulled out the nylon suture from the internal carotid artery to reperfuse the vessels. Ten minutes later, neurological deficit score was used to determine the established model rats with obvious neurological deficits (more than 8)

1.2 Administration Grouping

The well-established model animals were randomized into groups by a random number table. Every group had ten rats. The groups included model control group, drug group, edaravone group and a sham of ten rats.

The rats were administered through tail vein infusion for 30 min. The sham and model control groups were administered with the same volume of saline.

1.3 Effects on Neurofunction

Before and after administration at 24 h, the neurological deficit was blind-scored according to Table 6 to evaluate the neurological severity score with a total score of 16. The higher score, the more severe the deficit was. Compared with model control group, the percentage of loss in every group reflected the improvements of the neurological deficit. The improvement of neurofunction (%)=(Model control−Drug group or Edaravone group)/Model control*100%. See Table 7.

1.4 Test of Cerebral Infarction Area

After the experiment, the brain was removed and cut into 2 mm thick slices along the coronal plane. Half of the brain slices were taken at intervals and incubated in 2% TTC staining solution at 37° C. for 10 min in the dark. Digital imaging system stored the images in the computer, measured the infarct area, the whole brain area with the image analysis system v4.0, and calculated the cerebral infarction area (Percentage of the infarct area to the whole brain area).

1.5 Statistical Processing

All data were shown in the form of mean±standard deviation ($\bar{x}\pm s$). One-way analysis of variance compared the differences between groups. The LSD method was used for comparison between the two groups. P<0.05 indicates that the difference is statistically significant.

2. Test Results

TABLE 7

MCAO results

| Group | Improvements of nerve function (%) | Cerebral infarction area (%) |
|---|---|---|
| Sham | unavailable | 0 |
| Model control | 1.25 | 30.2 |
| ED | 15.7 | 20.1 |
| 9 | 16.0 | 19.8 |
| 13 | 17.2 | 17.5 |
| 15 | 15.9 | 20.0 |
| 16 | 16.2 | 19.9 |
| 33 | 24.0 | 14.0 |
| 34 | 21.1 | 14.5 |
| 35 | 22.2 | 15.8 |
| 36 | 24.1 | 14.1 |
| 37 | 17.5 | 17.6 |
| 38 | 17.0 | 17.8 |
| 39 | 16.9 | 18.0 |
| 40 | 16.8 | 18.5 |

TABLE 6

Neurological severity score in rats

| Items | Behavior | Score |
|---|---|---|
| 1. Motor test | 1) Lifting the rat by tail | |
| | Forelimb flexion | 1 |
| | Hindlimb flexion | 1 |
| | Raising head within 30 s >10° (between the vertical axis) | 1 |
| | 2) Floor walking (, normal = 0, max value = 3) | |
| | Normal walking | 0 |
| | Unable to walk straight | 1 |
| | Circle to the paralytic side | 2 |
| | Topple to the paralytic side | 3 |
| 2. Beam balance test | Keep balance and stable posture | 0 |
| | Grasp the side of the beam | 1 |
| | Hug beam and 1 limb falls off the beam | 2 |
| | Hug beam and 2 limbs fall off the beam Or spin on the beam for more than 60 s | 3 |
| | Attempt to balance on beam(>40 s), but fall off | 4 |
| | Attempt to balance on beam (>20 s), but fall off | 5 |
| | Fall off, no attempt to balance or hang on to the beam | 6 |
| 3.Reflex losses Or abnormal movement | Pinna reflex (shaking head when touching the ear canal) | 1 |
| | Corneal reflex (blink when gently touching the cornea with cotton) | 1 |
| | Panic reflex (tearing paper induces a motor response) | 1 |
| | Seizures, myoclonus, dystonia | 1 |
| Total | 16 | |

TABLE 7-continued

MCAO results

| Group | Improvements of nerve function (%) | Cerebral infarction area (%) |
|---|---|---|
| 42 | 15.9 | 19.7 |
| 43 | 16.1 | 19.8 |

Conclusion: In the rat model of focal cerebral infarction caused by middle cerebral artery ischemia-reperfusion, the above-mentioned compounds of the present invention can have different therapeutic effects by single-dose intravenous infusion, which improved the damaged nerve function to varying degrees and reduced the cerebral infarction area and the degree of cerebral edema.

Test Example 6: In Vivo Efficacy Test of II-ALS Model

1. Test Method:

B6SJL-Tg (SOD1*G93A) mice were intraperitoneally administered single-doses once a day for 4 consecutive weeks. The weight of the mice was determined before and after the administration every week. The motor function of the mice was determined by rota-rod and PaGE tests with the time points before and after 4-week administration. The mice plasma was collected and detected for SOD levels through ELISA. The Index Evaluation described below was used to evaluate the efficacy of the compounds of the examples in ALS model and to what extent the compounds of the examples improve the survival period and motor activity.

1.1 Test Grouping and Administration Method

The animals were delivered to the SPF animal room and raised for more than one week. Five days before the test, the mice were accustomed to a round of tests per day. The mice were randomly divided into groups according to their body weights, 8 mice for each group. Among them, the solvent group was given with the same volume of solvent (physiological saline) every day.

1.2 Volume

The mice were administered with a volume of 10 ml/kg.

1.3 Means and Time of Administration i.p once a day for 4 weeks.

1.4 Index Evaluation

Index evaluation time started from the beginning of the experiment to the death of the animals.

1) ALS onset time: For 2 consecutive observation days, the mice appeared limb, tremor and/or limb weakness at tail suspension were determined as the ALS onset. The determination of limb weakness: the mice were placed on the rota-rod device with a diameter of 3.5 cm. The speed is set to 15 rpm to record the longest fall latency divided by 420 s. The mice of less 420 s were determined as limb weakness.

2) Rota-rod Test: The mice were placed on the rota-rod device with a diameter of 3.5 cm. The speed is set to 12 rpm to record the longest fall latency divided by 180 s. The latency of more than 180 s was recorded as 180 s, and actual time was recorded when less than 180 s. The fall latency of the ALS mice in groups during the rota-rod test is shown in Table 1.

3) Paw Grip Endurance (PaGE) Test: The mice were placed on the traditional wire grid. The grid was gently shaken to cause the mice to tighten its grip on the wires then inverted, and time recording commenced. The time was recorded until the mouse lost its grip in hind limbs divided by 90 s. The time more than 90 s was recorded as 90 s, while the time less than 90 s was recorded by its actual time. The test was completed in triplicate with the highest score used for analysis. The fall latency of the ALS mice in groups during the PaGE test is shown in Table 2.

4) Death time of the mouse: Placed the mouse in the supine position and failed to turn over to the prone position within 20 seconds.

5) Plasma SOD concentration: The blood was collected and mixed with EP tube containing heparin before and after administration at the 4th week, and then centrifuged at 1000 g for 10 min. The plasma was collected and stored in aliquots at −70° C. ELISA kit was used to detect plasma SOD levels.

2. Test Results

TABLE 8

ALS Model Test Results

| Group | Dosage (μmol/kg) | Onset time(d) | Rotarod Time | PaGE | Survival time(d) | Plasma SOD concentration on day 28th(U/mL) |
|---|---|---|---|---|---|---|
| Solvent control | | 108.00 ± 8.02 | | | 135.13 ± 7.53 | 133.59 ± 13.95 |
| 24 | 86 | 118.29 ± 6.32* | + | + | 147.71 ± 8.94 | 150.55 ± 11.88* |
| 33 | 86 | 118.25 ± 5.87* | + | + | 149.88 ± 8.37 | 155.18 ± 15.37* |
| ED | 86 | 116.14 ± 7.82 | + | + | 147.00 ± 8.94 | 153.88 ± 9.91* |

Note:
① "+" indicates a significant difference compared with the solvent group, p < 0.05.
② The compound group of the examples and the ED group were administered equimolar.
③ *indicates a statistical difference compared with the solvent group, p < 0.05.

CONCLUSIONS

Through 28-day drug intervention: (1) Compared with the solvent group, the onset time of ALS mice in each group was delayed to varying degrees; (2) The rota-rod test and the PaGE test showed that the fall latency of each drug group was extended, and group 24 and 33 are better than the marketed drug edaravone, exhibiting significantly efficacious; (3) the survival time of ALS mice in each administration group was significantly prolonged; (4) Plasma SOD showed that in the 28$^{th}$ day after administration, the plasma SOD levels of mice in the administration groups were significantly higher than that of mice in the solvent group, proving the compound administered stop the decreases of SOD levels.

The invention claimed is:

1. A substituted pyrazole compound of formula (I), or a pharmaceutically acceptable salt thereof, or a solvate thereof,

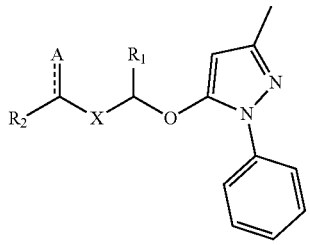

(I)

wherein:
$R_1$ is H or methyl;
X is —O— or —NH—;
⚌ is a double bond and A is O;
$R_2$ is $C_1$-$C_{17}$ branched or linear alkyl, $C_{3-6}$ cycloalkyl, phenyl-$C_1$-$C_6$ alkyl, pyridyl, phenyl optionally substituted by one or more than one group selected from hydroxyl, $C_{1-6}$ alkanoyloxy, $C_{1-6}$ alkoxy acyloxy or —NR'R", wherein R' and R" are each independently $C_1$-$C_6$ linear or branched alkyl;
or, ⚌ is a single bond, the following formula (i) in formula (I)

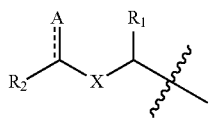

(i)

forms the group of the formula (ii)

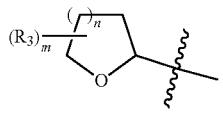

(ii)

wherein n is 1 or 2, and m is 1, 2, 3 or 4;
$R_3$ is independently hydroxy, hydroxymethyl, or unsubstituted or mono-substituted amino with $C_{1-6}$ alkanoyl;
wherein the alkyl moiety of the "branched or linear alkyl", "alkoxy", "arylalkoxy", and "alkanoyloxy" is each independently a $C_{1-20}$ linear or branched alkyl; a $C_{1-17}$ linear or branched alkyl; a $C_{1-8}$ linear or branched alkyl; a $C_{1-6}$ linear or branched alkyl; a $C_{1-4}$ linear or branched alkyl; methyl, ethyl, n-propyl, isopropyl, n-butyl, isobutyl, tert-butyl, sec-butyl, n-pentyl, isopentyl, neopentyl, tert-pentyl, n-hexyl, isohexyl, heptyl, n-octyl, n-nonyl, n-decyl, dodecyl, pentadecyl or hexadecyl;
wherein the "cycloalkyl" is a $C_{3-8}$ cycloalkyl, a cyclopropyl, cyclobutyl, cyclopentyl, or cyclohexyl.

2. The substituted pyrazole compound of formula (I), or the pharmaceutically acceptable salt thereof, or the solvate thereof according to claim 1, wherein the substituted pyrazole compound of formula (I) is a compound of the following formula II, III or IV,

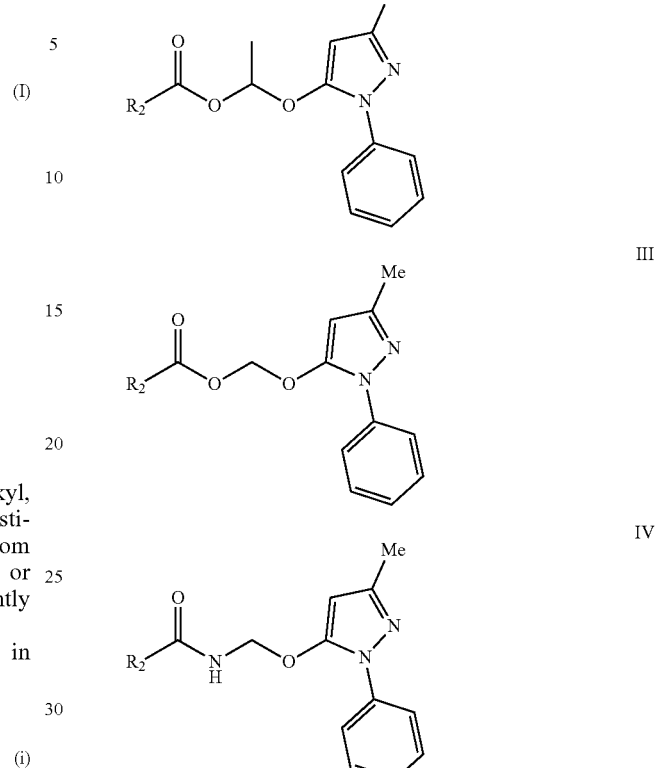

wherein $R_2$ is as defined in claim 1.

3. The substituted pyrazole compound of formula (I), or the pharmaceutically acceptable salt thereof, or the solvate thereof according to claim 1, wherein the compound of formula (I) is selected from the following compounds:

| No. | Structure |
|---|---|
| 1 | ![structure 1] |
| 2 | ![structure 2] |

| No. | Structure |
|---|---|
| 3 | 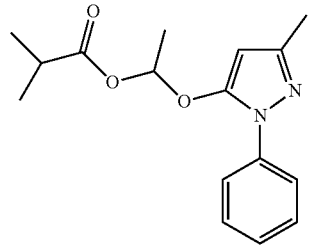 [SMILES: Cc1cc(OC(C)OC(=O)C(C)C)n(-c2ccccc2)n1] |
| 4 | 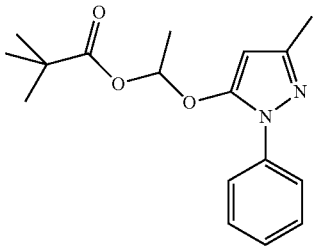 [SMILES: Cc1cc(OC(C)OC(=O)C(C)(C)C)n(-c2ccccc2)n1] |
| 5 | 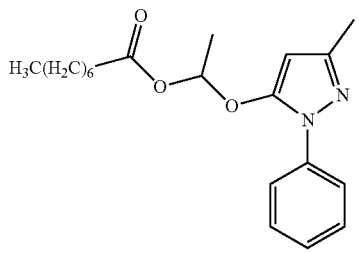 |
| 6 | 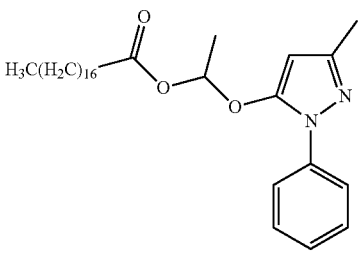 |
| 7 | 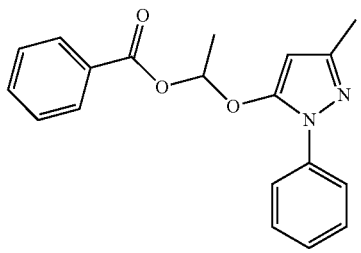 [SMILES: Cc1cc(OC(C)OC(=O)c2ccccc2)n(-c2ccccc2)n1] |
| 8 | 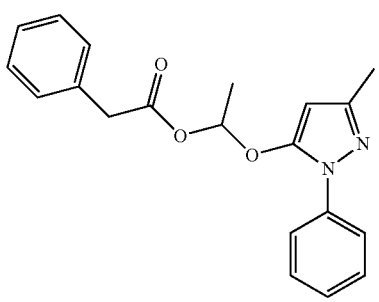 [SMILES: Cc1cc(OC(C)OC(=O)Cc2ccccc2)n(-c2ccccc2)n1] |
| No. | Structure |
|---|---|
| 9 | 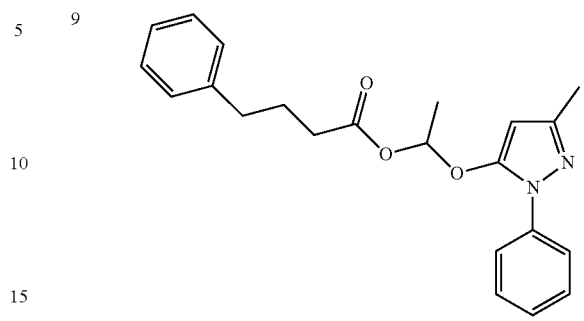 |
| 10 | 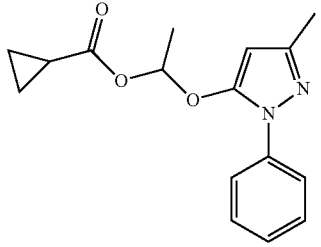 [SMILES: Cc1cc(OC(C)OC(=O)C2CC2)n(-c2ccccc2)n1] |
| 11 | 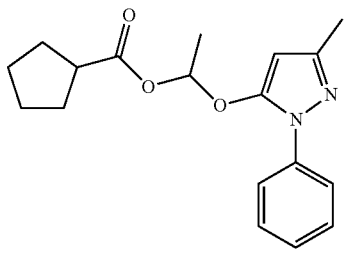 [SMILES: Cc1cc(OC(C)OC(=O)C2CCCC2)n(-c2ccccc2)n1] |
| 12 | 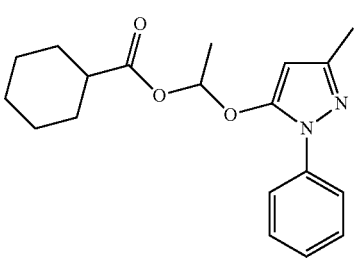 [SMILES: Cc1cc(OC(C)OC(=O)C2CCCCC2)n(-c2ccccc2)n1] |
| 13 | 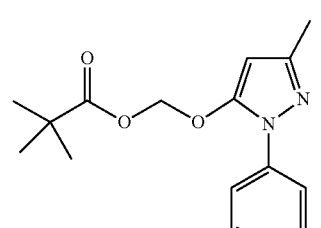 |
| 14 | 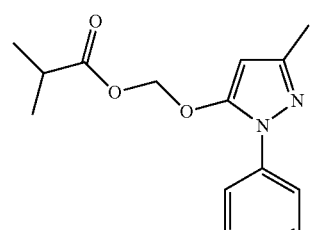 |

| No. | Structure |
|---|---|
| 15 | 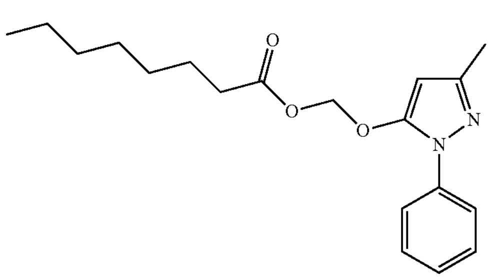 [SMILES: CCCCCCCC(=O)OCOc1cc(C)nn1-c1ccccc1] |
| 16 | 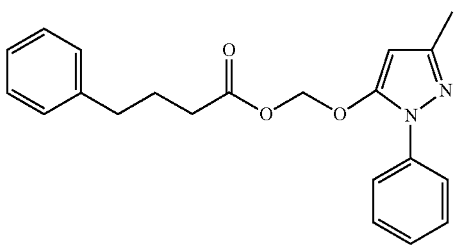 [SMILES: Cc1cc(OCOC(=O)CCCc2ccccc2)n(-c2ccccc2)n1] |
| 17 | 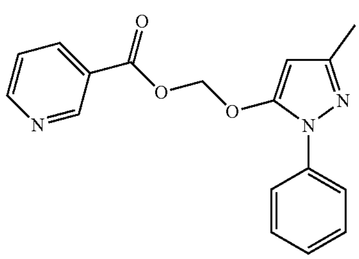 [SMILES: Cc1cc(OCOC(=O)c2cccnc2)n(-c2ccccc2)n1] |
| 18 | 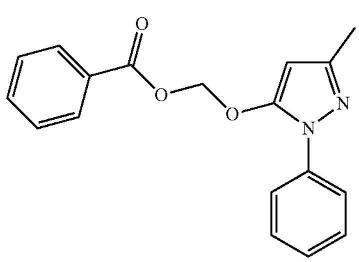 [SMILES: Cc1cc(OCOC(=O)c2ccccc2)n(-c2ccccc2)n1] |
| 19 | 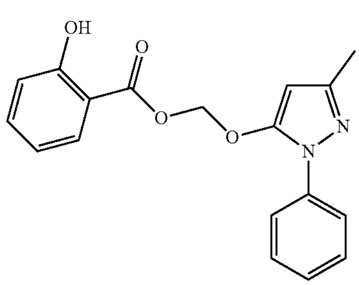 [SMILES: Cc1cc(OCOC(=O)c2ccccc2O)n(-c2ccccc2)n1] |
| 20 | |
| 21 | |
| 22 | |
| 23 | |
| 24 | |

| No. | Structure |
|---|---|
| 25 | 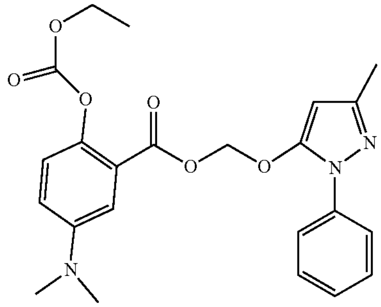 [SMILES: CCOC(=O)Oc1ccc(N(C)C)cc1C(=O)OCOc1cc(C)nn1-c1ccccc1] |
| 26 | 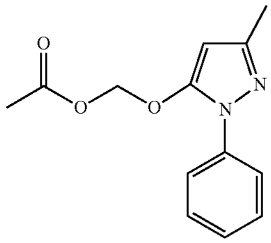 [SMILES: CC(=O)OCOc1cc(C)nn1-c1ccccc1] |
| 27 | 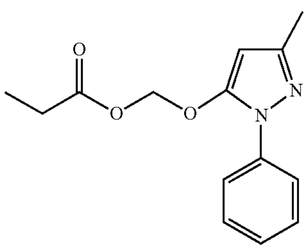 [SMILES: CCC(=O)OCOc1cc(C)nn1-c1ccccc1] |
| 28 | 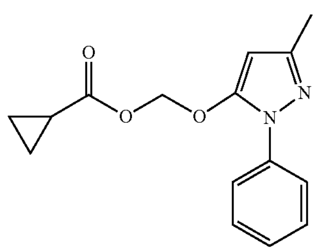 [SMILES: Cc1cc(OCOC(=O)C2CC2)n(-c2ccccc2)n1] |
| 29 | 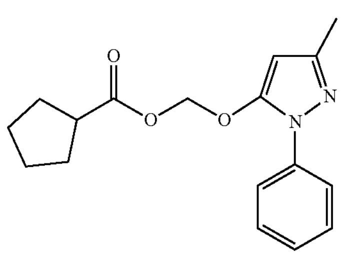 [SMILES: Cc1cc(OCOC(=O)C2CCCC2)n(-c2ccccc2)n1] |
| 30 | 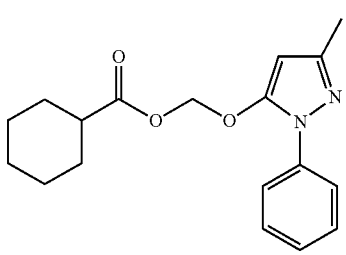 [SMILES: Cc1cc(OCOC(=O)C2CCCCC2)n(-c2ccccc2)n1] |
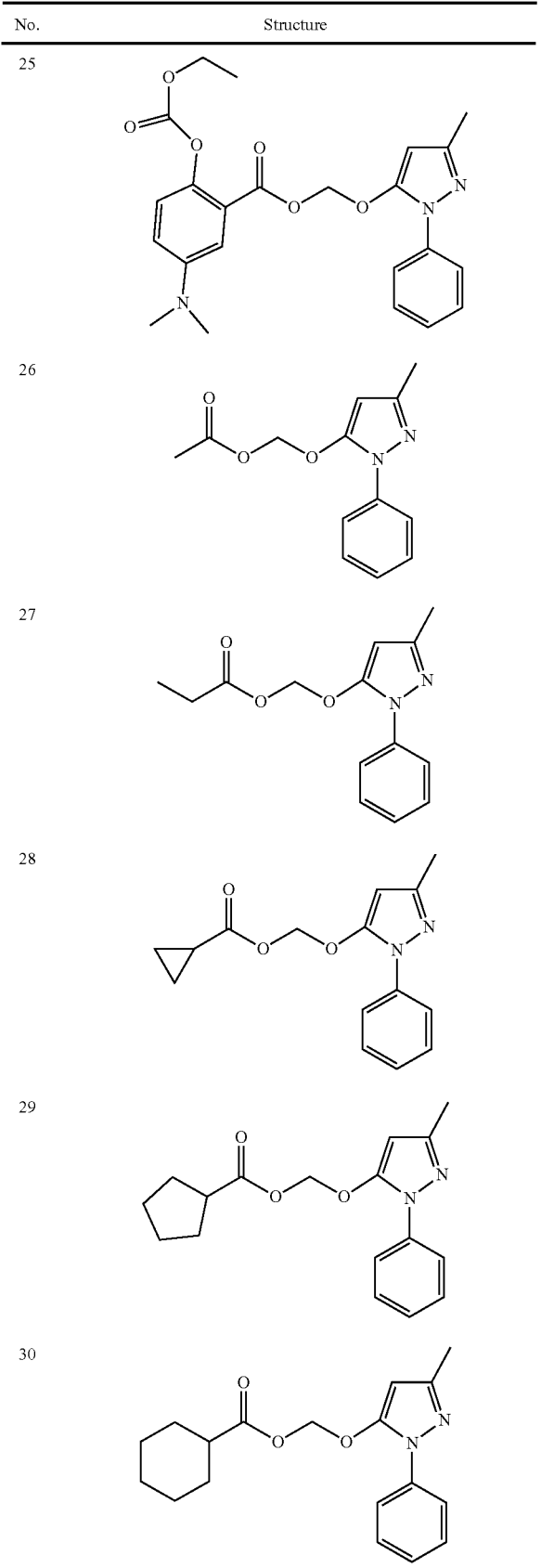
| No. | Structure |
|---|---|
| 31 | 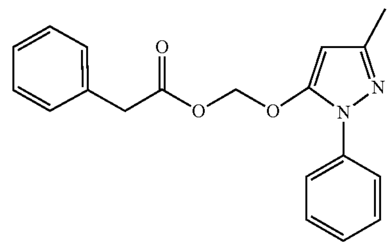 [SMILES: Cc1cc(OCOC(=O)Cc2ccccc2)n(-c2ccccc2)n1] |
| 32 | 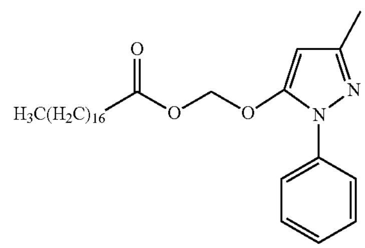 |
| 33 | 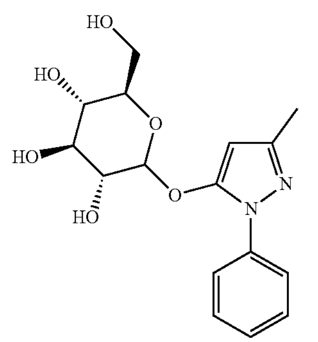 [SMILES: Cc1cc(OC2O[C@H](CO)[C@@H](O)[C@H](O)[C@H]2O)n(-c2ccccc2)n1] |
| 34 | 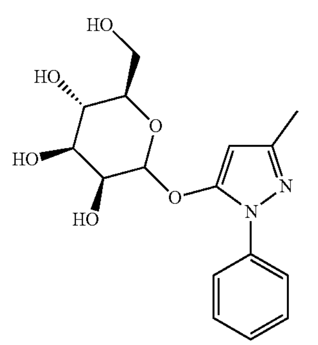 [SMILES: Cc1cc(OC2O[C@H](CO)[C@@H](O)[C@H](O)[C@@H]2O)n(-c2ccccc2)n1] |
| 35 | 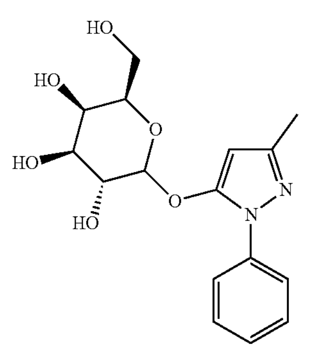 [SMILES: Cc1cc(OC2O[C@H](CO)[C@H](O)[C@H](O)[C@H]2O)n(-c2ccccc2)n1] |
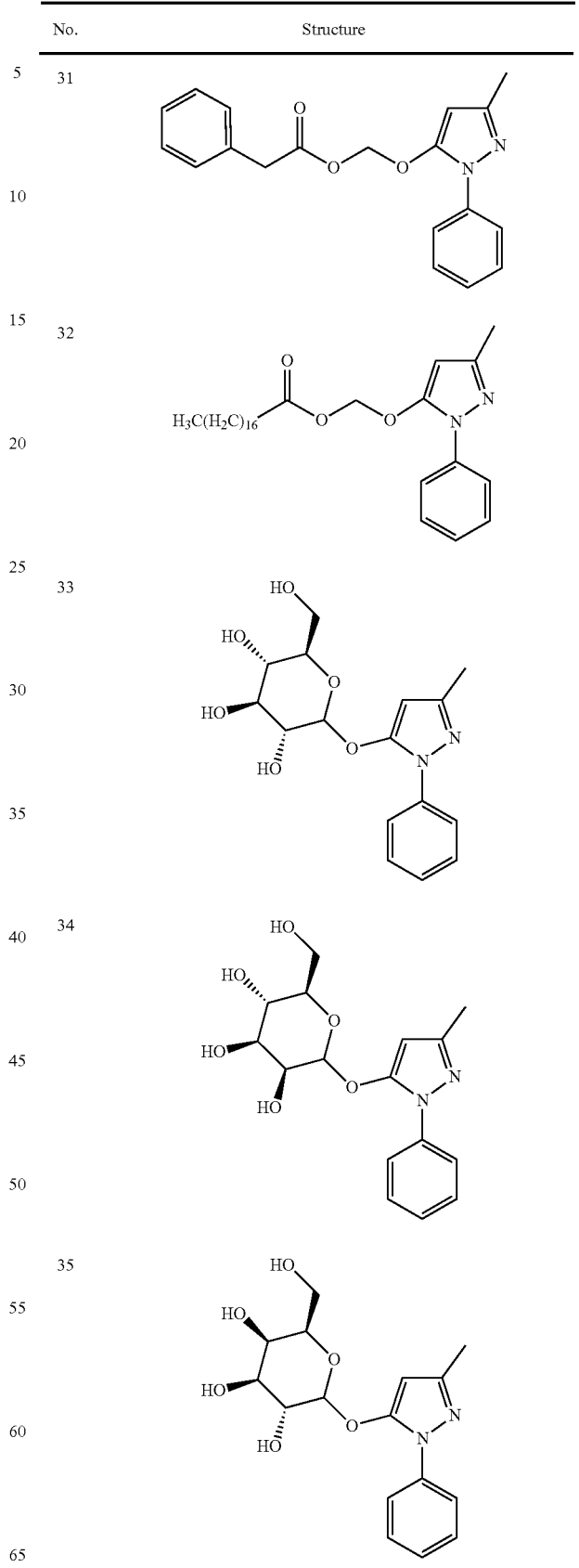

| No. | Structure |
|---|---|
| 36 | 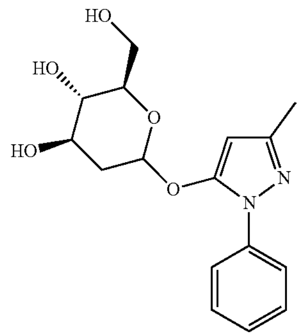 [SMILES: Cc1cc(OC2C[C@@H](O)[C@H](O)[C@@H](CO)O2)n(-c2ccccc2)n1] |
| 37 | 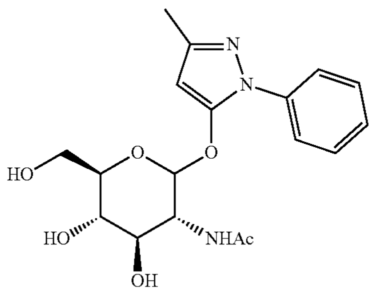 [SMILES: CC(=O)N[C@H]1C(Oc2cc(C)nn2-c2ccccc2)O[C@H](CO)[C@@H](O)[C@@H]1O] |
| 38 | 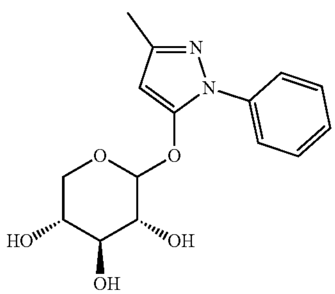 [SMILES: Cc1cc(OC2OC[C@@H](O)[C@H](O)[C@H]2O)n(-c2ccccc2)n1] |
| 39 | 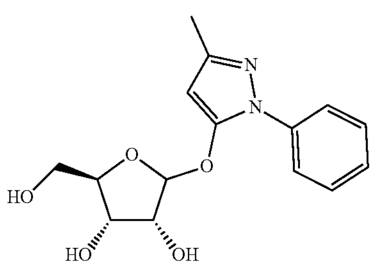 [SMILES: Cc1cc(OC2O[C@H](CO)[C@@H](O)[C@H]2O)n(-c2ccccc2)n1] |
| 40 | 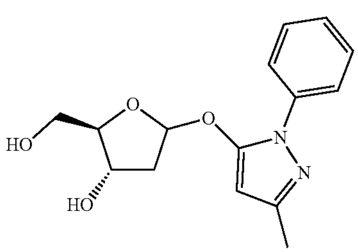 [SMILES: Cc1cc(OC2C[C@H](O)[C@@H](CO)O2)n(-c2ccccc2)n1] |

| No. | Structure |
|---|---|
| 41 | 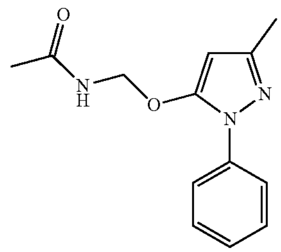 [SMILES: CC(=O)NCOc1cc(C)nn1-c1ccccc1] |
| 42 | 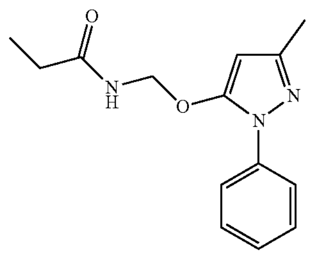 [SMILES: CCC(=O)NCOc1cc(C)nn1-c1ccccc1] |
| 43 | 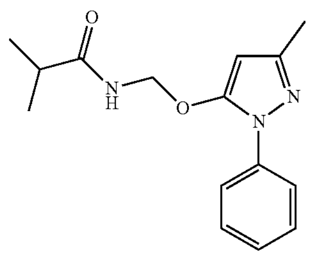 [SMILES: Cc1cc(OCNC(=O)C(C)C)n(-c2ccccc2)n1] |
| 44 | 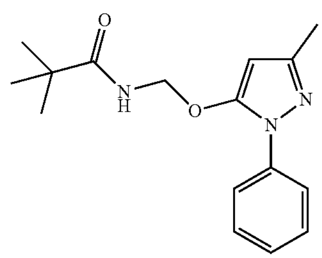 [SMILES: Cc1cc(OCNC(=O)C(C)(C)C)n(-c2ccccc2)n1] |
| 45 | 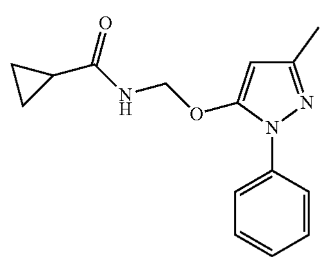 [SMILES: Cc1cc(OCNC(=O)C2CC2)n(-c2ccccc2)n1] |
| 46 | 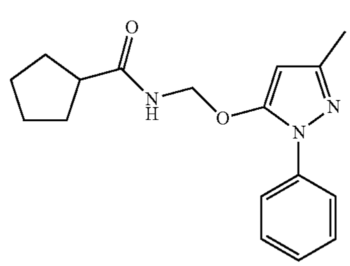 [SMILES: Cc1cc(OCNC(=O)C2CCCC2)n(-c2ccccc2)n1] |

| No. | Structure |
|---|---|
| 47 | (cyclohexyl-C(=O)-NH-CH2-O-pyrazole(3-methyl, 1-phenyl)) |
| 48 | (phenyl-C(=O)-NH-CH2-O-pyrazole(3-methyl, 1-phenyl)) |
| 49 | (phenyl-CH2-C(=O)-NH-CH2-O-pyrazole(3-methyl, 1-phenyl)) |
| 50 | (phenyl-(CH2)3-C(=O)-NH-CH2-O-pyrazole(3-methyl, 1-phenyl)) |
| 51 | H₃C(H₂C)₆-C(=O)-NH-CH2-O-pyrazole(3-methyl, 1-phenyl) |
| 52 | H₃C(H₂C)₁₆-C(=O)-NH-CH2-O-pyrazole(3-methyl, 1-phenyl) |

4. A substituted pyrazole compound of formula (I), or a pharmaceutically acceptable salt thereof, or a solvate thereof, (I)

wherein
the following formula (i) in formula (I)

(i)

forms the group of the following formula (iii) or (iv), (iii)

or (iv)

wherein, $R'_1$ is hydrogen, hydroxymethyl or $C_{1-4}$ here; $R'_2$ is hydroxy or $C_{1-4}$ alkanoyloxy; $R'_3$ is hydrogen, hydroxy, $C_{1-4}$ alkanoyloxy, amino, or $C_{1-4}$ alkanoylamino.

5. The substituted pyrazole compound of formula (I), or the pharmaceutically acceptable salt thereof, or the solvate thereof according to claim 4, wherein the formula (i) of the formula (I) forms the groups shown in the following formulas,

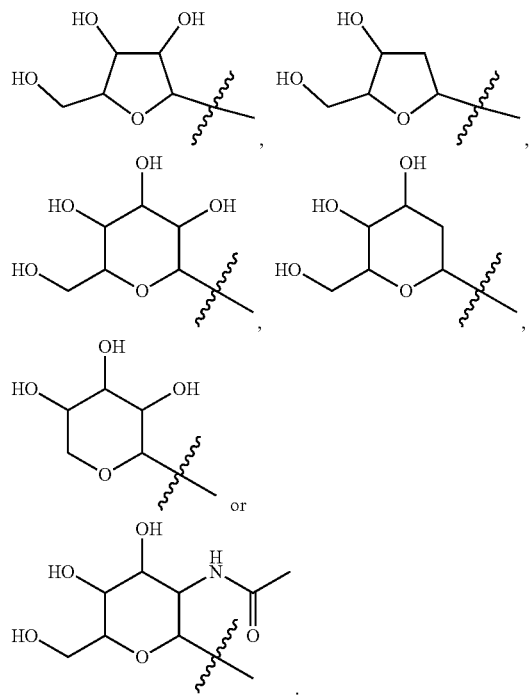

6. A pharmaceutical composition comprising one or more than one of the substituted pyrazole compounds of formula (I) or the pharmaceutically acceptable salt thereof, or the solvate thereof according to any one of claims 1 and 2-3 and pharmaceutically acceptable carriers.

7. A preparation method for the substituted pyrazole compound of the formula (I), or the pharmaceutically acceptable salt thereof, or the solvate thereof according to any one of claims 1 and 2-3, comprising the step of the reaction between a compound of formula (A) and edaravone under alkaline conditions,

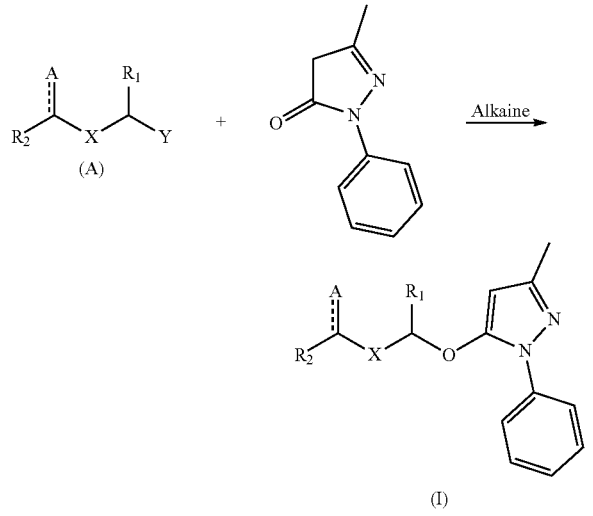

wherein Y is a halogen.

8. The preparation method according to claim 7, wherein, the compound of formula (I) is the compound of formula (II), and the synthetic route of the preparation method is as follows:

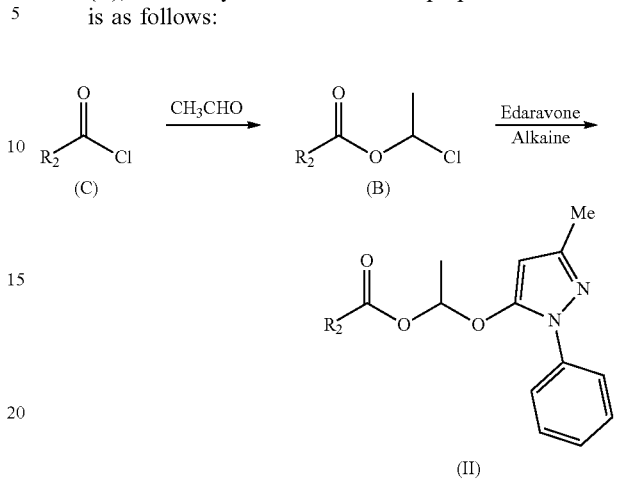

comprising:
reacting a compound of formula (C) with acetaldehyde under a catalyst to obtain a compound of formula (B);
reacting the compound of formula (B) with edaravone under alkaline conditions to prepare the compound of formula (II);
wherein the preparation method of the formula (C) comprises reacting a compound of the formula (D) and thionyl chloride;

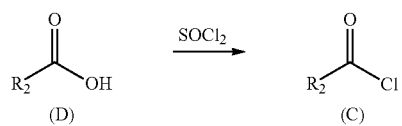

or,
the compound of formula (I) is the compound of formula (III), and the synthetic route of the preparation method is as follows:

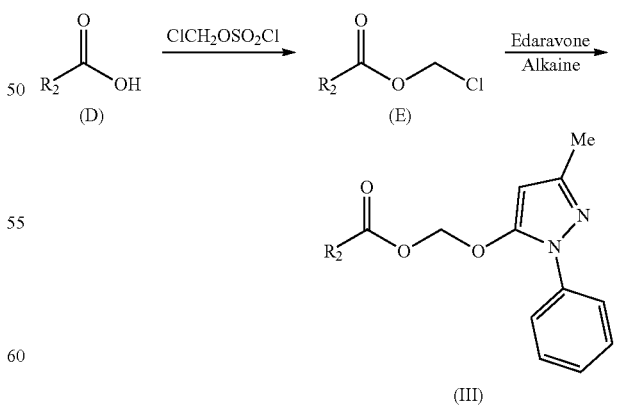

comprising:
reacting the compound of formula (D) reacts with chloromethyl chlorosulfonate to obtain a compound of formula (E);

reacting the compound of formula (E) with edaravone under alkaline conditions to prepare the compound of formula (III);

or, the compound of formula (I) is the compound of formula (IV), and the synthetic route of the preparation method is as follows:

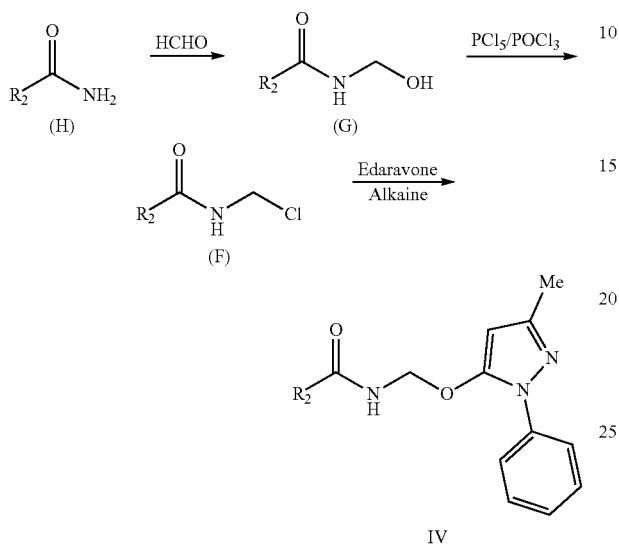

comprising:
reacting a compound of formula (H) with formaldehyde to obtain the compound of formula (G);
reacting the compound of formula (G) reacts with $PCl_5/POCl_3$ to prepare a compound of formula (F),
reacting the compound of formula (F) reacts with edaravone under alkaline conditions to prepare the compound of formula (IV);

or, the compound of formula (I) is the compound of the following formula (V), and the synthetic route of the preparation method is as follows:

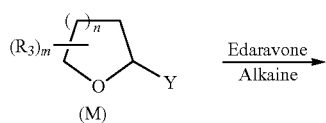

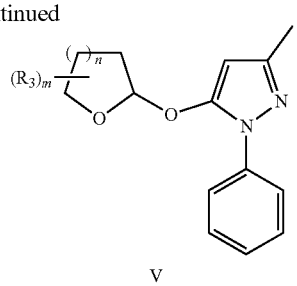

wherein Y is Cl or Br, which comprises the step of reacting a compound of the formula (M) and edaravone under alkaline conditions to prepare the compound of formula (V)

wherein:

$R_2$ is $C_1$-$C_{17}$ branched or linear alkyl, $C_{3-6}$ cycloalkyl, phenyl-$C_1$-$C_6$ alkyl, pyridyl, phenyl optionally substituted by one or more than one qroup selected from hydroxyl, $C_{1-6}$ alkanoyloxy, $C_{1-6}$ alkoxy acyloxy or —NR'R", wherein:

R' and R" are each independently $C_1$-$C_6$ linear or branched alkyl, the alkyl moiety of the "branched or linear alkyl", "alkoxy", "arylalkoxy", and "alkanoyloxy" is each independently a $C_{1-20}$ linear or branched alkyl; a $C_{1-17}$ linear or branched alkyl; a $C_{1-8}$ linear or branched alkyl; a $C_{1-6}$ linear or branched alkyl; a $C_{1-4}$ linear or branched alkyl; methyl, ethyl, n-propyl, isopropyl, n-butyl, isobutyl, tert-butyl, sec-butyl, n-pentyl, isopentyl, neopentyl, tert-pentyl, n-hexyl, isohexyl, heptyl, n-octyl, n-nonyl, n-decyl, dodecyl, pentadecyl or hexadecyl; and the "cycloalkyl" is a $C_{3-8}$ cycloalkyl, a cyclopropyl, cyclobutyl, cyclopentyl, or cyclohexyl;

$R_3$ is independently hydroxy, hydroxymethyl, or unsubstituted or mono-substituted amino with $C_{1-6}$ alkanoyl;

m is 1, 2, 3 or 4; and n is 1 or 2.

9. A method of treating stroke, cerebral embolism, stroke sequelae, stroke-related motor dysfunction, mitochondrial encephalomyopathy, or amyotrophic lateral sclerosis in a subject, the method comprising administering to the subject the substituted pyrazole compound of formula (I) or the pharmaceutically acceptable salt thereof, or the solvate thereof according to any one of claims 1 and 2-3 or the pharmaceutical composition thereof.

\* \* \* \* \*